(12) United States Patent
To et al.

(10) Patent No.: US 8,066,766 B2
(45) Date of Patent: Nov. 29, 2011

(54) METHODS AND DEVICES FOR TERMINATION

(75) Inventors: John To, Newark, CA (US); Niel F. Starksen, Los Altos Hills, CA (US); Tenny C. Calhoun, Mountain View, CA (US); Brian Tang, Fremont, CA (US)

(73) Assignee: Guided Delivery Systems Inc., Santa Clara, CA (US)

( * ) Notice: Subject to any disclaimer, the term of this patent is extended or adjusted under 35 U.S.C. 154(b) by 1045 days.

(21) Appl. No.: 11/894,530

(22) Filed: Aug. 20, 2007

(65) Prior Publication Data

US 2008/0051837 A1    Feb. 28, 2008

Related U.S. Application Data

(63) Continuation of application No. 11/270,034, filed on Nov. 8, 2005, which is a continuation-in-part of application No. 11/232,190, filed on Sep. 20, 2005, now Pat. No. 7,883,538, which is a continuation-in-part of application No. 10/792,681, filed on Mar. 2, 2004, which is a continuation-in-part of application No. 10/741,130, filed on Dec. 19, 2003, which is a continuation-in-part of application No. 10/656,797, filed on Sep. 4, 2003, now Pat. No. 7,753,922, and a continuation-in-part of application No. 10/461,043, filed on Jun. 13, 2003, now Pat. No. 6,986,775.

(60) Provisional application No. 60/459,735, filed on Apr. 1, 2003, provisional application No. 60/462,502, filed on Apr. 10, 2003, provisional application No. 60/524,922, filed on Nov. 24, 2003, provisional application No. 60/388,935, filed on Jun. 13, 2002, provisional application No. 60/429,288, filed on Nov. 25, 2002, provisional application No. 60/445,890, filed on Feb. 6, 2003.

(51) Int. Cl.
*A61F 2/24* (2006.01)

(52) U.S. Cl. ........ 623/2.11; 606/144; 606/232; 623/2.36

(58) Field of Classification Search ................ 623/2.36, 623/2.37, 2.11; 606/139, 142, 144, 232
See application file for complete search history.

(56) References Cited

U.S. PATENT DOCUMENTS 2,108,206 A    2/1938    Meeker
(Continued)

FOREIGN PATENT DOCUMENTS

EP    0 669 101 A1    8/1995
(Continued)

OTHER PUBLICATIONS

European Examination Communication mailed on Dec. 8, 2009, for EP Application No. 06 837 222.6 filed on Nov. 8, 2006, three pages.
(Continued)

*Primary Examiner* — Gary Jackson
*Assistant Examiner* — Katherine Dowe
(74) *Attorney, Agent, or Firm* — Morrison & Foerster LLP

(57) ABSTRACT

Devices and methods used in termination of a tissue tightening procedure are described. Termination includes the cinching of a tether to tighten the tissue, locking the tether to maintain tension, and cutting excess tether. In procedures involving anchors secured to the tissue, the tether is coupled to the anchors and the tissue is tightened via tension applied to the anchors by cinching the tether. In general, the devices and methods can be used in minimally invasive surgical procedures, and can be applied through small incisions or intravascularly. A method for tightening tissue by fixedly coupling a first anchor to a tether and slidably coupling a second anchor to the tether, securing both anchors to the tissue, applying tension to the tether intravascularly, fixedly coupling the tether to the second anchor, and cutting the tether is described. The tissue to be tightened can comprise heart tissue, in particular heart valve annulus tissue. Various devices and methods for locking the tether in place and cutting excess tether are described.

10 Claims, 50 Drawing Sheets

U.S. PATENT DOCUMENTS

| | | |
|---|---|---|
| 3,656,185 A | 4/1972 | Carpentier |
| 3,727,614 A | 4/1973 | Kniazuk |
| 3,773,034 A | 11/1973 | Burns et al. |
| 3,961,419 A | 6/1976 | Schwartz |
| 3,976,079 A | 8/1976 | Samuels et al. |
| 4,014,492 A | 3/1977 | Rothfuss |
| 4,034,473 A | 7/1977 | May |
| 4,042,979 A | 8/1977 | Angell |
| 4,043,504 A | 8/1977 | Hueil et al. |
| 4,053,979 A | 10/1977 | Tuthill et al. |
| 4,055,861 A | 11/1977 | Carpentier et al. |
| 4,069,825 A | 1/1978 | Akiyama |
| 4,290,151 A | 9/1981 | Massana |
| 4,384,406 A | 5/1983 | Tischlinger |
| 4,445,892 A | 5/1984 | Hussein et al. |
| 4,489,446 A | 12/1984 | Reed |
| 4,494,542 A | 1/1985 | Lee |
| 4,510,934 A | 4/1985 | Batra |
| 4,549,545 A | 10/1985 | Levy |
| 4,619,247 A | 10/1986 | Inoue et al. |
| 4,700,250 A | 10/1987 | Kuriyama |
| 4,705,040 A | 11/1987 | Mueller et al. |
| 4,726,371 A | 2/1988 | Gibbens |
| 4,758,221 A | 7/1988 | Jureidini |
| 4,784,133 A | 11/1988 | Mackin |
| 4,845,851 A | 7/1989 | Warthen |
| 4,848,341 A | 7/1989 | Ahmad |
| 4,850,354 A | 7/1989 | McGurk-Burleson et al. |
| 4,961,738 A | 10/1990 | Mackin |
| 4,969,893 A | 11/1990 | Swor |
| 4,976,710 A | 12/1990 | Mackin |
| 5,035,701 A | 7/1991 | Kabbara |
| 5,053,047 A | 10/1991 | Yoon |
| 5,064,431 A | 11/1991 | Gilbertson et al. |
| 5,078,731 A * | 1/1992 | Hayhurst ................ 606/232 |
| 5,084,058 A | 1/1992 | Li |
| 5,103,804 A | 4/1992 | Abele et al. |
| 5,133,723 A | 7/1992 | Li et al. |
| RE34,021 E | 8/1992 | Mueller et al. |
| 5,221,255 A | 6/1993 | Mahurkar et al. |
| 5,221,269 A | 6/1993 | Miller et al. |
| 5,242,456 A | 9/1993 | Nash et al. |
| 5,242,457 A | 9/1993 | Akopov et al. |
| 5,257,975 A | 11/1993 | Foshee |
| 5,282,832 A | 2/1994 | Toso et al. |
| 5,312,341 A | 5/1994 | Turi |
| 5,324,298 A | 6/1994 | Phillips et al. |
| 5,346,500 A | 9/1994 | Suchart |
| 5,358,479 A | 10/1994 | Wilson |
| 5,358,514 A | 10/1994 | Schulman et al. |
| 5,364,407 A | 11/1994 | Poll |
| 5,366,479 A | 11/1994 | McGarry et al. |
| 5,368,591 A | 11/1994 | Lennox et al. |
| 5,383,905 A | 1/1995 | Golds et al. |
| 5,409,483 A | 4/1995 | Campbell et al. |
| 5,409,499 A * | 4/1995 | Yi ................ 606/151 |
| 5,417,700 A | 5/1995 | Egan |
| 5,423,837 A | 6/1995 | Mericle et al. |
| 5,431,659 A | 7/1995 | Ross, Jr. et al. |
| 5,437,680 A | 8/1995 | Yoon |
| 5,439,470 A | 8/1995 | Li |
| 5,450,860 A | 9/1995 | O'Connor |
| 5,452,513 A | 9/1995 | Zinnbauer et al. |
| 5,474,572 A | 12/1995 | Hayhurst |
| 5,520,702 A | 5/1996 | Sauer et al. |
| 5,522,873 A | 6/1996 | Jackman et al. |
| 5,524,630 A | 6/1996 | Crowley |
| 5,527,323 A | 6/1996 | Jervis et al. |
| 5,531,686 A | 7/1996 | Lundquist et al. |
| 5,531,763 A | 7/1996 | Mastri et al. |
| 5,545,134 A | 8/1996 | Hilaire et al. |
| 5,545,168 A | 8/1996 | Burke |
| 5,565,122 A | 10/1996 | Zinnbauer et al. |
| 5,571,215 A | 11/1996 | Sterman et al. |
| 5,584,835 A | 12/1996 | Greenfield |
| 5,591,194 A | 1/1997 | Berthiaume |
| 5,626,614 A | 5/1997 | Hart |
| 5,630,824 A | 5/1997 | Hart |
| 5,643,289 A | 7/1997 | Sauer et al. |
| 5,665,109 A | 9/1997 | Yoon |
| 5,669,917 A | 9/1997 | Sauer et al. |
| 5,674,279 A | 10/1997 | Wright et al. |
| 5,690,655 A | 11/1997 | Hart et al. |
| 5,702,397 A | 12/1997 | Goble et al. |
| 5,709,695 A | 1/1998 | Northrup, III |
| 5,716,370 A | 2/1998 | Williamson, IV et al. |
| 5,718,725 A | 2/1998 | Sterman et al. |
| 5,725,542 A | 3/1998 | Yoon |
| 5,733,308 A | 3/1998 | Daugherty et al. |
| 5,735,290 A | 4/1998 | Sterman et al. |
| 5,741,260 A | 4/1998 | Songer et al. |
| 5,741,301 A | 4/1998 | Pagedas |
| 5,752,518 A | 5/1998 | McGee et al. |
| 5,752,964 A | 5/1998 | Mericle |
| 5,752,966 A | 5/1998 | Chang |
| 5,755,730 A | 5/1998 | Swain et al. |
| 5,766,240 A | 6/1998 | Johnson |
| 5,769,812 A | 6/1998 | Stevens et al. |
| 5,782,861 A | 7/1998 | Cragg et al. |
| 5,810,848 A | 9/1998 | Hayhurst |
| 5,810,853 A | 9/1998 | Yoon |
| 5,817,107 A | 10/1998 | Schaller |
| 5,827,171 A | 10/1998 | Dobak, III et al. |
| 5,843,169 A | 12/1998 | Taheri |
| 5,848,969 A | 12/1998 | Panescu et al. |
| 5,860,992 A | 1/1999 | Daniel et al. |
| 5,860,993 A | 1/1999 | Thompson et al. |
| 5,861,003 A | 1/1999 | Latson et al. |
| 5,868,733 A | 2/1999 | Ockuly et al. |
| 5,879,371 A | 3/1999 | Gardiner et al. |
| 5,885,238 A | 3/1999 | Stevens et al. |
| 5,888,240 A | 3/1999 | Carpentier et al. |
| 5,902,321 A | 5/1999 | Caspari et al. |
| 5,904,651 A | 5/1999 | Swanson et al. |
| 5,919,208 A | 7/1999 | Valenti |
| 5,935,149 A | 8/1999 | Ek |
| 5,947,983 A | 9/1999 | Solar et al. |
| 5,961,440 A | 10/1999 | Schweich, Jr. et al. |
| 5,961,539 A | 10/1999 | Northrup, III et al. |
| 5,972,004 A | 10/1999 | Williamson, IV et al. |
| 5,989,284 A | 11/1999 | Laufer |
| 5,991,650 A | 11/1999 | Swanson et al. |
| 6,010,531 A | 1/2000 | Donlon et al. |
| 6,015,428 A | 1/2000 | Pagedas |
| 6,045,497 A | 4/2000 | Schweich, Jr. et al. |
| 6,050,936 A | 4/2000 | Schweich, Jr. et al. |
| 6,066,160 A | 5/2000 | Colvin et al. |
| 6,074,401 A | 6/2000 | Gardiner et al. |
| 6,077,214 A | 6/2000 | Mortier et al. |
| 6,077,989 A | 6/2000 | Kandel et al. |
| 6,080,182 A | 6/2000 | Shaw et al. |
| 6,086,608 A | 7/2000 | Ek et al. |
| 6,099,553 A | 8/2000 | Hart et al. |
| 6,125,852 A | 10/2000 | Stevens et al. |
| 6,149,658 A | 11/2000 | Gardiner et al. |
| 6,152,934 A | 11/2000 | Harper et al. |
| 6,162,168 A | 12/2000 | Schweich, Jr. et al. |
| 6,165,183 A | 12/2000 | Kuehn et al. |
| 6,171,317 B1 | 1/2001 | Jackson et al. |
| 6,171,329 B1 | 1/2001 | Shaw et al. |
| 6,183,469 B1 | 2/2001 | Thapliyal et al. |
| 6,197,017 B1 | 3/2001 | Brock et al. |
| 6,200,329 B1 | 3/2001 | Fung et al. |
| 6,221,084 B1 | 4/2001 | Fleenor |
| 6,228,096 B1 | 5/2001 | Marchand |
| 6,250,308 B1 | 6/2001 | Cox |
| 6,254,620 B1 | 7/2001 | Koh et al. |
| 6,258,118 B1 | 7/2001 | Baum et al. |
| 6,260,552 B1 | 7/2001 | Mortier et al. |
| 6,269,819 B1 | 8/2001 | Oz et al. |
| 6,283,993 B1 | 9/2001 | Cosgrove et al. |
| 6,306,149 B1 | 10/2001 | Meade |
| 6,312,447 B1 | 11/2001 | Grimes |
| 6,328,727 B1 | 12/2001 | Frazier et al. |
| 6,332,893 B1 | 12/2001 | Mortier et al. |
| 6,355,030 B1 | 3/2002 | Aldrich et al. |
| 6,378,289 B1 | 4/2002 | Trudeau et al. |

| | | |
|---|---|---|
| 6,391,048 B1 | 5/2002 | Ginn et al. |
| 6,409,743 B1 | 6/2002 | Fenton, Jr. |
| 6,423,088 B1 | 7/2002 | Fenton, Jr. |
| 6,432,123 B2 | 8/2002 | Schwartz et al. |
| 6,461,327 B1 | 10/2002 | Addis et al. |
| 6,514,265 B2 | 2/2003 | Ho et al. |
| 6,524,328 B2 | 2/2003 | Levinson |
| 6,524,338 B1 | 2/2003 | Gundry |
| 6,533,753 B1 | 3/2003 | Haarstad et al. |
| 6,551,332 B1 | 4/2003 | Nguyen et al. |
| 6,575,971 B2 | 6/2003 | Hauck et al. |
| 6,602,288 B1 | 8/2003 | Cosgrove et al. |
| 6,602,289 B1 | 8/2003 | Colvin et al. |
| 6,607,541 B1 | 8/2003 | Gardiner et al. |
| 6,613,059 B2 | 9/2003 | Schaller et al. |
| 6,616,667 B1 | 9/2003 | Steiger et al. |
| 6,619,291 B2 | 9/2003 | Hlavka et al. |
| 6,626,899 B2 | 9/2003 | Houser et al. |
| 6,629,534 B1 | 10/2003 | Goar et al. |
| 6,641,593 B1 | 11/2003 | Schaller et al. |
| 6,648,903 B1 | 11/2003 | Pierson, III |
| 6,651,671 B1 | 11/2003 | Donlon et al. |
| 6,652,562 B2 | 11/2003 | Collier et al. |
| 6,655,386 B1 | 12/2003 | Makower et al. |
| 6,669,687 B1 | 12/2003 | Saadat |
| 6,676,702 B2 | 1/2004 | Mathis |
| 6,689,164 B1 | 2/2004 | Seguin |
| 6,699,263 B2 | 3/2004 | Cope |
| 6,702,826 B2 | 3/2004 | Liddicoat et al. |
| 6,716,243 B1 | 4/2004 | Colvin et al. |
| 6,718,985 B2 | 4/2004 | Hlavka et al. |
| 6,723,107 B1 | 4/2004 | Skiba et al. |
| 6,733,509 B2 | 5/2004 | Nobles et al. |
| 6,752,813 B2 | 6/2004 | Goldfarb et al. |
| 6,790,231 B2 | 9/2004 | Liddicoat et al. |
| 6,793,618 B2 | 9/2004 | Schweich, Jr. et al. |
| 6,802,851 B2 | 10/2004 | Jones et al. |
| 6,908,424 B2 | 6/2005 | Mortier et al. |
| 6,923,818 B2 | 8/2005 | Muramatsu et al. |
| 6,932,792 B1 | 8/2005 | St. Goar et al. |
| 6,986,775 B2 | 1/2006 | Morales et al. |
| 6,991,643 B2 | 1/2006 | Saadat |
| 6,997,931 B2 | 2/2006 | Sauer et al. |
| 7,004,958 B2 | 2/2006 | Adams et al. |
| 7,037,334 B1 | 5/2006 | Hlavka et al. |
| 7,044,957 B2 | 5/2006 | Foerster et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,166,127 B2 | 1/2007 | Spence et al. |
| 7,186,262 B2 | 3/2007 | Saadat |
| 7,189,199 B2 | 3/2007 | McCarthy et al. |
| 7,235,086 B2 | 6/2007 | Sauer et al. |
| 7,241,310 B2 | 7/2007 | Taylor et al. |
| 7,344,544 B2 | 3/2008 | Bender et al. |
| 7,374,530 B2 | 5/2008 | Schaller |
| 7,381,210 B2 | 6/2008 | Zarbatany et al. |
| 7,390,329 B2 | 6/2008 | Westra et al. |
| 7,452,325 B2 | 11/2008 | Schaller |
| 7,588,582 B2 | 9/2009 | Starksen et al. |
| 7,618,449 B2 | 11/2009 | Tremulis et al. |
| 7,666,193 B2 | 2/2010 | Starksen et al. |
| 7,699,892 B2 | 4/2010 | Rafiee et al. |
| 7,727,247 B2 * | 6/2010 | Kimura et al. ............... 606/157 |
| 7,753,922 B2 | 7/2010 | Starksen |
| 7,758,637 B2 | 7/2010 | Starksen et al. |
| 7,922,762 B2 | 4/2011 | Starksen |
| 2001/0005787 A1 | 6/2001 | Oz et al. |
| 2001/0014800 A1 | 8/2001 | Frazier et al. |
| 2001/0023332 A1 | 9/2001 | Hahnen |
| 2001/0031979 A1 | 10/2001 | Ricci |
| 2001/0041821 A1 | 11/2001 | Wilk |
| 2002/0013621 A1 | 1/2002 | Stobie et al. |
| 2002/0026201 A1 | 2/2002 | Foerster et al. |
| 2002/0029080 A1 | 3/2002 | Mortier et al. |
| 2002/0035361 A1 | 3/2002 | Houser et al. |
| 2002/0042621 A1 | 4/2002 | Liddicoat et al. |
| 2002/0065536 A1 | 5/2002 | Hart et al. |
| 2002/0072757 A1 | 6/2002 | Ahmed et al. |
| 2002/0087048 A1 | 7/2002 | Brock et al. |
| 2002/0087049 A1 | 7/2002 | Brock et al. |
| 2002/0087148 A1 | 7/2002 | Brock et al. |
| 2002/0087169 A1 | 7/2002 | Brock et al. |
| 2002/0095167 A1 | 7/2002 | Liddicoat et al. |
| 2002/0095175 A1 * | 7/2002 | Brock et al. ............... 606/205 |
| 2002/0095180 A1 | 7/2002 | West, Jr. et al. |
| 2002/0116012 A1 | 8/2002 | May et al. |
| 2002/0138044 A1 | 9/2002 | Streeter et al. |
| 2002/0156526 A1 | 10/2002 | Hlavka et al. |
| 2002/0161378 A1 | 10/2002 | Downing |
| 2002/0165486 A1 | 11/2002 | Bertolero et al. |
| 2002/0173841 A1 | 11/2002 | Ortiz et al. |
| 2002/0193815 A1 | 12/2002 | Foerster et al. |
| 2003/0009196 A1 | 1/2003 | Peterson |
| 2003/0018358 A1 | 1/2003 | Saadat |
| 2003/0032979 A1 | 2/2003 | Mortier et al. |
| 2003/0033006 A1 | 2/2003 | Phillips et al. |
| 2003/0060813 A1 | 3/2003 | Loeb et al. |
| 2003/0069593 A1 | 4/2003 | Tremulis et al. |
| 2003/0074012 A1 | 4/2003 | Nguyen et al. |
| 2003/0078465 A1 | 4/2003 | Pai et al. |
| 2003/0078603 A1 | 4/2003 | Schaller et al. |
| 2003/0093118 A1 | 5/2003 | Ho et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |
| 2003/0130731 A1 | 7/2003 | Vidlund et al. |
| 2003/0144697 A1 | 7/2003 | Mathis et al. |
| 2003/0158464 A1 | 8/2003 | Bertolero |
| 2003/0158581 A1 | 8/2003 | Levinson |
| 2003/0167062 A1 | 9/2003 | Gambale et al. |
| 2003/0167071 A1 | 9/2003 | Martin et al. |
| 2003/0181800 A1 | 9/2003 | Bonutti |
| 2003/0191497 A1 | 10/2003 | Cope |
| 2003/0195562 A1 | 10/2003 | Collier et al. |
| 2003/0199974 A1 | 10/2003 | Lee et al. |
| 2003/0204205 A1 | 10/2003 | Sauer et al. |
| 2003/0220659 A1 | 11/2003 | Schmieding et al. |
| 2003/0220685 A1 | 11/2003 | Hlavka et al. |
| 2003/0225420 A1 | 12/2003 | Wardle |
| 2003/0229361 A1 | 12/2003 | Jackson |
| 2003/0233105 A1 | 12/2003 | Gayton |
| 2003/0233142 A1 | 12/2003 | Morales et al. |
| 2003/0236535 A1 | 12/2003 | Onuki et al. |
| 2004/0003819 A1 | 1/2004 | St. Goar et al. |
| 2004/0019378 A1 | 1/2004 | Hlavka et al. |
| 2004/0030382 A1 | 2/2004 | St. Goar et al. |
| 2004/0039442 A1 | 2/2004 | St. Goar et al. |
| 2004/0044365 A1 | 3/2004 | Bachman |
| 2004/0092962 A1 | 5/2004 | Thornton et al. |
| 2004/0093023 A1 | 5/2004 | Allen et al. |
| 2004/0093024 A1 | 5/2004 | Lousararian et al. |
| 2004/0097788 A1 | 5/2004 | Mourlas et al. |
| 2004/0122450 A1 | 6/2004 | Oren et al. |
| 2004/0133274 A1 | 7/2004 | Webler et al. |
| 2004/0148020 A1 | 7/2004 | Vidlund et al. |
| 2004/0172046 A1 | 9/2004 | Hlavka et al. |
| 2004/0181238 A1 | 9/2004 | Zarbatany et al. |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0225300 A1 | 11/2004 | Goldfarb et al. |
| 2004/0236354 A1 | 11/2004 | Seguin |
| 2004/0236372 A1 | 11/2004 | Anspach, III et al. |
| 2004/0236419 A1 | 11/2004 | Milo |
| 2004/0243227 A1 | 12/2004 | Starksen et al. |
| 2005/0021054 A1 | 1/2005 | Ainsworth et al. |
| 2005/0033325 A1 | 2/2005 | May et al. |
| 2005/0055052 A1 | 3/2005 | Lombardo et al. |
| 2005/0055087 A1 | 3/2005 | Starksen |
| 2005/0065550 A1 | 3/2005 | Starksen et al. |
| 2005/0080454 A1 | 4/2005 | Drews et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119673 A1 | 6/2005 | Gordon et al. |

| | | | | | | |
|---|---|---|---|---|---|---|
| 2005/0119735 | A1 | 6/2005 | Spence et al. | 2009/0292353 A1 | 11/2009 | Yoganathan et al. |
| 2005/0125011 | A1 | 6/2005 | Spence et al. | 2010/0049213 A1 | 2/2010 | Serina et al. |
| 2005/0137689 | A1 | 6/2005 | Salahieh et al. | 2010/0082098 A1 | 4/2010 | Starksen et al. |
| 2005/0143762 | A1 | 6/2005 | Paraschac et al. | 2010/0094314 A1 | 4/2010 | Hernlund et al. |
| 2005/0165424 | A1 | 7/2005 | Gallagher et al. | 2010/0121349 A1 | 5/2010 | Meier et al. |
| 2005/0184122 | A1 | 8/2005 | Hlavka et al. | | | |
| 2005/0192599 | A1 | 9/2005 | Demarais | FOREIGN PATENT DOCUMENTS | | |
| 2005/0192629 | A1 | 9/2005 | Saadat et al. | JP 6-510460 A | 11/1994 | |
| 2005/0197694 | A1 | 9/2005 | Pai et al. | JP 11-506628 A | 6/1999 | |
| 2005/0209690 | A1 | 9/2005 | Mathis et al. | WO WO-93/08740 A1 | 5/1993 | |
| 2005/0216078 | A1 | 9/2005 | Starksen et al. | WO WO-94/03227 A1 | 2/1994 | |
| 2005/0228452 | A1 | 10/2005 | Mourlas et al. | WO WO-95/15715 A1 | 6/1995 | |
| 2005/0251157 | A1 | 11/2005 | Saadat et al. | WO WO-96/08208 A1 | 3/1996 | |
| 2005/0251159 | A1 | 11/2005 | Ewers et al. | WO WO-96/39081 A1 | 12/1996 | |
| 2005/0251166 | A1 | 11/2005 | Vaughan et al. | WO WO-96/39942 A1 | 12/1996 | |
| 2005/0251177 | A1 | 11/2005 | Saadat et al. | WO WO-97/27799 A1 | 8/1997 | |
| 2005/0251205 | A1 | 11/2005 | Ewers et al. | WO WO-97/27807 A1 | 8/1997 | |
| 2005/0251207 | A1 | 11/2005 | Flores et al. | WO WO-97/30639 A1 | 8/1997 | |
| 2005/0251208 | A1 | 11/2005 | Elmer et al. | WO WO-98/07375 A1 | 2/1998 | |
| 2005/0251209 | A1 | 11/2005 | Saadat et al. | WO WO-00/60995 A2 | 10/2000 | |
| 2005/0251210 | A1 | 11/2005 | Westra et al. | WO WO-00/60995 A3 | 10/2000 | |
| 2005/0267495 | A1 | 12/2005 | Ginn et al. | WO WO-00/67640 A2 | 11/2000 | |
| 2005/0273138 | A1 | 12/2005 | To et al. | WO WO-00/67640 A3 | 11/2000 | |
| 2005/0277966 | A1 | 12/2005 | Ewers et al. | WO WO-01/26586 A1 | 4/2001 | |
| 2005/0277981 | A1 | 12/2005 | Maahs et al. | WO WO-01/54618 A1 | 8/2001 | |
| 2005/0277983 | A1 | 12/2005 | Saadat et al. | WO WO-02/03892 A1 | 1/2002 | |
| 2006/0015144 | A1 | 1/2006 | Burbank et al. | WO WO-02/051329 A1 | 7/2002 | |
| 2006/0025750 | A1 | 2/2006 | Starksen et al. | WO WO-02/074178 A2 | 9/2002 | |
| 2006/0025784 | A1 | 2/2006 | Starksen et al. | WO WO-02/074178 A3 | 9/2002 | |
| 2006/0025787 | A1 | 2/2006 | Morales et al. | WO WO-02/085251 A1 | 10/2002 | |
| 2006/0058817 | A1 | 3/2006 | Starksen et al. | WO WO-02/085252 A1 | 10/2002 | |
| 2006/0069429 | A1 | 3/2006 | Spence et al. | WO WO-03/049648 A2 | 6/2003 | |
| 2006/0106422 | A1 | 5/2006 | Del Rio et al. | WO WO-03/049648 A3 | 6/2003 | |
| 2006/0122633 | A1 | 6/2006 | To et al. | WO WO-03/073913 A2 | 9/2003 | |
| 2006/0129188 | A1 | 6/2006 | Starksen et al. | WO WO-03/088875 A1 | 10/2003 | |
| 2006/0178682 | A1 | 8/2006 | Boehlke | WO WO-03/105667 A2 | 12/2003 | |
| 2006/0184203 | A1 | 8/2006 | Martin et al. | WO WO-03/105667 A3 | 12/2003 | |
| 2006/0190030 | A1 | 8/2006 | To et al. | WO WO-03/105670 A2 | 12/2003 | |
| 2006/0200199 | A1 | 9/2006 | Bonutti et al. | WO WO-03/105670 A3 | 12/2003 | |
| 2006/0235413 | A1 | 10/2006 | Denham et al. | WO WO-2004/037317 A2 | 5/2004 | |
| 2006/0241656 | A1 | 10/2006 | Starksen et al. | WO WO-2004/045367 A2 | 6/2004 | |
| 2006/0264975 | A1 | 11/2006 | Pipenhagen et al. | WO WO-2004/045367 A3 | 6/2004 | |
| 2006/0265010 | A1 | 11/2006 | Paraschac et al. | WO WO-2004/082523 A2 | 9/2004 | |
| 2006/0271101 | A1 | 11/2006 | Saadat et al. | WO WO-2004/082538 A2 | 9/2004 | |
| 2006/0287661 | A1 | 12/2006 | Bolduc et al. | WO WO-2005/025644 A2 | 3/2005 | |
| 2007/0005081 | A1 | 1/2007 | Findlay, III et al. | WO WO-2005/025644 A3 | 3/2005 | |
| 2007/0005394 | A1 | 1/2007 | Bleyendaal et al. | WO WO-2005/062931 A2 | 7/2005 | |
| 2007/0010852 | A1 | 1/2007 | Blaeser et al. | WO WO-2005/102181 A1 | 11/2005 | |
| 2007/0010857 | A1 | 1/2007 | Sugimoto et al. | WO WO-2005/110241 A1 | 11/2005 | |
| 2007/0016250 | A1 | 1/2007 | Blaeser et al. | WO WO-2006/034243 A2 | 3/2006 | |
| 2007/0032820 | A1 | 2/2007 | Chin-Chen et al. | WO WO-2006/037073 A2 | 4/2006 | |
| 2007/0038293 | A1 | 2/2007 | St.Goar et al. | WO WO-2006/039296 A2 | 4/2006 | |
| 2007/0049942 | A1 | 3/2007 | Hindrichs et al. | WO WO-2006/097931 A2 | 9/2006 | |
| 2007/0051377 | A1 | 3/2007 | Douk et al. | WO WO-2006/116558 A2 | 11/2006 | |
| 2007/0055206 | A1 | 3/2007 | To et al. | WO WO-2006/128092 A2 | 11/2006 | |
| 2007/0066994 | A1 | 3/2007 | Blaeser et al. | WO WO-2006/128092 A3 | 11/2006 | |
| 2007/0106310 | A1 | 5/2007 | Goldin et al. | WO WO-2007/001936 A2 | 1/2007 | |
| 2007/0112424 | A1 | 5/2007 | Spence et al. | WO WO-2007/001936 A3 | 1/2007 | |
| 2007/0112425 | A1 | 5/2007 | Schaller et al. | WO WO-2007/005495 A1 | 1/2007 | |
| 2007/0156172 | A1 | 7/2007 | Alvarado | WO WO-2007/021564 A1 | 2/2007 | |
| 2007/0213746 | A1 | 9/2007 | Hahn et al. | WO WO-2007/021834 A1 | 2/2007 | |
| 2007/0276437 | A1 | 11/2007 | Call et al. | WO WO-2007/035449 A2 | 3/2007 | |
| 2008/0045977 | A1 | 2/2008 | To et al. | WO WO-2007/056502 A1 | 5/2007 | |
| 2008/0045982 | A1 | 2/2008 | To et al. | WO WO-2007/100409 A2 | 9/2007 | |
| 2008/0045983 | A1 | 2/2008 | To et al. | WO WO-2008/028135 A2 | 3/2008 | |
| 2008/0051810 | A1 | 2/2008 | To et al. | WO WO-2008/028135 A3 | 3/2008 | |
| 2008/0051832 | A1 | 2/2008 | To et al. | WO WO-2008/112740 A2 | 9/2008 | |
| 2008/0058868 | A1 | 3/2008 | To et al. | WO WO-2008/112740 A3 | 9/2008 | |
| 2008/0065156 | A1 | 3/2008 | Hauser et al. | WO WO-2009/061611 A1 | 5/2009 | |
| 2008/0097484 | A1 | 4/2008 | Lim et al. | | | |
| 2008/0177304 | A1 | 7/2008 | Westra et al. | OTHER PUBLICATIONS | | |
| 2008/0234728 | A1 | 9/2008 | Starksen et al. | | | |
| 2008/0234815 | A1 | 9/2008 | Starksen | De Simone, R. et al. (Apr. 1, 1994). "Adjustable Annuloplasty for | | |
| 2008/0294177 | A1 | 11/2008 | To et al. | Tricuspid Insufficiency with External Control," *Reader's Comments* | | |
| 2009/0093670 | A1 | 4/2009 | Annest et al. | *and Reply, Am. J. Cardiol.* 73(9):721-722. | | |
| 2009/0182417 | A1 | 7/2009 | Tremulis et al. | De Simone, R. et al. (Apr. 15, 1993). "Adjustable Tricuspid Valve | | |
| 2009/0222083 | A1 | 9/2009 | Nguyen et al. | Annuloplasty Assisted by Intraoperative Transesophageal Color | | |
| 2009/0234318 | A1 | 9/2009 | Loulmet et al. | Doppler Echocardiography," *Am. J. Cardiol.* 71(11):926-931. | | |
| 2009/0276038 | A1 | 11/2009 | Tremulis et al. | | | |

Downing, S.W. et al. (2002). "Feasibility of Off-Pump ASD Closure Using Real-Time 3-D Echocardiography," *The Heart Surgery Forum* 5(2):96-99, Abstract 7025.
International Search Report mailed Dec. 19, 2006, for PCT Application No. PCT/US2006/031190, filed Aug. 10, 2006, four pages.
International Search Report mailed on Apr. 2, 2007, for PCT Application No. PCT/US2006/043597, filed Nov. 8, 2006, seven pages.
Nagy, Z.L. et al. (Dec. 2000). "Mitral Annuloplasty with a Suture Technique," *European Journal of Cardio-thoracic Surgery* 18(6):739-740.
Shumway, S.J. et al. (Dec. 1988). "A 'Designer' Annuloplasty Ring for Patients with Massive Mitral annular Dilatation," *Ann. Thorac. Surg.* 46(6):695-696.
U.S. Appl. No. 11/656,141, filed Jan. 19, 2007, by Straksen et al.
U.S. Appl. No. 11/875,774, filed Oct. 19, 2007, by Serina et al.
U.S. Appl. No. 11/894,340, filed Aug. 20, 2007, by To et al.
U.S. Appl. No. 11/894,368, filed Aug. 20, 2007, by To et al.
U.S. Appl. No. 11/894,397, filed Aug. 20, 2007, by To et al.
U.S. Appl. No. 11/894,401, filed Aug. 20, 2007, by To et al.
U.S. Appl. No. 11/894,463, filed Aug. 20, 2007, by To et al.
U.S. Appl. No. 11/894,468, filed Aug. 20, 2007, by To et al.
U.S. Appl. No. 12/132,161, filed Jun. 3, 2008, by Starksen et al.
U.S. Appl. No. 12/132,375, filed Jun. 3, 2008, by Starksen et al.
Supplementary European Search Report mailed on Nov. 10, 2008, for EP Application No. 04 78 2847, filed on Sep. 1, 2004, 2 pages.
U.S. Appl. No. 12/187,331, filed Aug. 6, 2008, by To et al.
Final Office Action mailed on Jul. 21, 2009, for U.S. Appl. No. 11/270,034, filed Nov. 8, 2005, 8 pages.
Final Office Action mailed on Sep. 2, 2009, for U.S. Appl. No. 11/232,190, filed Sep. 20, 2005, 8 pages.
Final Office Action mailed on Sep. 28, 2009, for U.S. Appl. No. 11/202,474, filed Aug. 11, 2005, 10 pages.
Final Office Action mailed on Oct. 13, 2009, for U.S. Appl. No. 10/901,554, filed Jul. 27, 2004, 11 pages.
Final Office Action mailed on Nov. 10, 2009, for U.S. Appl. No. 10/741,130, filed Dec. 19, 2003, 9 pages.
Final Office Action mailed on Mar. 3, 2010, for U.S. Appl. No. 11/414,657, filed Apr. 27, 2006, 7 pages.
Final Office Action mailed on Mar. 25, 2010, for U.S. Appl. No. 10/900,980, filed Jul. 27, 2004, 8 pages.
Final Office Action mailed on Jun. 8, 2010, for U.S. Appl. No. 10/792,681, filed Mar. 2, 2004, 17 pages.
Final Office Action mailed on Jul. 26, 2010, for U.S. Appl. No. 11/270,034, filed Nov. 8, 2005, 8 pages.
Final Office Action mailed on Sep. 15, 2010, for U.S. Appl. No. 11/894,401, filed Aug. 20, 2007, 6 pages.
Final Office Action mailed on Oct. 6, 2010, for U.S. Appl. No. 12/132,375, filed Jun. 3, 2008, 9 pages.
Final Office Action mailed on Nov. 26, 2010, for U.S. Appl. No. 11/894,340, filed Aug. 20, 2007, 12 pages.
Final Office Action mailed on Nov. 29, 2010, for U.S. Appl. No. 11/894,463, filed Aug. 20, 2007, 12 pages.
Final Office Action mailed on Feb. 24, 2011, for U.S. Appl. No. 11/894,397, filed Aug. 20, 2007, 12 pages.
Final Office Action mailed on Feb. 24, 2011, for U.S. Appl. No. 11/894,468, filed Aug. 20, 2007, 12 pages.
Final Office Action mailed on Mar. 17, 2011, for U.S. Appl. No. 10/901,554, filed Jul. 27, 2004, 13 pages.
Final Office Action mailed on Mar. 17, 2011, for U.S. Appl. No. 11/202,474, filed Aug. 11, 2005, 9 pages.
Final Office Action mailed on Apr. 20, 2011, for U.S. Appl. No. 11/414,657, filed Apr. 27, 2006, 8 pages.
Non-Final Office Action mailed on Aug. 25, 2009, for U.S. Appl. No. 10/900,980, filed Jul. 27, 2004, 7 pages.
Non-Final Office Action mailed on Aug. 26, 2009, for U.S. Appl. No. 11/414,657, filed Apr. 27, 2006, 6 pages.
Non-Final Office Action mailed on Sep. 17, 2009, for U.S. Appl. No. 10/656,797, filed Sep. 4, 2003, 13 pages.
Non-Final Office Action mailed on Oct. 19, 2009, for U.S. Appl. No. 10/901,019, filed Jul. 27, 2004, 21 pages.
Non-Final Office Action mailed on Jan. 19, 2010, for U.S. Appl. No. 11/270,034, filed Nov. 8, 2005, 10 pages.
Non-Final Office Action mailed on Feb. 18, 2010, for U.S. Appl. No. 11/894,401, filed Aug. 20, 2007, 6 pages.
Non-Final Office Action mailed on Mar. 16, 2010, for U.S. Appl. No. 11/894,340, filed Aug. 20, 2007, 14 pages.
Non-Final Office Action mailed on Mar. 29, 2010, for U.S. Appl. No. 11/894,463, filed Aug. 20, 2007, 14 pages.
Non-Final Office Action mailed on Apr. 2, 2010, for U.S. Appl. No. 12/132,375, filed Jun. 3, 2008, 9 pages.
Non-Final Office Action mailed on Jun. 9, 2010, for U.S. Appl. No. 11/894,468, filed Aug. 20, 2007, 14 pages.
Non-Final Office Action mailed on Jun. 21, 2010, for U.S. Appl. No. 11/894,397, filed Aug. 20, 2007, 13 pages.
Non-Final Office Action mailed on Aug. 17, 2010, for U.S. Appl. No. 11/414,657, filed Apr. 27, 2006, 7 pages.
Non-Final Office Action mailed on Aug. 20, 2010, for U.S. Appl. No. 10/901,554, filed Jul. 27, 2004, 13 pages.
Non-Final Office Action mailed on Oct. 8, 2010, for U.S. Appl. No. 11/894,368, filed Aug. 20, 2007, 10 pages.
Non-Final Office Action mailed on Oct. 25, 2010, for U.S. Appl. No. 11/202,474, filed Aug. 11, 2005, 8 pages.
Non-Final Office Action mailed on Nov. 24, 2010, for U.S. Appl. No. 10/900,980, filed Jul. 27, 2004, 8 pages.
Non-Final Office Action mailed on Feb. 2, 2011, for U.S. Appl. No. 12/581,040, filed Oct. 16, 2009, 5 pages.
Non-Final Office Action mailed on Feb. 11, 2011, for U.S. Appl. No. 12/132,328, filed Jun. 3, 2008, 9 pages.
Notice of Allowance mailed on Aug. 4, 2009, for U.S. Appl. No. 10/901,555, filed Jul. 27, 2004, 7 pages.
Notice of Allowance mailed on Feb. 24, 2010, for U.S. Appl. No. 10/656,797, filed Sep. 4, 2003, 8 pages.
Notice of Allowance mailed on Apr. 28, 2010, for U.S. Appl. No. 10/901,019, filed Jul. 27, 2004, 7 pages.
Notice of Allowance mailed on Nov. 17, 2010, for U.S. Appl. No. 11/232,190, filed Sep. 20, 2005, 11 pages.
Notice of Allowance mailed on Dec. 6, 2010, for U.S. Appl. No. 12/132,375, filed Jun. 3, 2008, 9 pages.
U.S. Appl. No. 12/850,531, filed Aug. 4, 2010, by Starksen et al.
U.S. Appl. No. 13/042,369, filed Mar. 7, 2011, by Starksen et al.

* cited by examiner

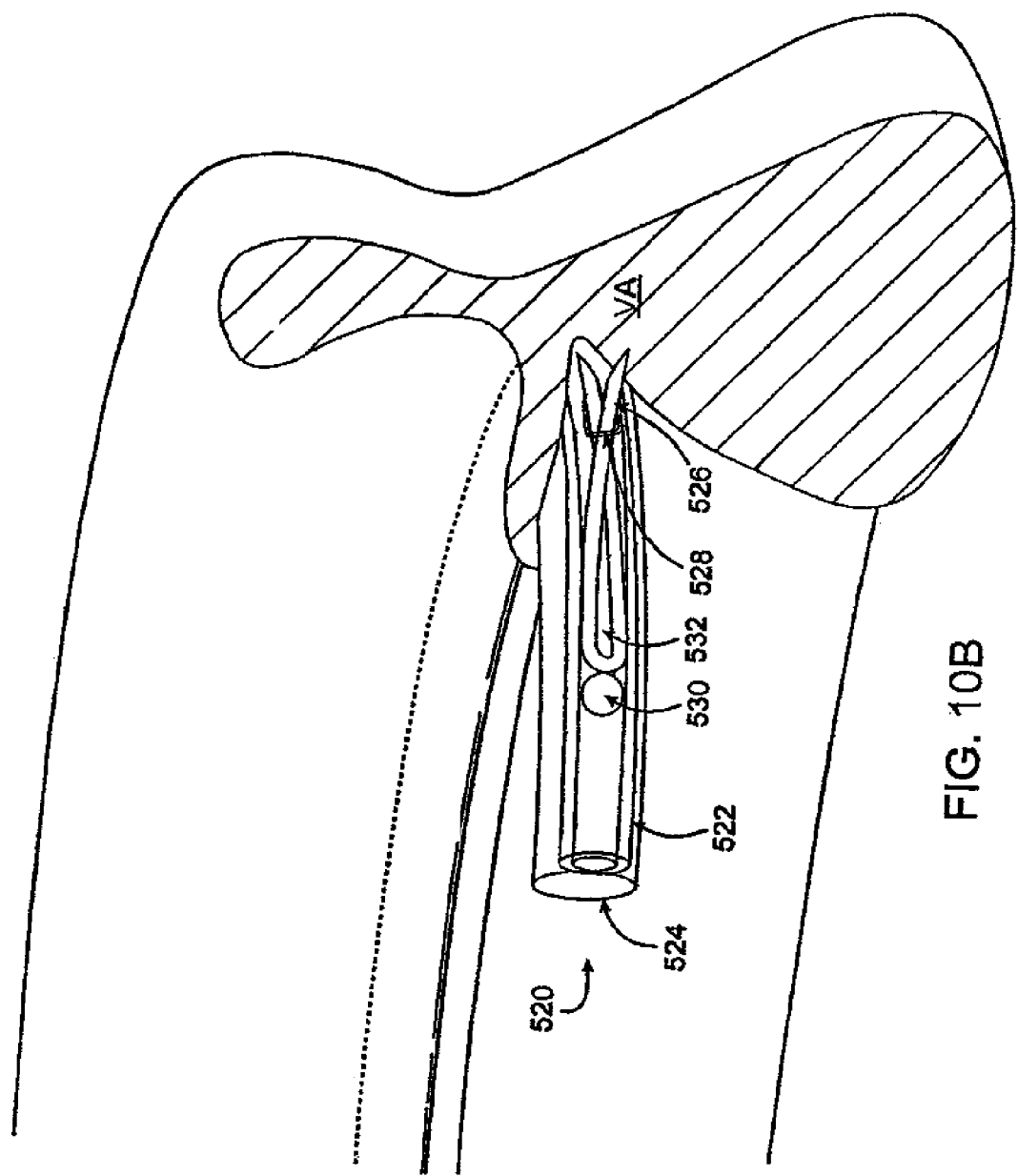

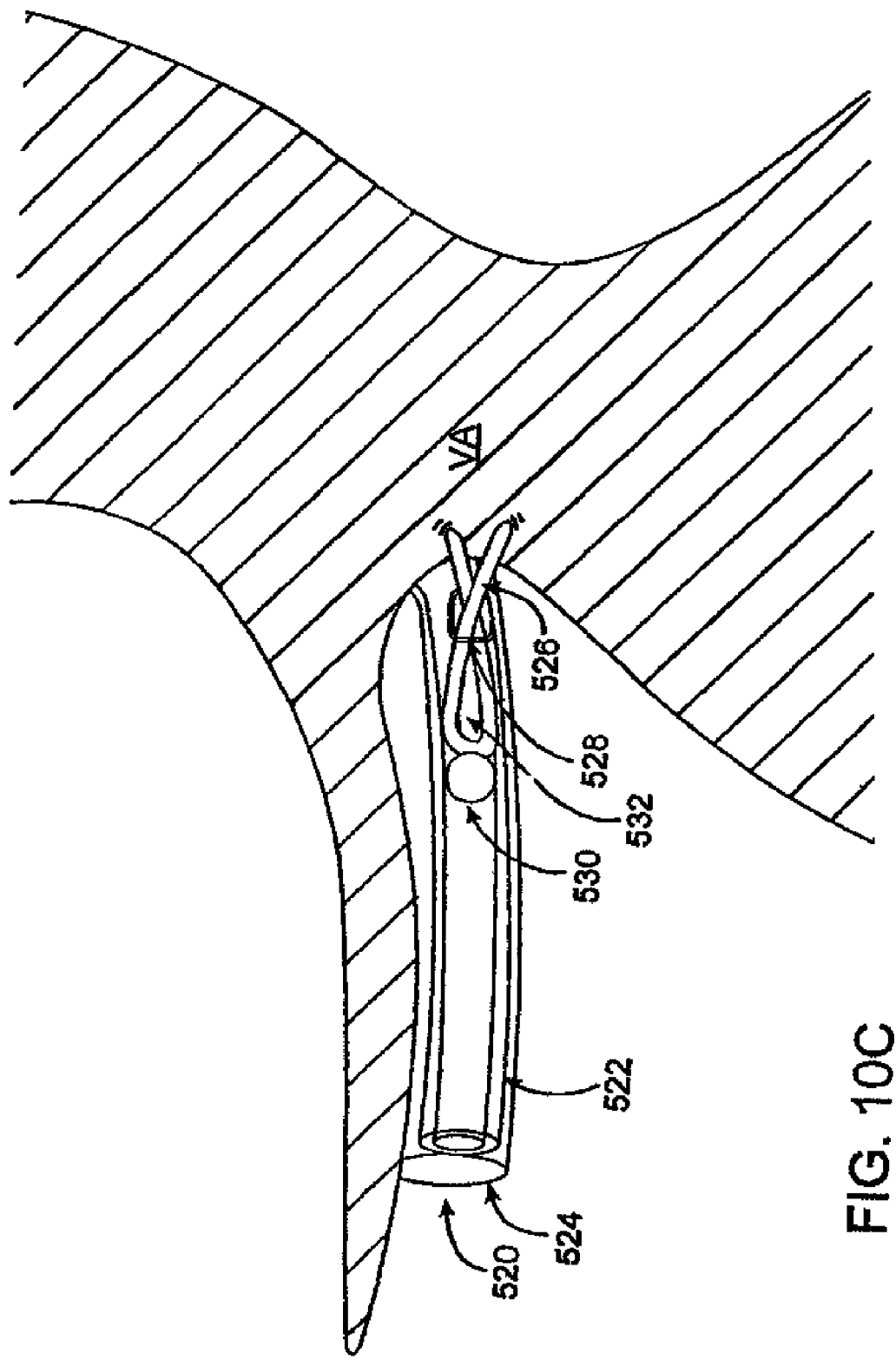

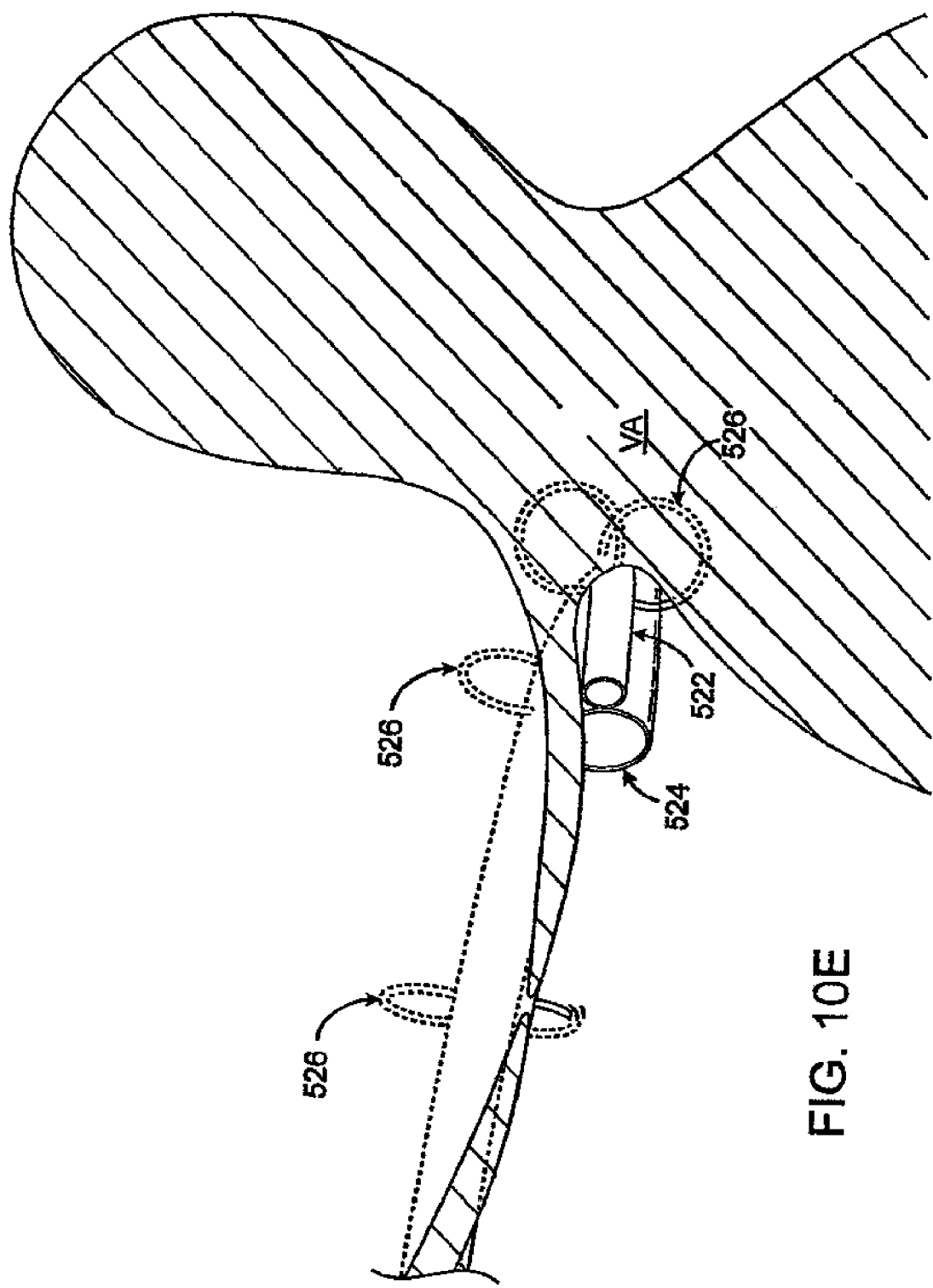

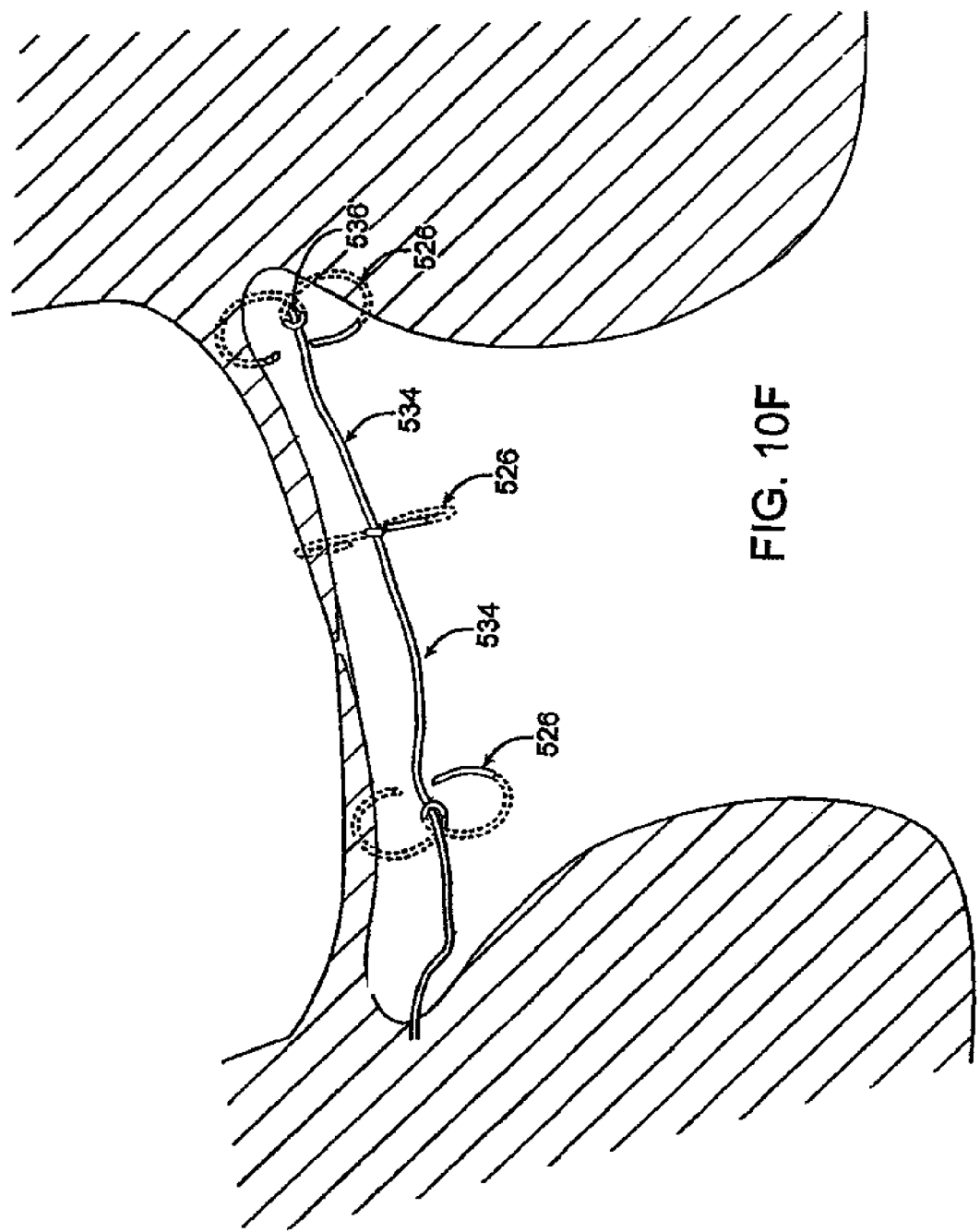

METHODS AND DEVICES FOR TERMINATION

CROSS-REFERENCE TO RELATED APPLICATIONS

This application is a continuation application, under 35 U.S.C. §120, of U.S. Ser. No. 11/270,034, filed Nov. 8, 2005, which is a continuation-in-part of U.S. Ser. No. 11/232,190, filed Sep. 20, 2005, which is a continuation-in-part of U.S. Ser. No. 10/792,681, filed Mar. 2, 2004, which claims the benefit of U.S. Ser. No. 60/459,735, filed on Apr. 1, 2003, U.S. Ser. No. 60/462,502, filed on Apr. 10, 2003, and U.S. Ser. No. 60/524,922, filed on Nov. 24, 2003, and which is a continuation-in-part of U.S. Ser. No. 10/741,130, filed on Dec. 19, 2003, which is a continuation-in-part of U.S. Ser. No. 10/656,797, filed on Sep. 4, 2003, and is a continuation-in-part of U.S. Ser. No. 10/461,043, filed on Jun. 13, 2003, the latter of which claims the benefit of U.S. Ser. No. 60/388,935, filed on Jun. 13, 2002, U.S. Ser. No. 60/429,288, filed on Nov. 25, 2002, U.S. Ser. No. 60/445,890, filed on Feb. 6, 2003, and U.S. Ser. No. 60/462,502, filed on Apr. 10, 2003, the disclosures of which are herein incorporated by reference in their entirety.

FIELD

The methods and devices described herein relate generally to medical devices and methods, and more specifically to devices and methods for enhancing tissue repair using minimally invasive surgical techniques, especially for use in cardiovascular valve repair.

BACKGROUND

Advances have been made in techniques and tools for use in minimally invasive surgery that can be performed through small incisions or intravascularly. For example, improvements have been made recently to reduce the invasiveness of cardiac surgery. To avoid open procedures, such as open, stopped-heart surgery, which can lead to high patient morbidity and mortality, devices and methods have been developed for operating through small incision, for operating on a beating heart, and for performing cardiac procedures via intravascular or intravascular access. For many minimally invasive surgery techniques, significant challenges include positioning the treatment device or devices in a desired location for performing the procedure and deploying the treatment into or on the target tissue.

Heart valve repair can benefit from less invasive surgical techniques. Traditional treatment of heart valve stenosis or regurgitation, such as mitral or tricuspid regurgitation, typically involves an open-heart surgical procedure to replace or repair the valve. Valve repair procedures usually involve annuloplasty, which is a set of techniques designed to restore the valve annulus shape and strengthen the annulus. Conventional annuloplasty surgery generally requires a thoracotomy (a large incision into a patient's thorax), and sometimes a median sternotomy (an incision through a patient's sternum). These open-heart, open-chest procedures routinely involve placing the patient on a heart-lung bypass machine for long periods of time so that the patient's heart and lungs can be stopped during the procedure. In addition, valve repair and replacement is typically technically challenging and requires a substantial incision through a heart wall to access the valve. Many patients such as elderly patients, children, patients with complicating conditions such as comorbid medical conditions or those having undergone other surgical procedures, and patients with heart failure, are not considered candidates for heart valve surgery because of the high risk involved.

Minimally invasive procedures are typically performed endoscopically through catheters, through small incisions or intravascularly. Instruments such as graspers, dissectors, clip appliers, lasers, cauterization devices and clamps are routinely used endoscopically, with an endoscope used for visualizing the procedure. When a surgeon desires to bring pieces of two tissue together, the surgeon typically threads a suture through the two pieces of tissue, applies tension, and ties off or knots the suture to maintain the tension. However, during endoscopic surgery, the manipulation required when knotting or tying suture material can be difficult because of severely restricted space.

Previously, there have been attempts to maintain tension in tissue by using staples, clips, clamps, or other fasteners to obviate the need for suturing. However, these methods do not provide adjustable tension such as is available when a surgeon uses suture. U.S. Pat. Nos. 5,520,702 and 5,643,289 describe deformable cylindrical tubes that can be applied over a loop of suture. After a suture is adjusted to a desired tension, the suture is looped, and a deployment gun applies a deformable tube over the suture loop and crimps it so that it clamps down on the suture. After the loop is secured with a crimp, a separate cutting member or tool can be used to cut the excess suture material. U.S. Pat. No. 6,099,553 also describes deformable crimps that can be applied over the ends of sutures to fix them into place. Similar crimping devices that operate to mechanically fasten suture together and cut away excess tether are provided as TI-KNOT® knot replacement systems by LSI Solutions®. However, with crimping schemes, the suture may still slip through crimps and lose tension, especially if the suture has a small diameter, if the suture is made of a material susceptible to slippage, such as metal or TEFLON® fluoropolymer, or if the crimp is insufficiently deformed. U.S. Publication No. 2003/0167071 describes fasteners made from shape memory materials that can be applied to sutures to avoid tying knots in catheter-based procedures. U.S. Pat. Nos. 6,409,743 and 6,423,088 describe fusible collars that can be used in place of knots in securing sutures. These fusible collars require an external source of energy be locally applied to the collar without damaging surrounding tissue for the fusing process.

Devices and methods for less-invasive repair of cardiac valves have been described. In heart valve repair procedures, it is often desired for a physician to secure one or more treatment devices to valve annulus tissue. Annular tissue tends to be more fibrous than muscular or valve leaflet tissue, and thus can be more suitable tissue for securing treatment devices such as anchors to treat a heart valve. Devices and methods for positioning anchor delivery devices are described in U.S. Patent Application Ser. Nos. 60/445,890, 60/459,735, 60/462,502, 60/524,922, 10/461,043, 10/656,797, 10/741,130 and 10/792,681, which were previously incorporated by reference. For example, these references describe devices and methods for exposing, stabilizing and/or performing a procedure on a heart valve annulus.

Many treatments, including annuloplasty, involve tightening of tissue. For some tissue tightening procedures, anchors coupled to a suture are embedded in tissue, and the suture is then cinched to tighten the tissue via the anchors. Examples of devices and methods for such procedures applied to heart valve repair are provided in U.S. patent application Ser. Nos. 10/656,797, 10/741,130 and 10/792,681.

Improved methods and devices for locking a suture to maintain tension in the suture are desired, especially in minimally invasive treatments where surgical access is limited. For treatments involving tissue anchors, improved methods and devices are desired for locking a suture that has been coupled with the anchors such that the suture does not move relative to the last applied anchor. Also desired are improved methods and devices for severing excess suture so that it can be removed.

BRIEF SUMMARY

Described herein are devices and methods for use in termination procedures during tissue tightening treatments. In general, termination involves any one or all of the steps carried out when finishing a tissue tightening procedure, including: cinching a tether to tighten tissue; locking the cinching tether in place; and cutting off excess tether. Tissue anchors can be secured to the tissue to be tightened and the tether coupled to the anchors, so that cinching of the tether tightens the tissue via the anchors.

In some variations, a method for tightening tissue is provided. A first anchor is fixedly coupled to a tether, and a second anchor is slidably coupled to the tether. Both anchors are secured to the tissue to be tightened. Tension is applied to the tether intravascularly, the second anchor is fixedly coupled to the tether, and the tether is cut.

In some variations, the anchors are secured to the tissue intravascularly. In some variations, the tissue includes heart tissue. For example, the tissue can include a heart valve annulus or a mitral valve annulus.

A force having a component counter to the tensioning force applied to the tether can be applied to the second anchor in some variations. An intravascular device can be contacted with the second anchor to apply the force to the second anchor.

In some variations, a portion of the tether is loaded into an intravascular device after the anchors are secured to the tissue. The tether can be captured with a loop to load it into the intravascular device. The tether can also be threaded through a feature in a rod, and the rod can be inserted into the intravascular device. The features in the rod can include openings, indents, grooves, slits, or the like.

In other variations, the tether can be fixedly coupled to the anchor intravascularly. In some variations, the tether is fixedly coupled to the second anchor by clamping the tether to the second anchor. In other variations, the tether can be fixedly coupled to the second anchor by deforming the second anchor. In still other variations, the tether can be fixedly coupled to the second anchor by applying an adhesive to the tether.

In some variations, the tether is fixedly coupled to the second anchor by providing a locking feature on the tether. The tether can be threaded through a feature on the second anchor, and the locking feature cannot pass through the feature on the second anchor in the direction toward the first anchor. The locking feature can include protrusions that allow the locking feature to slide along the tether in one direction only. The locking feature can include a knot. The locking feature can include a washer through which the tether passes and a knot on the tether, which cannot pass through the washer. In some variations, the locking feature can pass through the feature on the second anchor through which the tether passes in the direction away from the first anchor. The feature on the second anchor can include an eyelet.

In some variations, the locking feature is clamped to the tether. The tether can be clamped between an expanded deformable mesh and the inner wall of a tube. The tether can be clamped by applying a force to at least partially unkink a kinked tube, passing the tether through the tube, and then releasing the force to re-kink the tube. In some variations, the tether is clamped by applying a force to separate two surfaces of the locking feature, passing the tether between the surfaces, and releasing the force to clamp the tether between the surfaces. The tether can be clamped by applying a force to cause two surfaces of the locking feature to move together to clamp the tether between the two surfaces. In other variations, the tether is passed through an opening in a deformable material, and the deformable material is deformed to cause a dimension in the opening in the deformable material to decrease, thereby clamping the tether. The tether can be clamped by passing the tether through the locking feature and altering the path of the tether through the locking feature to increase the frictional forces on the tether.

A locking feature (e.g., a clamp, lock, knot, or other tether-securing feature) may be detachable from a delivery device. For example, a locking feature may be releasably (or detachably) connected to a tube, rod, or wire, etc. In one variation, the termination device comprises a locking feature that is detachably connected to a delivery tube. Other features may also be included as part of the termination device, include a tether cutter, a push rod (for detaching and/or activating the locking feature), etc.

In some variations, the cutting of the tether is performed intravascularly. In other variations, the tether is cut proximal to the second anchor. In still other variations, the tether is cut by shearing the tether between two concentric tubes. One concentric tube can be advanced with respect to the other concentric tube along the axis of the tubes. Alternatively, one concentric tube can be rotated with respect to the other concentric tube about the axis of the tubes.

In some variations, the tether can be cut by passing the tether through an opening in a tube and rotating a blade in a plane that intersects an axis of the tube. In other variations, the tether can be cut by contacting the tether with a cutting blade. In still other variations, the tether can be cut by passing the tether through a tube, inflating in the tube a balloon to which one or more cutting blades are mounted and rotating the balloon. In other variations, the tether can be cut by shearing the tether between two blades sharing a pivot.

In some variations, a single intravascular device can deploy the anchors, apply tension to the tether, fixedly couple the tether to the second anchor and cut the tether. In other variations, the same or different intravascular device may be used to perform any step or combination of steps in a method for tightening tissue that includes securing to the tissue a first anchor fixedly coupled to a tether and a second anchor slidably coupled to the tether, applying tension to the tether intravascularly, fixedly coupling the tether to the second anchor and cutting the tether.

In some variations, a termination device includes a detachable locking feature and a tether cutter. For example, the termination device may comprise a tubular body that couples to a tether with a detachable locking feature at the distal end of the termination device. The termination device may also include a tether cutter. In some variations, the tether cutter is located proximal to the detachable locking feature. In operation, the tether may be coupled to the detachable locking feature (e.g., by threading through a region of the detachable locking feature), and the locking feature may be positioned to secure the tether (e.g., abutting an anchor). The tether may be tensioned appropriately, and the locking feature can be locked and detached from the rest of the termination device. The tether maybe cut either before or after detaching the locking feature. In some variations, the termination device comprises a rod for locking the detachable locking feature and/or for detaching the detachable locking feature.

Described herein are termination devices for locking an implantable and cinchable tether. The termination devices may include an elongate body and a locking feature releasably attached to the distal end of the elongate body. The locking feature is typically configured to couple to the tether, and has an unsecured state (e.g., an "open" state in some variations), wherein the tether may move with respect to the locking feature, and a secured state (e.g., a "closed state" in some variations), wherein the tether is secured by the locking feature. The termination device may also include a tether cutter. For example, a tether cutter may be located distally to the locking feature. (such as a cutting tube within the elongate body). In some variations, the elongate body is configured as a catheter.

In some variations, the termination device may also include a force applicator for releasing the locking feature from the rest of the termination device. For example, the force applicator may comprise a push rod extending longitudinally within the elongate body of the termination device. The termination device may also include a releasable attachment region between the locking feature and the elongate body that can be broken or detached to separate the locking feature of the termination device from the rest of the device. The releasable attachment region may be a frangible region, and may be configured to separate the locking feature from the elongate body when a force of greater than a predetermined load (e.g., about 2 lbs) is applied to the locking feature. In some variations, the releasable attachment region comprises a perforated region. The releasable attachment region may also be formed by the connection between two regions made up of different materials. For example, the locking feature may comprise a different material than the elongate body. The locking feature may also be separated from the body of the termination device (e.g., catheter) by a cutter. The cutter may be a sharp slot, hole, or edge attached to an elongate element that slides relative to the joint (e.g., the releasable attachment region), and thus cuts the joint. The cutter may also cut the joint and the tether in a single motion.

Any appropriate locking feature may be used. In some variations, the locking feature comprises a clamp. In some variations, the locking feature comprises a plug or inner tube that is configured to compress the tether against a wall of the locking feature when the locking feature is in the secured state.

Also described herein are termination devices including an elongate body, a locking feature releasably attached to the distal end of the elongate body (the locking feature configured to couple to the tether) and a tether cutter coupled to the elongate body, wherein the tether cutter may be activated to cut the tether.

Methods of securing a cinchable tether are also described. In some variations, these methods may include the steps of coupling the tether to a termination device (wherein the termination device comprises an elongate body and a locking feature releasably attached to the distal end of the elongate body, so that the locking feature can be coupled to the tether), cinching the tether, and securing the tether with the locking feature.

In some variations, the method of securing a cinchable tether may also include the step of cutting the tether (e.g., using a tether cutter, including a tether cutter that is part of the termination device). The method may also include the step of separating the locking feature from the elongate body. In some variations, the step of separating the locking feature from the elongate body includes applying force to separate the locking feature from the elongate body. The step of applying force may comprise pushing a push rod located at least partly within the elongate body.

BRIEF DESCRIPTION OF THE DRAWINGS

FIGS. 10A-10F illustrate a method for applying anchors to a valve annulus and cinching the anchors to tighten the annulus, using an anchor delivery device according to some embodiments.

FIGS. 29A-F illustrate various examples of termination devices and methods that utilize sharpened tubes to sever excess tether after the tether is locked into place.

DETAILED DESCRIPTION

The present application discloses methods and devices for tightening tissue. These methods generally involve securing to the tissue a first anchor that is coupled to a tether, securing to the tissue a second anchor that is slidably coupled to the tether, applying tension to the tether, fixing the position of the tether with respect to the second anchor, and cutting the tether. Any or all of these steps can be performed intravascularly. For example, tension can be applied to the tether intravascularly, and the anchors can be secured to the tissue intravascularly. Although for exemplary purposes the following description typically focuses on uses of the disclosed methods and devices in mitral valve and other heart valve repair, such description should not be interpreted to limit the scope of the invention as defined by the claims. Tissue tightened by the disclosed methods and devices may comprise any part of the body including, for example, the heart, bladder, stomach, gastroesophageal junction, vasculature, gall bladder, or the like. The methods and devices disclosed herein may be used, for example, to close or reduce the diameter of any suitable body lumen, valve or structure or to tether portions of tissue which are separate or which have been traumatically severed.

Heart tissue tightened by the disclosed methods and devices may comprise, for example, an atrial-septal defect or a heart valve annulus such as, for example, a mitral valve annulus. In many cases, methods disclosed herein may be performed on a beating heart. Access to the beating heart may be accomplished by any available technique, including intravascular, transthoracic, and the like. In addition to beating heart access, the methods disclosed herein may be used for intravascular stopped heart access as well as stopped heart open chest procedures.

The first portion of this application will describe exemplary methods and devices for securing tethered anchors to tissue in the context of a heart valve repair procedure. The anchors can be secured to tissue intravascularly. Subsequent portions of the application will describe exemplary methods and devices for applying tension to the tether to tighten the tissue, for locking the tether to an anchor or otherwise fixing the position of the tether with respect to an anchor to maintain the tension, and for cutting the tether. The methods and devices described for performing these steps are meant to be exemplary and should not be interpreted as limiting the scope of the claims.

Figure 1:
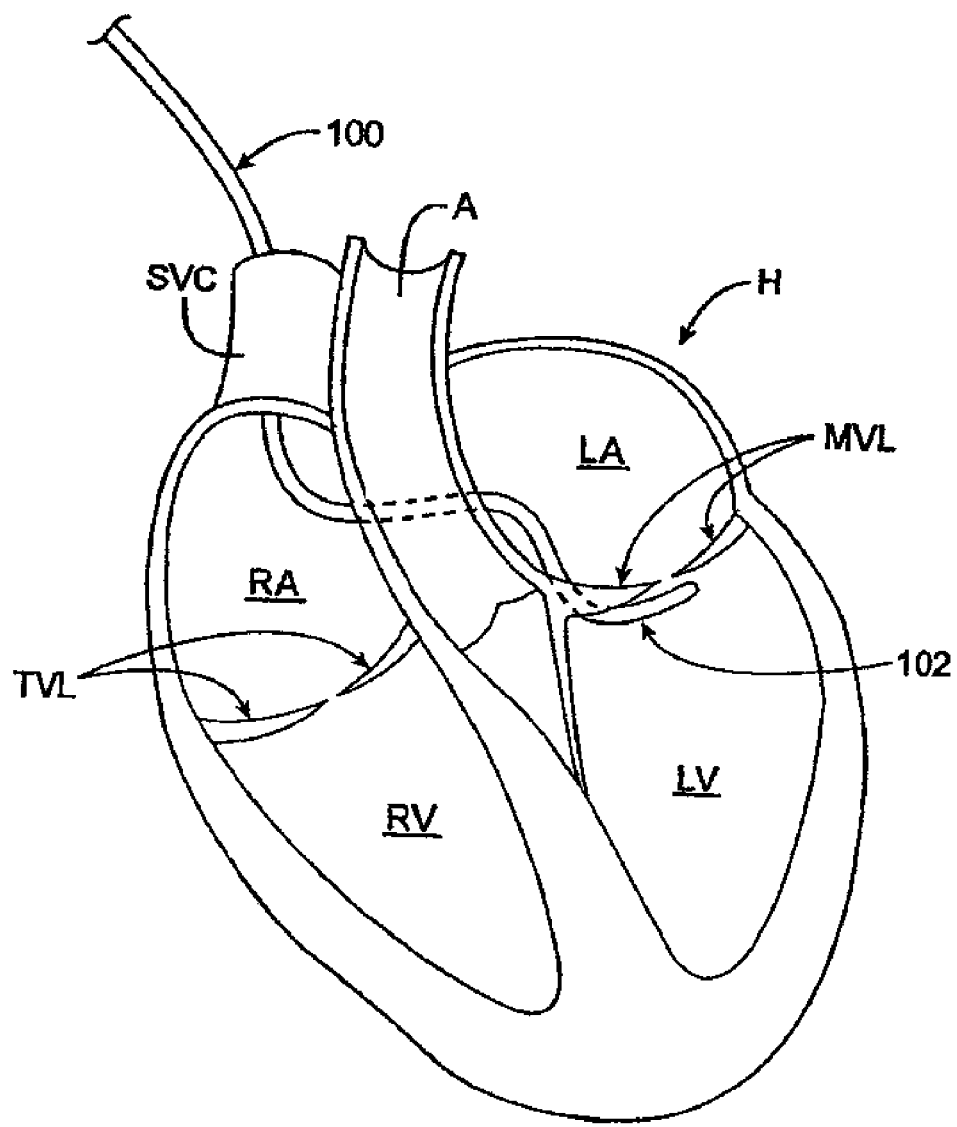
FIG. 1 is a cross-sectional view of a heart with a flexible anchor delivery device being positioned for treatment of a mitral valve annulus, according to some embodiments.

Referring now to FIG. 1, a heart H is shown in cross section, with an elongate anchor delivery device 100 introduced within the heart H. Generally, delivery device 100 comprises an elongate body with a distal portion 102 configured to deliver anchors to, for example, a heart valve annulus. (In FIGS. 1, 2A and 2B, distal portion 102 is shown diagrammatically without anchors or an anchor-delivery mechanism to enhance clarity of the figures.) In some embodiments, the elongate body comprises a rigid shaft, while in other embodiments it comprises a flexible catheter, so that distal portion 102 may be positioned in the heart H and, for example, under one or more valve leaflets to engage a valve annulus via a intravascular approach. Intravascular access may be gained, for example, through the internal jugular vein (not shown) to the superior vena cava SVC to the right atrium RA, across the interatrial septum to the left atrium LA, and then under one or more mitral valve leaflets MVL to a position within the left ventricle (LV) under the valve annulus (not shown). Alternatively, access to the heart may be achieved via the femoral vein and the inferior vena cava. In other embodiments, access may be gained via the coronary sinus (not shown) and through the atrial wall into the left atrium. In still other embodiments, access may be achieved via a femoral artery and the aorta, into the left ventricle, and under the mitral valve. Any other suitable access route may also be used.

In other embodiments, access to the heart H may be transthoracic, with delivery device 100 being introduced into the heart via an incision or port in the heart wall. Even open heart surgical procedures may benefit from the disclosed methods and devices. Furthermore, some embodiments may be used to enhance procedures on the tricuspid valve annulus, adjacent the tricuspid valve leaflets TVL, or any other cardiac or vascular valve. Therefore, although the following description typically focuses on minimally invasive or less invasive mitral valve repair for treating mitral regurgitation, the disclosed methods and devices are in no way limited to that use.

Figure 2A:
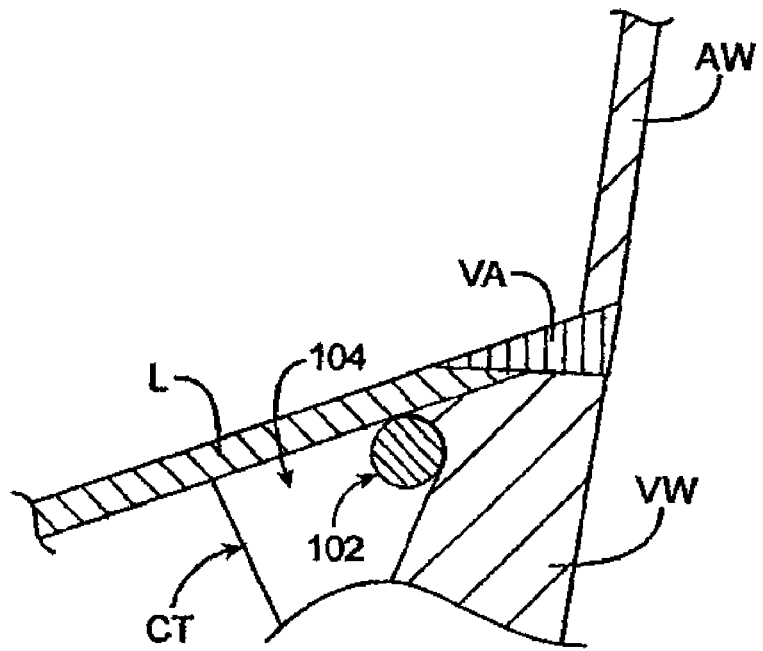
FIGS. 2A-D are cross-sectional views of a portion of a heart, schematically showing positioning of a flexible device for treatment of a mitral valve annulus, according to some embodiments.
Figure 2B:
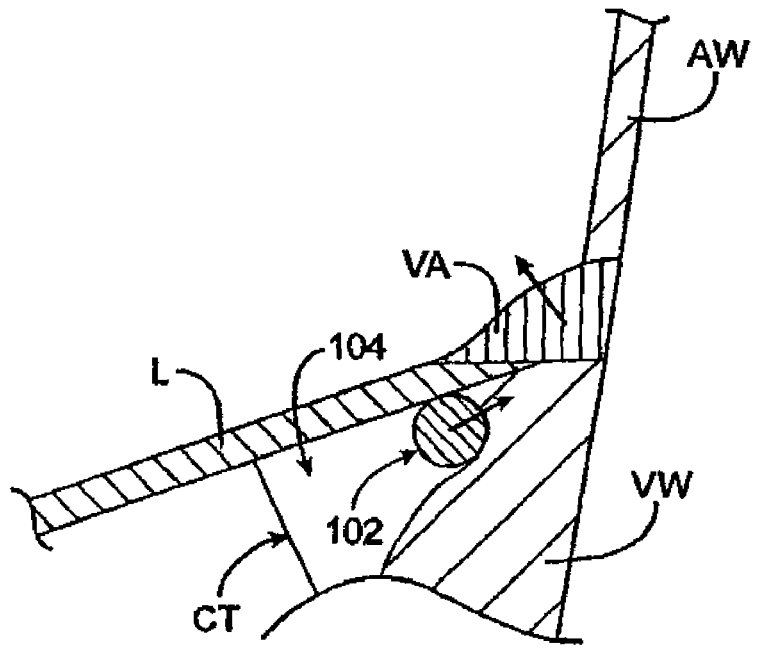

With reference now to FIGS. 2A and 2B, a method for positioning delivery device 100 for treating a mitral valve annulus VA is depicted diagrammatically in a cross-sectional view. First, as in FIG. 2A, distal portion 102 is positioned in a desired location under a mitral valve leaflet L and adjacent a ventricular wall VW. (Again, distal portion 102 is shown without anchors or anchor-delivery mechanism for demonstrative purposes.) The valve annulus VA generally comprises an area of heart wall tissue at the junction of the ventricular wall VW and the atrial wall AW that is relatively fibrous and, thus, significantly stronger than leaflet tissue and other heart wall tissue.

Distal portion 102 may be advanced into position under the valve annulus by any suitable technique, some of which are described below in further detail. Generally, distal portion 102 may be used to deliver and secure anchors to the valve annulus, to stabilize and/or expose the annulus, or both. In some embodiments using a delivery device having a flexible elongate body as shown in FIG. 1, a flexible distal portion 102 may be passed from the right atrium RA through the interatrial septum in the area of the foramen ovale (not shown—behind the aorta A), into the left atrium LA and thus the left ventricle LV. Alternatively, flexible distal portion 102 may be advanced through the aorta A and into the left ventricle LV, for example using access through a femoral artery. Oftentimes, distal portion 102 will then naturally travel, upon further advancement, under the posterior valve leaflet L into a space defined above a subvalvular space 104 roughly defined for the purposes of this application as a space bordered by the inner surface of the left ventricular wall VW, the inferior surface of mitral valve leaflets L, and cordae tendineae CT connected to the ventricular wall VW and the leaflet L. It has been found that a flexible anchor delivery catheter, such as the delivery devices disclosed herein, when passed under the mitral valve via an intravascular approach, often enters subvalvular space 104 relatively easily and may be advanced along space 104 either partially or completely around the circumference of the valve. Once in space 104, distal portion 102 may be conveniently positioned at the intersection of the valve leaflet(s) and the ventricular wall VW, which intersection is immediately adjacent or very near to the valve annulus VA, as shown in FIG. 2A. These are but examples of possible access routes of an anchor delivery device to a valve annulus, and any other access routes may be used.

In some embodiments, distal portion 102 includes a shape-changing portion which enables distal portion 102 to conform to the shape of the valve annulus VA. The catheter may be introduced through the vasculature with the shape-changing distal portion in a generally straight, flexible configuration. Once it is in place beneath the leaflet at the intersection between the leaflet and the interior ventricular wall, the shape of distal portion 102 is changed to conform to the annulus and usually the shape is "locked" to provide sufficient stiffness or rigidity to permit the application of force from distal portion 102 to the annulus. Shaping and optionally locking distal portion 102 may be accomplished in any of a number of ways. For example, in some embodiments, a shape-changing portion may be sectioned, notched, slotted or segmented and one or more tensioning members such as tensioning cords, wires or other tensioning devices coupled with the shape-changing portion may be used to shape and rigidify distal portion 102. A segmented distal portion, for example, may include multiple segments coupled with two tensioning members, each providing a different direction of articulation to the distal portion. A first bend may be created by tensioning a first member to give the distal portion a C-shape or similar shape to conform to the valve annulus, while a second bend may be created by tensioning a second member to articulate the C-shaped member upwards against the annulus. In other embodiments, a shaped expandable member, such as a balloon, may be coupled with distal portion 102 to provide for shape changing/deforming. In various embodiments, any configuration and combination may be used to give distal portion 102 a desired shape.

For transthoracic methods and other embodiments, distal portion 102 may be pre-shaped, and the method may simply involve introducing distal portion 102 under the valve leaflets. The pre-shaped distal portion 102 may be rigid or formed from any suitable super-elastic or shape memory material, such as nickel titanium alloys, spring stainless steel, or the like.

In addition to delivering and securing anchors to the valve annulus VA, delivery device 100 (and specifically distal portion 102) may be used to stabilize and/or expose the valve annulus VA. Such stabilization and exposure procedures are described fully in U.S. patent application Ser. No. 10/656,797, which was previously incorporated by reference. For example, once distal portion 102 is positioned under the annulus, force may be applied to distal portion 102 to stabilize the valve annulus VA, as shown in FIG. 2B. Such force may be directed in any suitable direction to expose, position and/or stabilize the annulus. For example, upward and lateral force is shown in FIG. 2B by the solid-headed arrow drawn from the center of distal portion 102. In other cases, only upward, only lateral, or any other suitable force(s) may be applied. With application of force to distal portion 102, the valve annulus VA is caused to rise or project outwardly, thus exposing the annulus for easier viewing and access. The applied force may also stabilize the valve annulus VA, also facilitating surgical procedures and visualization.

Some embodiments may include a stabilization component as well as an anchor delivery component. For example, some embodiments may include two flexible members, one for contacting the atrial side of a valve annulus and the other for contacting the ventricular side. In some embodiments, such flexible members may be used to "clamp" the annulus between them. One of such members may be an anchor delivery member and the other may be a stabilization member, for example. Any combination and configuration of stabilization and/or anchor delivery members is contemplated.

Figure 2C:
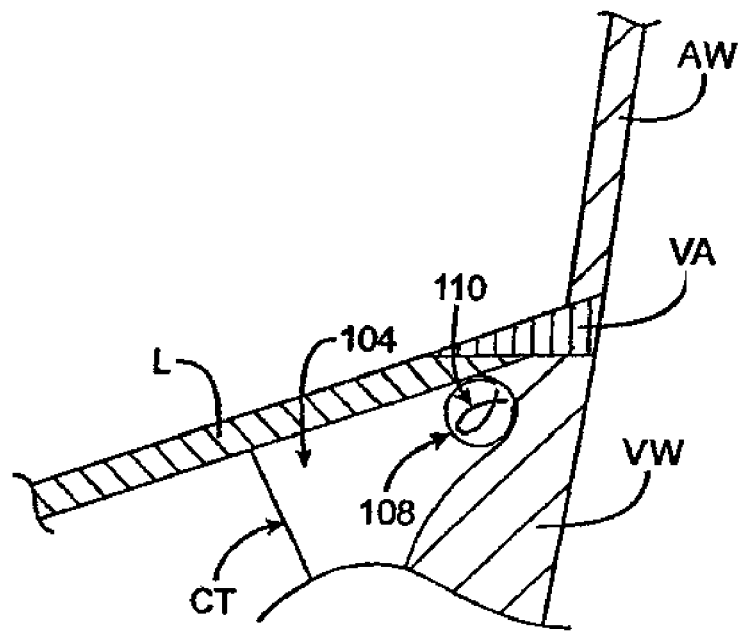
Figure 2D:
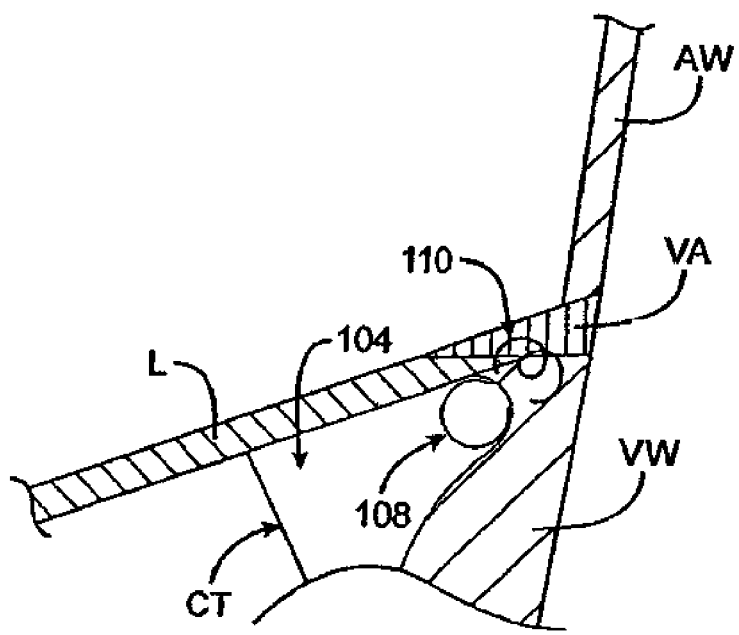

Referring now to FIGS. 2C and 2D, an anchor delivery device 108 is shown delivering and securing an anchor 110 to a valve annulus VA. These are again representational figures and are not drawn to scale. Anchor 110 is shown first housed within delivery device 108 (FIG. 2C) and then delivered to the annulus VA (FIG. 2D). As is shown, in some embodiments anchors 110 may have a relatively straight configuration when housed in delivery device 108, for example, anchors 110 may have two sharpened tips (although they need not be) and a loop in between the tips. Upon deployment from delivery device 108, the tips of anchor 110 may curve in opposite directions to form two semi-circles, circles, ovals, overlapping helices or the like. This is but one example of a type of self-securing anchor that may be delivered to a valve annulus. Typically, multiple coupled anchors 110 are delivered, and the anchors 110 are drawn together to tighten the valve annulus. Methods for anchor delivery and for drawing anchors together are described further below.

Although delivery device 108 is shown having a circular cross-sectional shape in FIGS. 2C and 2D, it may alternatively have any other suitable shape. In some embodiments, for example, it may be advantageous to provide a delivery device having an ovoid or elliptical cross-sectional shape. Such a shape may help ensure that the device is aligned, when positioned in a corner formed by a ventricular wall and a valve leaflet, such that one or more openings in the delivery device is oriented to deliver the anchors into valve annulus tissue. To further enhance contacting of the valve annulus and/or orientation of the delivery device, some embodiments may further include an expandable member, coupled with the delivery device, which expands to urge or press or wedge the delivery device into the corner formed by the ventricle wall and the leaflet to contact the valve annulus. Such enhancements are described further below.

Figure 3:
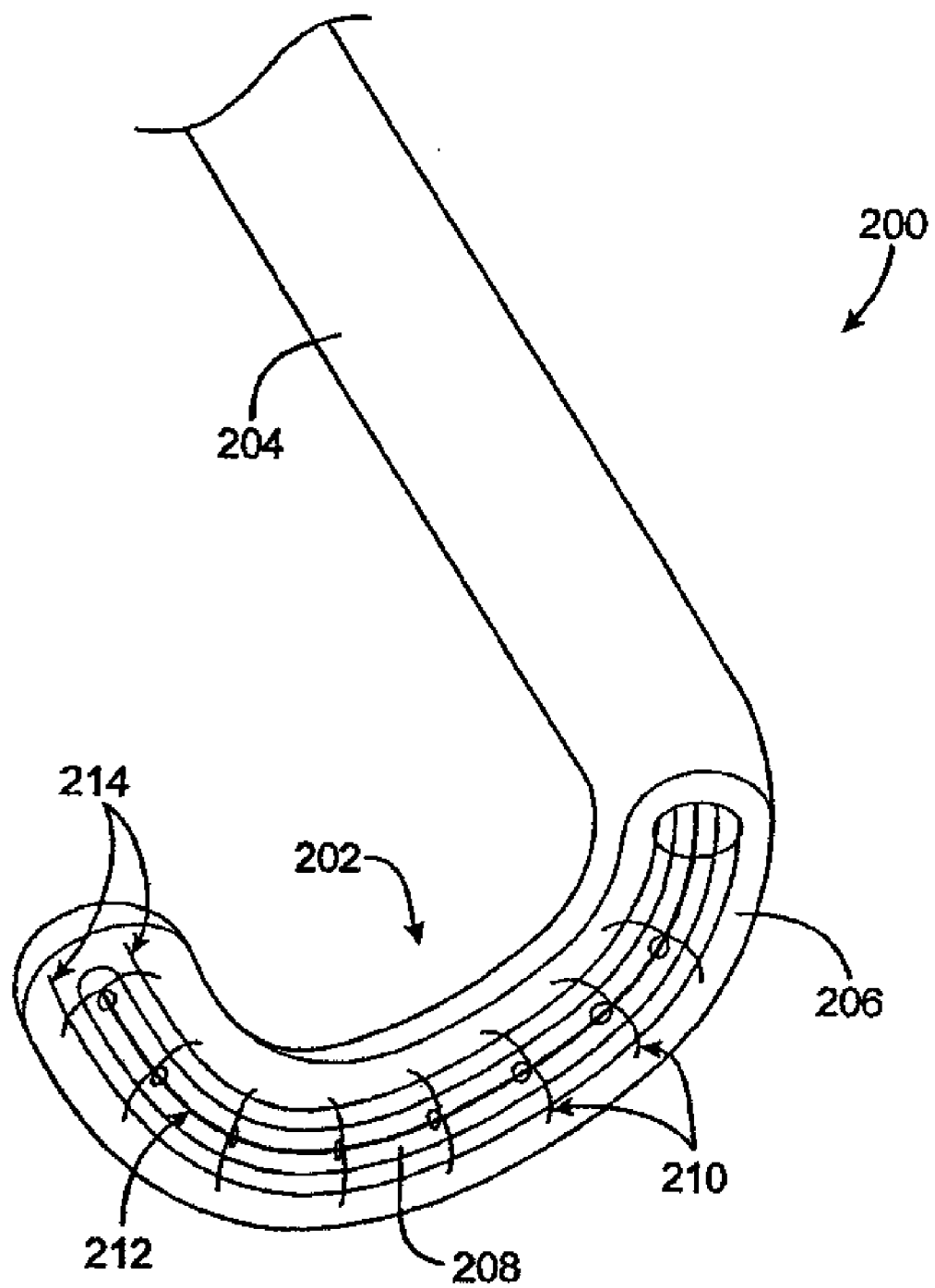
FIG. 3 is a perspective view of a distal portion of an anchor delivery device, according to some embodiments.

With reference now to FIG. 3, some embodiments of a portion of an anchor delivery device 200 suitably include an elongate shaft 204 having a distal portion 202 configured to deliver a plurality of anchors 210, coupled with a tether 212, to tissue of a valve annulus. Tethered anchors 210 are housed within a housing 206 of distal portion 202, along with one or more anchor retaining mandrels 214 and an expandable member 208. Many variations may be made to one or more of these features, and various parts may be added or eliminated. Some of these variations are described further below, but no specific embodiment(s) should be construed to limit the scope of the invention as defined by the appended claims.

Housing 206 may be flexible or rigid in various embodiments. In some embodiments, for example, flexible housing 206 may be comprised of multiple segments configured such that housing 206 is deformable by tensioning a tensioning member coupled to the segments. In some embodiments, housing 206 is formed from an elastic material having a geometry selected to engage and optionally shape or constrict the valve annulus. For example, the rings may be formed from super-elastic material, shape memory alloy such as nickel titanium alloys, spring stainless steel, or the like. In other instances, housing 206 could be formed from an inflatable or other structure that can be selectively rigidified in situ, such as a gooseneck or lockable element shaft, any of the rigidifying structures described above, or any other rigidifying structure.

"Anchors," for the purposes of this application, is defined to mean any fasteners. Thus, anchors (e.g., anchors 210) may comprise C-shaped or semicircular hooks, curved hooks of other shapes, straight hooks, barbed hooks, clips of any kind, T-tags, or any other suitable fastener(s). In some embodiments, as described above, anchors may comprise two tips that curve in opposite directions upon deployment, forming two intersecting semi-circles, circles, ovals, helices or the like. In some embodiments, anchors (e.g., anchors 210) are self-deforming. By "self-deforming" it is meant that anchors change from a first undeployed shape to a second deployed shape upon release of anchors from restraint in a housing (e.g., release of anchors 210 from housing 206). Such self-deforming anchors may change shape as they are released from a housing and enter valve annulus tissue to secure themselves to the tissue. Thus, for the example shown in FIG. 3, a crimping device or other similar mechanism is not required on distal end 202 to apply force to anchors 210 to attach them to annular tissue. Self-deforming anchors may be made of any suitable material, such as a super-elastic or shape-memory material like a nickel titanium alloy or spring stainless steel. In other embodiments, anchors may be made of a non-shape-memory material and may be loaded into a housing in such a way that they change shape upon release. Alternatively, anchors that are not self-deforming may be used, and such anchors may be secured to tissue via crimping, firing or the like. Even self-securing anchors may be crimped in some embodiments to provide enhanced attachment to tissue. Delivery of anchors may be accomplished by any suitable device and technique, such as by simply releasing the anchors by hydraulic balloon delivery as discussed further below. Any number, size and shape of anchors may be included in a housing.

In some embodiments, anchors (e.g., anchors 210) are generally C-shaped or semicircular in their undeployed form, with the ends of the "C" being sharpened to penetrate tissue or being blunt, but configured to penetrate tissue when expanded with force. Approximately midway along the C-shaped anchor, an eyelet may be formed for allowing slidable passage of a tether (e.g., tether 212). To maintain anchors 210 in their C-shaped, undeployed state, anchors 210 may be retained within housing 206 by two mandrels 214, one mandrel 214 retaining each of the two arms of the C-shape of each anchor 210. Mandrels 214 may be retractable within elongate catheter body 204 to release anchors 210 and allow them to change from their undeployed C-shape to a deployed shape. The deployed shape, for example, may approximate a complete circle or a circle with overlapping ends, the latter appearing similar to a key ring. Such anchors are described further below, but generally may be advantageous in their ability to secure themselves to annular tissue by changing from their undeployed to their deployed shape. In some embodiments, anchors (e.g., anchors 210) are also configured to lie flush with a tissue surface after being deployed. By "flush" it is meant that no significant amount of an anchor protrudes from the surface, although some small portion may protrude.

Tethers (e.g., tether 212) may be one long piece of material or two or more pieces and may comprise any suitable material, such as suture, suture-like material, a DACRON® polyester strip or the like. Retaining mandrels 214 may also have any suitable configuration and be made of any suitable material, such as stainless steel, titanium, nickel titanium alloys, or the like. Various embodiments may have one mandrel, two mandrels, or more than two mandrels.

In some embodiments, anchors 210 may be released from mandrels 214 to contact and secure themselves to annular tissue without any further force applied by delivery device 200. Some embodiments, however, may also include one or more expandable members 208, which may be expanded to help drive anchors 210 into tissue. Expandable member(s) 208 may have any suitable size and configuration and may be made of any suitable material(s). Hydraulic systems such as expandable members are known in the art, and any known or as yet undiscovered expandable member may be included in housing 206 as part of the present invention.

Figure 4:
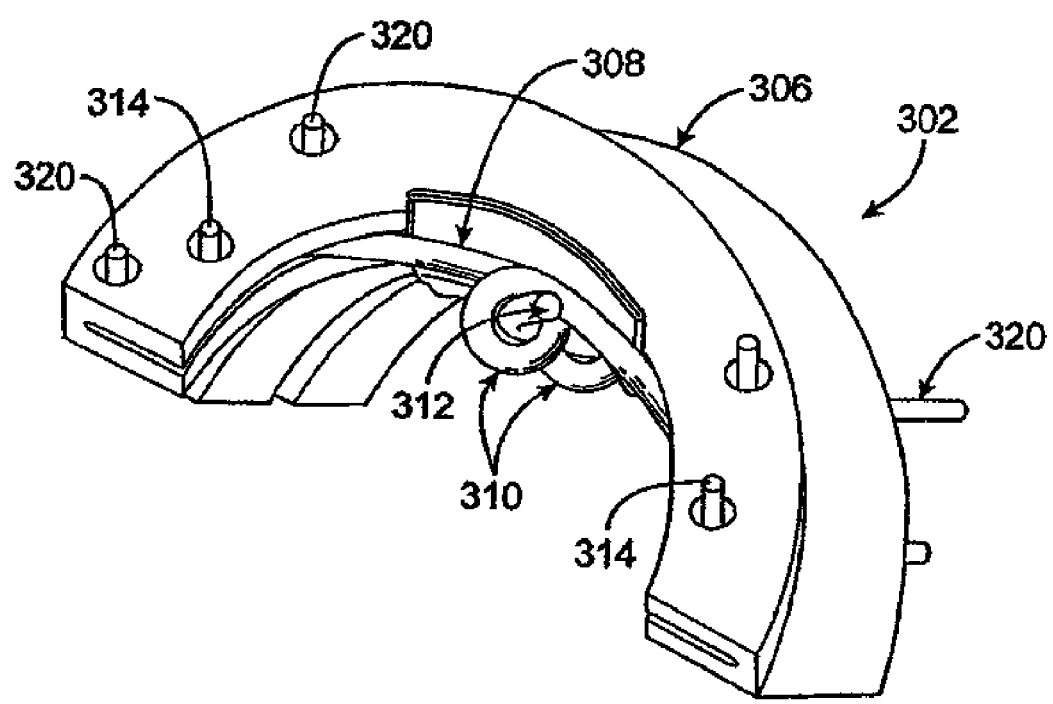
FIG. 4 is a perspective view of a segment of a distal portion of an anchor delivery device, with anchors in an undeployed shape and position.
Figure 5:
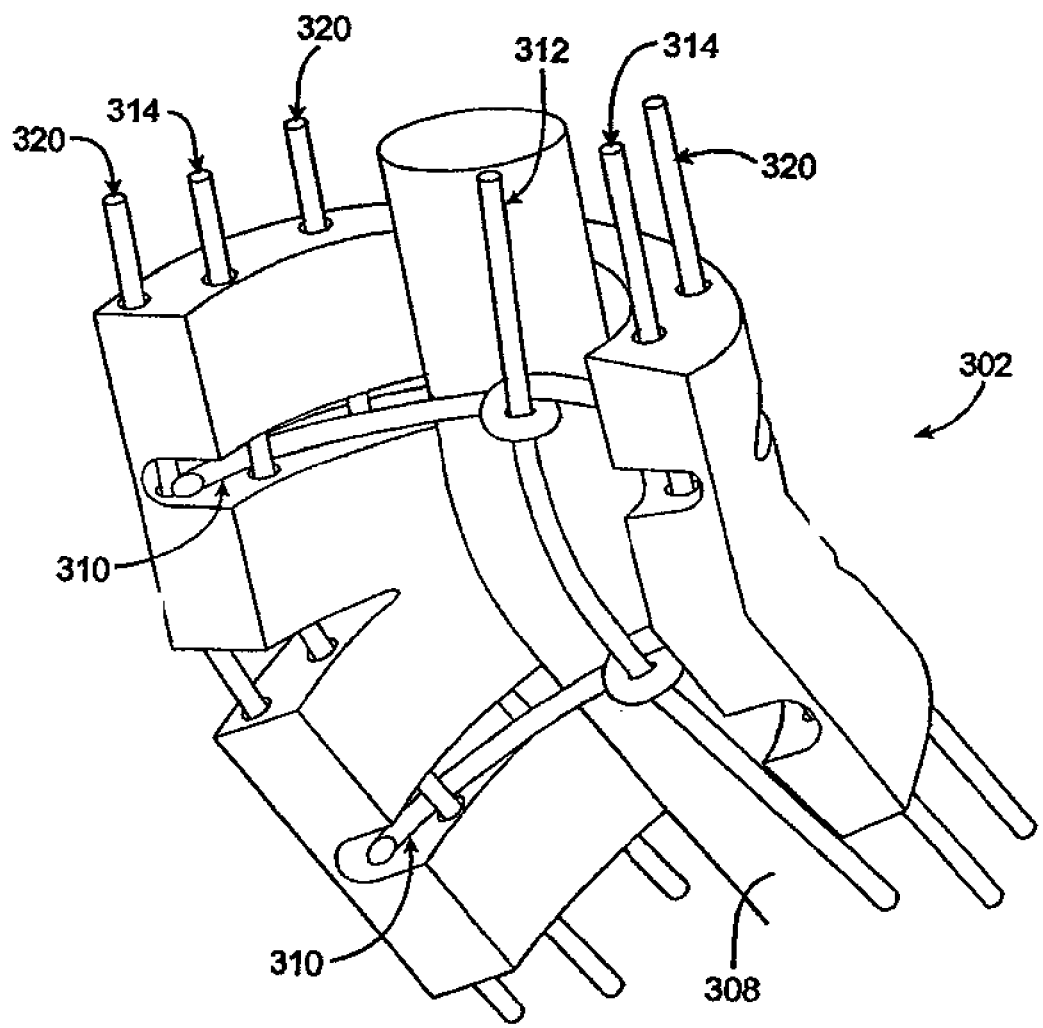
FIG. 5 is a different perspective view of the segment of the device shown in FIG. 4.

Referring now to FIGS. 4 and 5, a segment of a distal portion 302 of an anchor delivery device suitably includes a housing 306, multiple tensioning members 320 for applying tension to housing 306 to change its shape, two anchor retaining mandrels 314 slidably disposed in housing 306, multiple anchors 310 slidably coupled with a tether 312, and an expandable member 308 disposed between anchors 310 and housing 306. As can be seen in FIGS. 4 and 5, housing 306 may include multiple segments to allow the overall shape of housing 306 to be changed by applying tension to tensioning members 320. As also is evident from the drawings, "C-shaped" anchors 310 may actually have an almost straight configuration when retained by mandrels 314 in housing 306. Thus, for the purposes of this application, "C-shaped" or "semicircular" refers to a very broad range of shapes including a portion of a circle, a slightly curved line, a slightly curved line with an eyelet at one point along the line, and the like.

Figure 6:
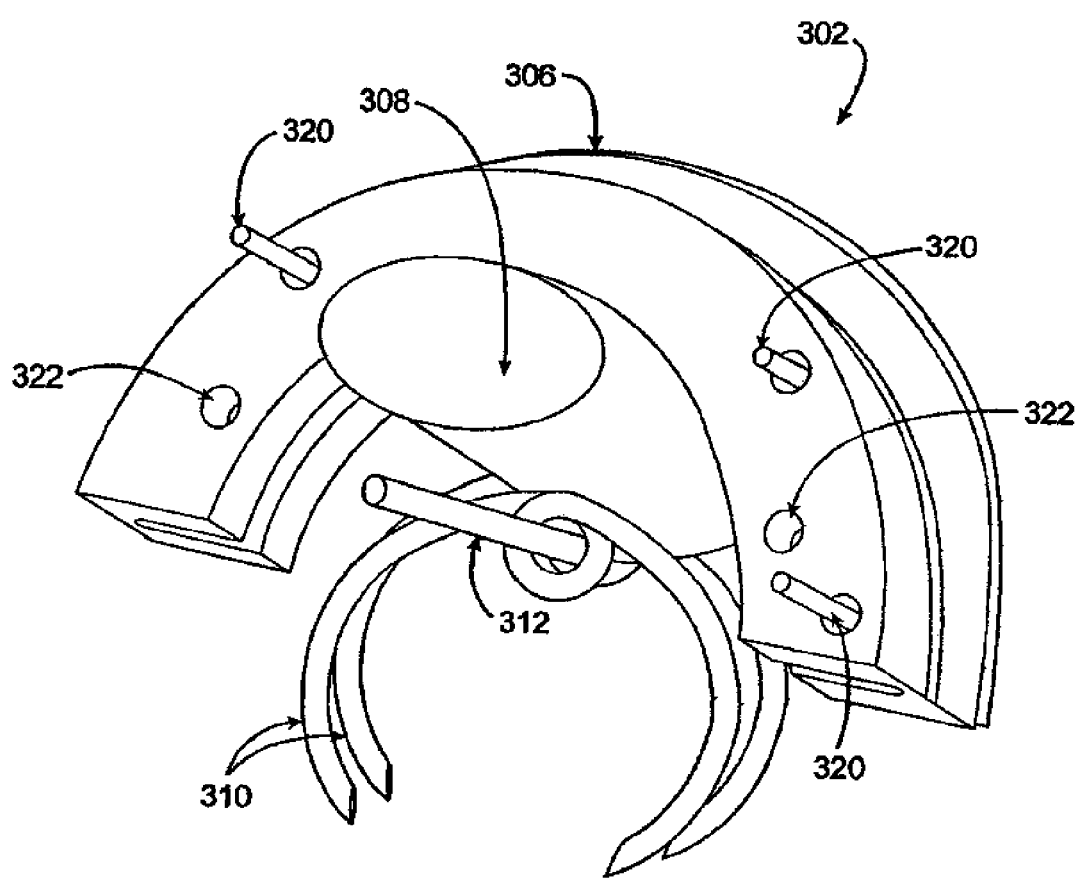
FIG. 6 is a perspective view of a segment of a distal portion of an anchor delivery device, with anchors in a deployed shape and position.

With reference now to FIG. 6, the same segment of distal portion 302 is shown, but mandrels 314 have been withdrawn from two mandrel apertures 322, to release anchors 310 from housing 306. Additionally, expandable member 308 has been expanded to drive anchors out of housing 306. Anchors 310, having been released from mandrels 314, have begun to change from their undeployed, retained shape to their deployed, released shape.

Figure 7A:
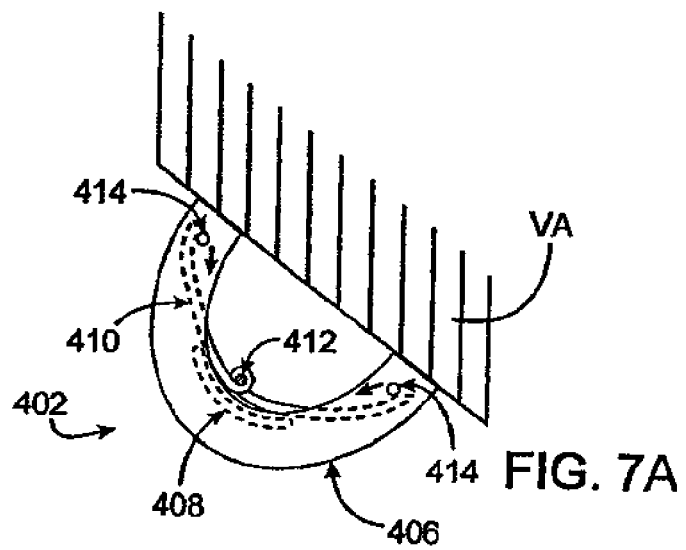
FIGS. 7A-7E are cross-sectional views of an anchor delivery device, illustrating a method for delivering anchors to valve annulus tissue.

Referring now to FIGS. 7A-7E, a cross-section of a distal portion 402 of an anchor delivery device is shown in various stages of delivering an anchor to tissue of a valve annulus VA. In FIG. 7A, distal portion 402 is positioned against the valve annulus, an anchor 410 is retained by two mandrels 414, a tether 412 is slidably disposed through an eyelet on anchor 410, and an expandable member 408 is coupled with housing 406 in a position to drive anchor 410 out of housing 406. When retained by mandrels 414, anchor 410 is in its undeployed shape. As discussed above, mandrels 414 may be slidably retracted, as designated by the solid-tipped arrows in FIG. 7A, to release anchor 410. In various embodiments, anchors 410 may be released one at a time, such as by retracting mandrels 414 slowly, may be released in groups, or may all be released simultaneously, such as by rapid retraction of mandrels 414.

Figure 7B:
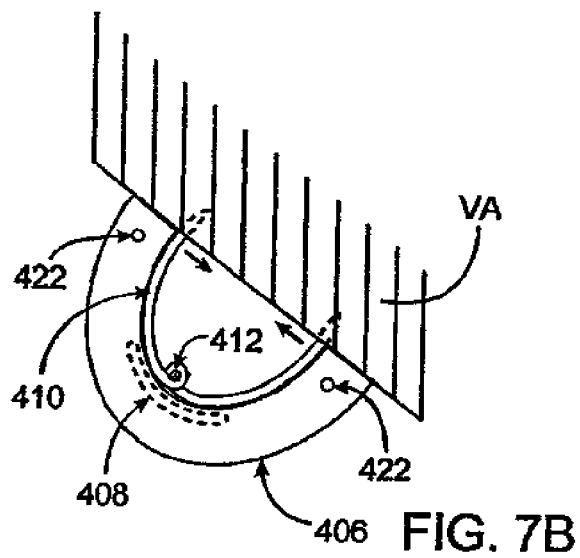
Figure 7C:
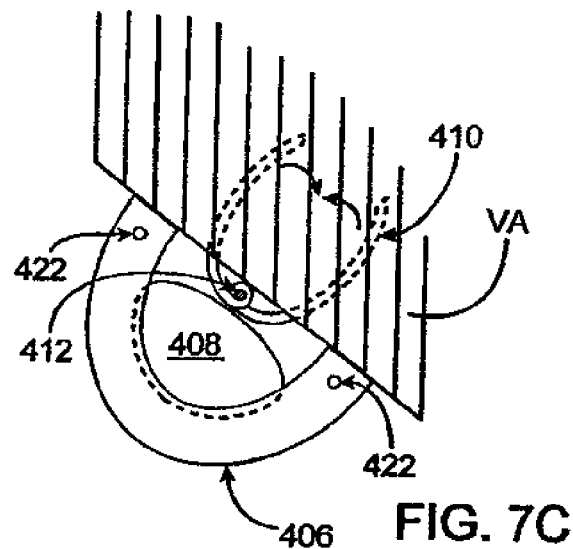
Figure 7D:
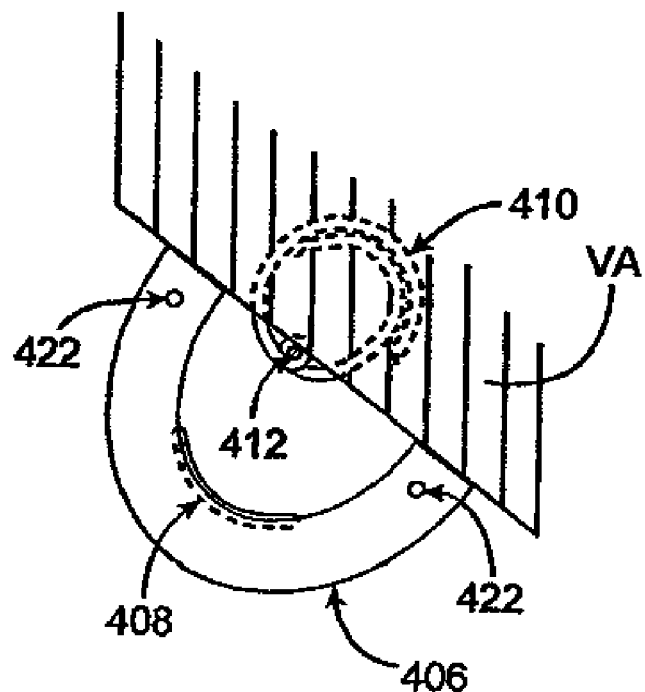
Figure 7E:
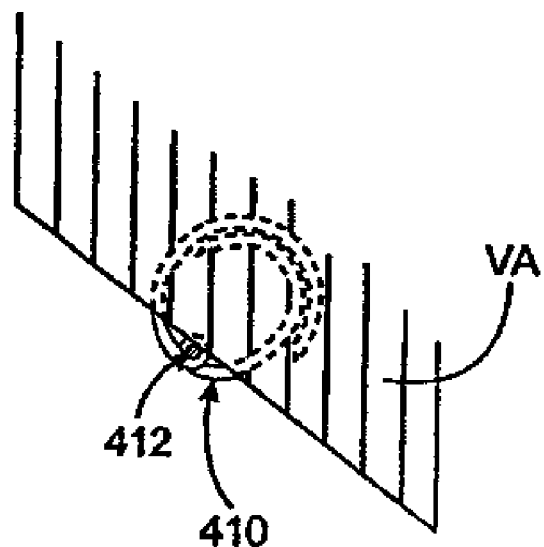

In FIG. 7B, anchor 410 has begun to change from its undeployed shape to its deployed shape (as demonstrated by the hollow-tipped arrows) and has also begun to penetrate the annular tissue VA. Empty mandrel apertures 422 demonstrate that mandrels 414 have been retracted at least far enough to release anchor 410. In FIG. 7B, expandable member 408 has been expanded to drive anchor 410 partially out of housing 406 and further into the valve annulus VA. Anchor 410 also continues to move from its undeployed towards its deployed shape, as shown by the hollow-tipped arrows. In FIG. 7D, anchor 410 has reached its deployed shape, which is roughly a completed circle with overlapping ends or a "key ring" shape. In FIG. 7E, delivery device 402 has been removed, leaving a tethered anchor secured in place in the valve annulus. Of course, there will typically be a plurality of tethered anchors secured to the annular tissue. Tether 412 may then be cinched to apply force to anchors 410 and cinch and tighten the valve annulus. The tether may be cinched using any suitable device or method. For example, during cinching a force can be applied to the most proximal anchor having a vector component counter to the force applied to the tether to cinch the tether. An intravascular device, such as a pusher, may be used to apply this force to the most proximal anchor.

Figure 8A:
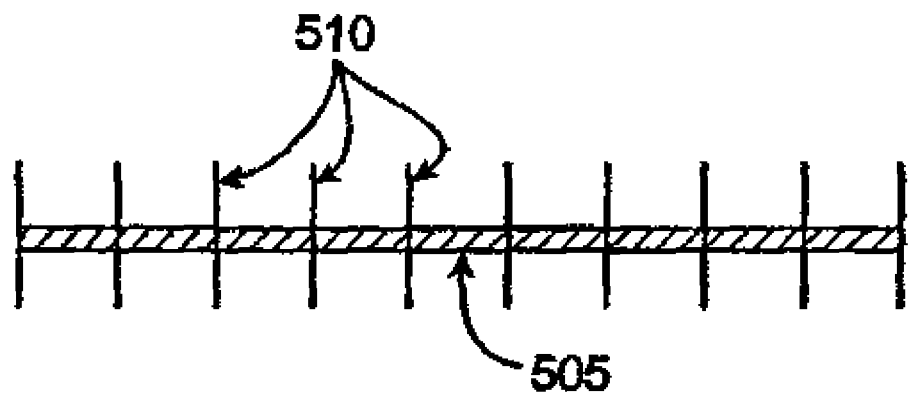
FIGS. 8A and 8B are top views of a plurality of anchors coupled to a self-deforming member or "backbone," with the backbone shown in an undeployed shape and in a deployed shape.
Figure 8B:
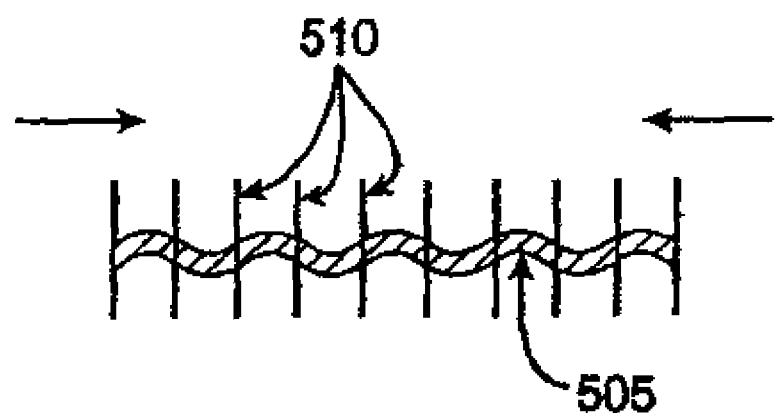

With reference now to FIGS. 8A and 8B, a diagrammatic representation of another embodiment of coupled anchors is shown. Here, anchors 510 are coupled to a self-deforming or deformable coupling member or backbone 505. Backbone 505 may be fabricated, for example, from nickel titanium alloys, spring stainless steel, or the like, and may have any suitable size or configuration. In one embodiment, as in FIG. 8A, backbone 505 is shaped as a generally straight line when held in an undeployed state, such as when restrained within a housing of an anchor deliver device. When released from the delivery device, backbone 505 may change to a deployed shape having multiple bends, as shown in FIG. 8B. By bending, backbone 505 shortens the longitudinal distance between anchors, as demonstrated by the solid-tipped arrows in FIG. 8B. This shortening process may act to cinch a valve annulus into which anchors 510 have been secured. Thus, anchors 510 coupled to backbone 505 may be used to cinch a valve annulus without using a tether or applying tethering force. Alternatively, a tether may also be coupled with anchors 510 to further cinch the annulus. In such an embodiment, backbone 505 will be at least partially conformable or cinchable, such that when force is applied to anchors 510 and backbone 505 via a tether, backbone 505 bends further to allow further cinching of the annulus.

Figure 9A:
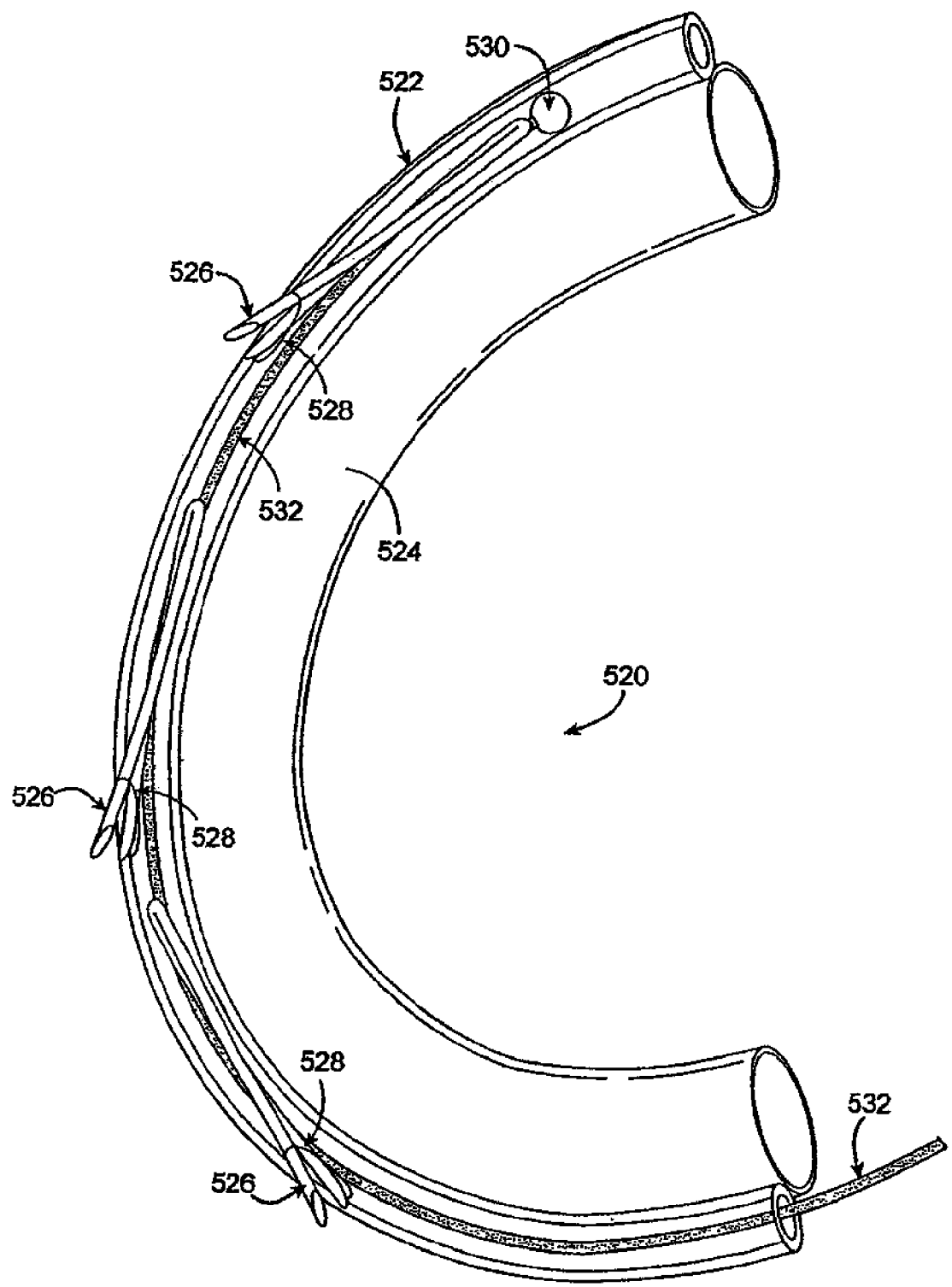
FIGS. 9A-9C are various perspective views of a distal portion of a flexible anchor delivery device according to some embodiments.
Figure 9B:
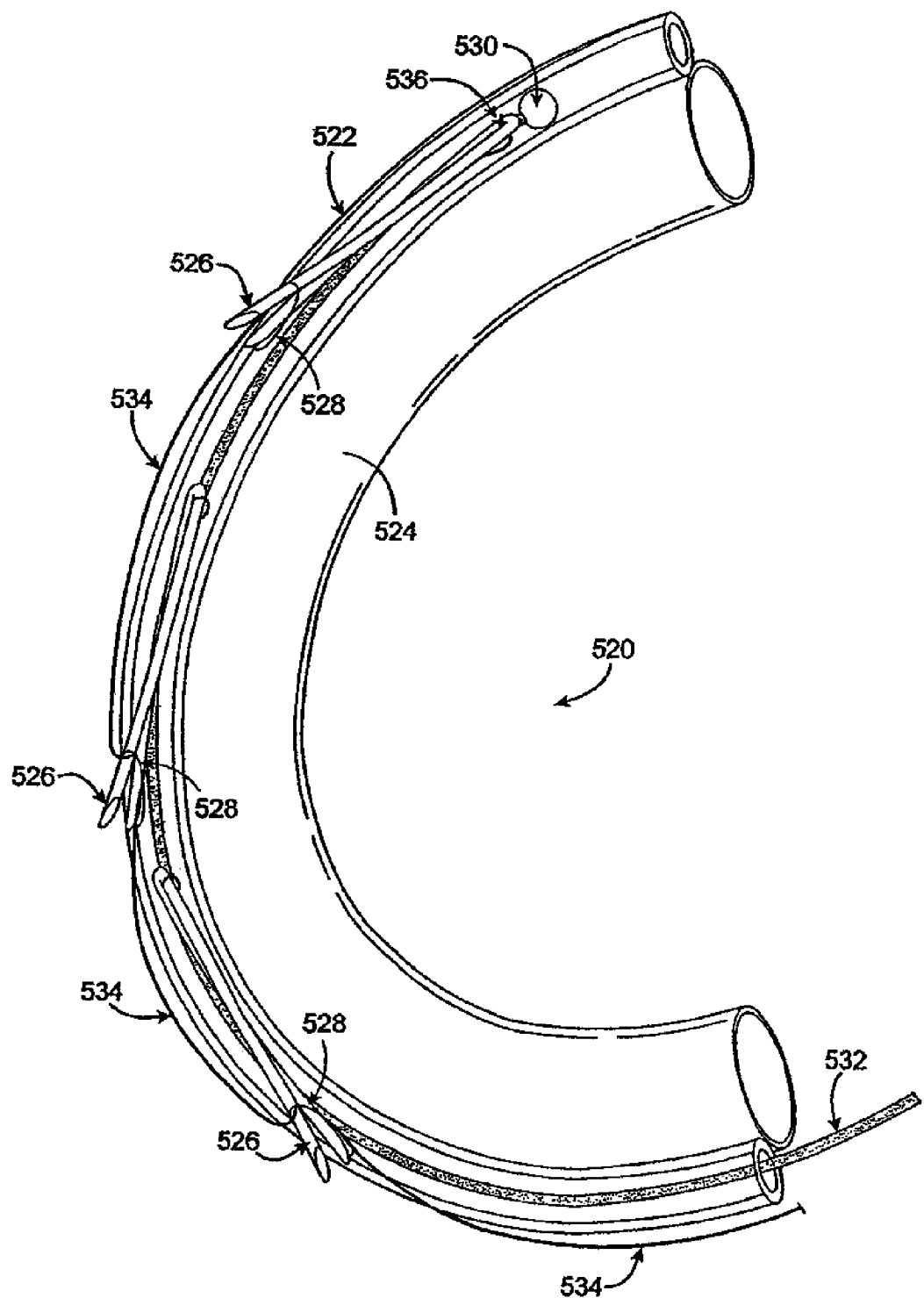
Figure 9C:
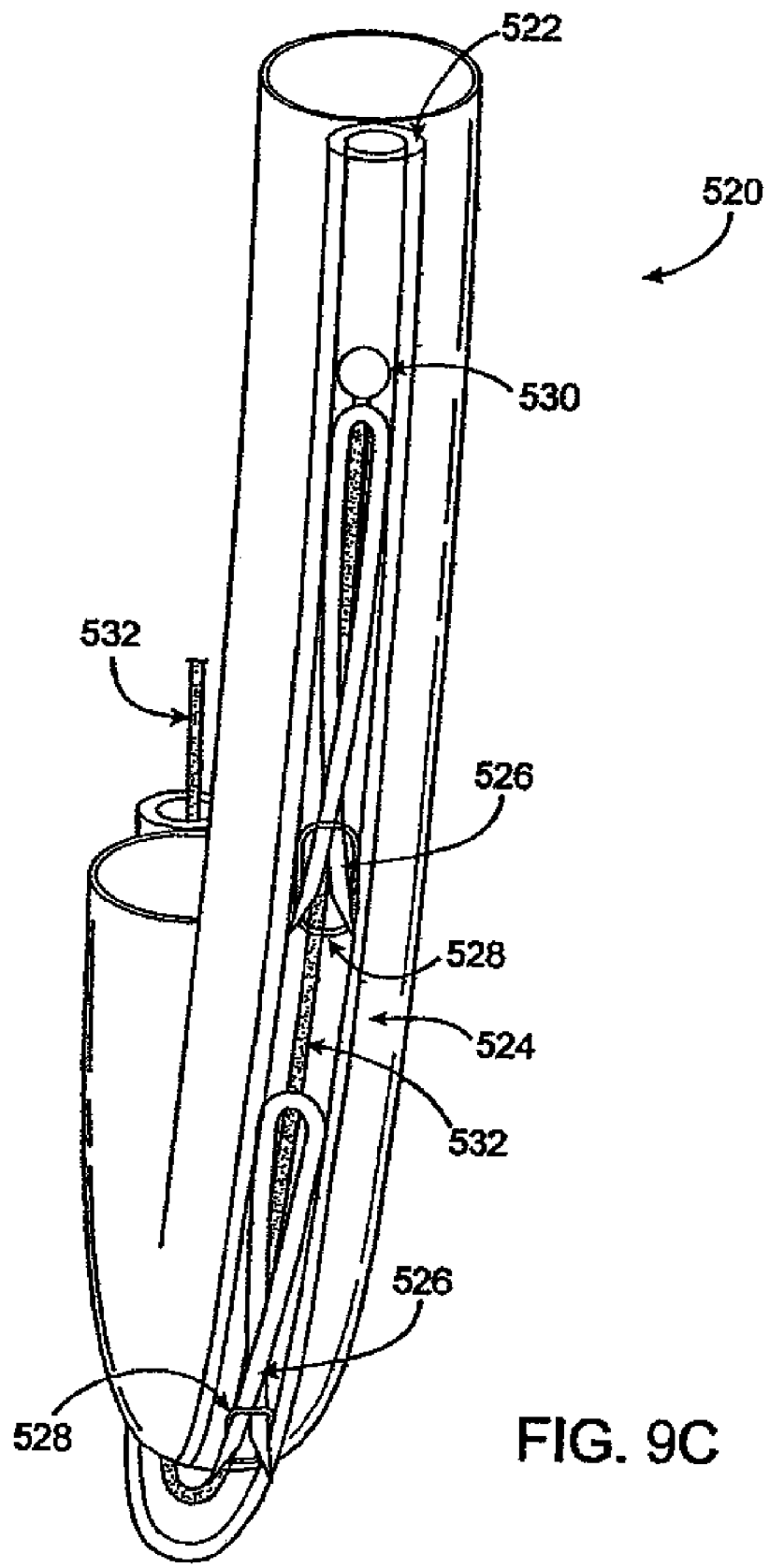

Referring now to FIGS. 9A-9C, in some embodiments a flexible distal portion of an anchor delivery device 520 suitably includes a housing 522 coupled with an expandable member 524. Housing 522 may be configured to house multiple coupled anchors 526 and an anchor contacting member 530 coupled with a pull cord 532. Housing 522 may also include multiple apertures 528 for allowing egress of anchors 526. For clarity, delivery device 520 is shown without a tether in FIGS. 9A and 9C, but FIG. 9B shows that a tether 534 may extend through an eyelet, loop or other portion of each anchor 526, and may exit each aperture 528 to allow for release of the plurality of anchors 526. Various features of these embodiments are described further below.

In the embodiments shown in FIGS. 9A-9C, anchors 526 are relatively straight and lie relatively in parallel with the long axis of delivery device 522. Anchor contacting member 530, which may comprise any suitable device, such as a ball, plate, hook, knot, plunger, piston, or the like, generally has an outer diameter that is nearly equal to or slightly less than the inner diameter of housing 522. Contacting member 530 is disposed within the housing, distal to a distal-most anchor 526, and is retracted relative to housing 522 by pulling pull cord 532. When retracted, anchor contacting member 530 contacts and applies force to a distal-most anchor 526 to cause that anchor 526 to exit housing 522 via one of the apertures 528. Contacting member 530 is then pulled farther proximally to contact and apply force to the next anchor 526 to deploy that anchor 526, and so on.

Retracting contacting member 530 to push anchors 526 out of apertures 528 may help cause anchors 526 to avidly secure themselves to adjacent tissue. Using anchors 526 that are relatively straight/flat when undeployed allows anchors 526 with relatively large deployed sizes to be disposed in and delivered from a relatively small housing 522. In some embodiments, for example, anchors 526 that deploy into a shape approximating two intersecting semi-circles, circles, ovals, helices, or the like, and that have a radius of one of the semi-circles of about 3 mm may be disposed within a housing 522 having a diameter of about 5 French (1.67 mm), or about 4 French (1.35 mm), or even smaller. Such anchors 526 may measure about 6 mm or more in their widest dimension. These are only examples, however, and other larger or smaller anchors 526 may be disposed within a larger or smaller housing 522. Furthermore, any convenient number of anchors 526 may be disposed within housing 522. In some embodiments, for example, housing 522 may hold about 1-20 anchors 526, or about 3-10 anchors 526. Other embodiments may hold more anchors 526.

Anchor contacting member 530 and pull cord 532 may have any suitable configuration and may be manufactured from any material or combination of materials. In alternative embodiments, contacting member 530 may be pushed by a pusher member to contact and deploy anchors 526. Alternatively, any of the anchor deployment devices and methods previously described may be used.

Tether 534, as shown in FIG. 9B, may comprise any of the tethers 534 or tether-like devices already described above, or any other suitable device. Tether 534 is generally fixedly coupled to a distal-most anchor 526 at an attachment point 536. By "fixedly coupled," here it is meant that tether 534 is coupled to distal-most anchor 526 in a manner that prevents tether 534 from sliding through or past distal-most anchor 526 in the direction of more proximal neighboring anchors 526. This may be achieved, for example, via a knot, weld, adhesive, or by any other suitable mechanism that fixedly couples tether 534 to distal-most anchor 526. Fixedly coupling includes, for example, via a knot, protuberance, or other feature on tether 534 that cannot pass through an eyelet, loop, or other similar feature in distal-most anchor 526 through which tether 534 passes. Tether 534 then extends through an eyelet, loop or other similar feature on each of the anchors 526 so as to be slidably coupled with the anchors 526. In the embodiments shown, tether 534 exits each aperture 528, then enters the next-most-proximal aperture, passes slidably through a loop on an anchor 526, and exits the same aperture 528. By entering and exiting each aperture 528, tether 534 allows the plurality of anchors 526 to be deployed into tissue and cinched. Other configurations of housing 522, anchors 526 and tether 534 may alternatively be used. For example, housing 522 may include a longitudinal slit through which tether 534 may pass, thus allowing tether 534 to reside wholly within housing before deployment.

Expandable member 524 is an optional feature of anchor delivery device 520, and thus may be included in some embodiments and not in others. In other words, a distal portion of anchor delivery device 520 may include housing, contents of housing, and other features either with or without an attached expandable member. Expandable member 524 may comprise any suitable expandable member currently known or discovered in the future, and any method and substance(s) may be used to expand expandable member 524. Typically, expandable member 524 will be coupled with a surface of housing 522, will have a larger expanded radius than housing 522, and will be configured such that when it is expanded as housing 522 nears or contacts the valve annulus, expandable member 524 will push or press housing 522 into enhanced contact with the annulus. For example, expandable member 524 may be configured to expand within a space near the corner formed by a left ventricular wall and a mitral valve leaflet.

Generally, anchor delivery device 520 may be advanced into any suitable location for treating any valve by any suitable advancing or device placement method. Many catheter-based, minimally invasive devices and methods for performing intravascular procedures, for example, are well known, and any such devices and methods, as well as any other devices or method described in this application or later developed, may be used to advance or position delivery device 520 in a desired location.

Another implementation of a method for securing a plurality of tethered anchors 526 to a mitral valve annulus VA in a heart is now described with reference to FIGS. 10A-10F, 11, and 12A-12F. Referring first to FIG. 11 (a cross-sectional depiction of a heart H), in one embodiment a first guide catheter 550 is advanced in retrograde fashion through the aorta A, typically via access from a femoral artery. Guide catheter 550 is passed into the left ventricle LV of the heart and thus into the subannular space 552. Subannular space 552 is generally defined by the left ventrical wall, the mitral valve leaflets MVL, and cordae tendineae of the left ventricle and travels along most or all of the circumference of the valve annulus. Guide catheter 550 is generally a flexible elongate catheter which may have one or more curves or bends toward its distal end to facilitate placement of the distal end of catheter 550 in subannular space 552. The distal end of guide catheter 550 may be configured to be positioned at an opening into or within subannular space 552 such that subsequent catheter devices may be passed through guide catheter 550 into space 552.

Figure 11:
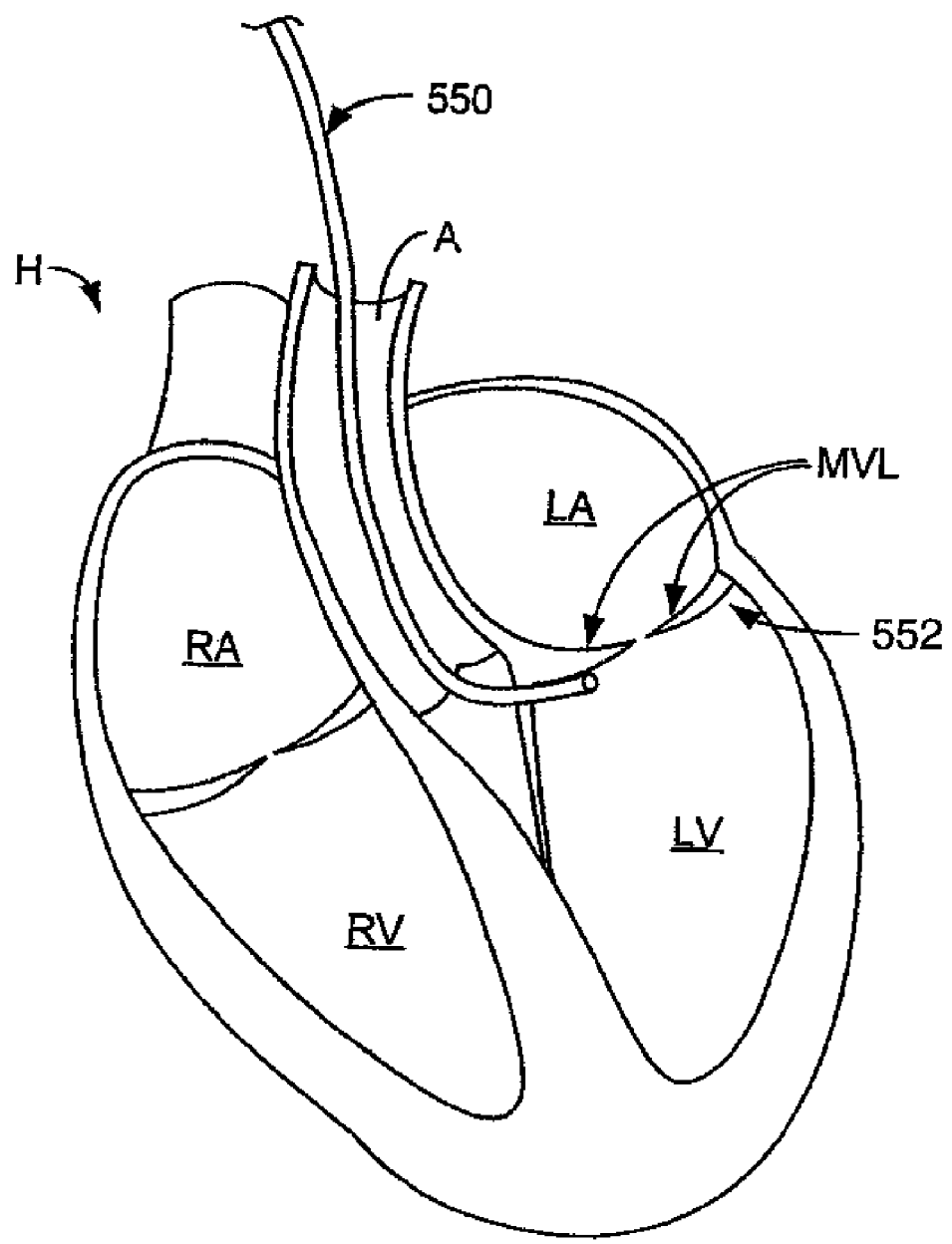
FIG. 11 shows a heart in cross-section with a guide catheter device advanced through the aorta into the left ventricle according to some embodiments.
Figure 12A:
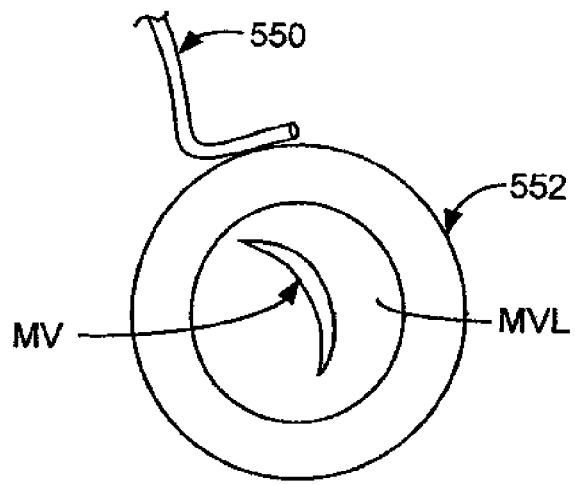
FIG. 12A-12F illustrate a method for advancing an anchor delivery device to a position for treating a heart valve according to some embodiments.
Figure 12B:
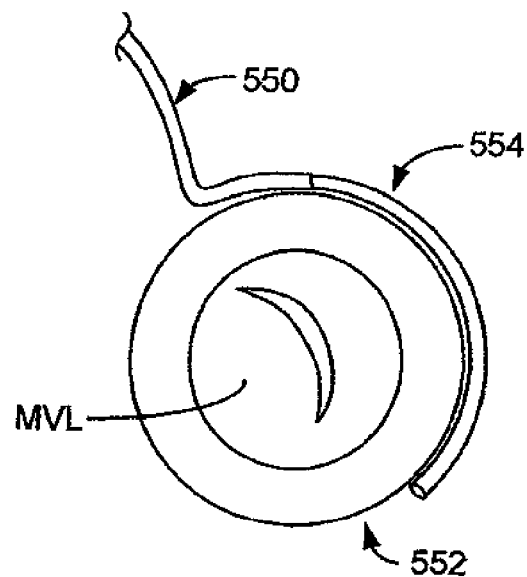

In FIGS. 12A-12F the mitral valve MV, including mitral valve leaflets MVL, is represented diagrammatically from an inferior perspective looking up. In FIG. 12A, guide catheter 550 is show extending up to or into subannular space 552, as in FIG. 11. As shown in FIG. 12B, a second guide catheter 554 may be advanced through first guide catheter 550 to pass through/along a portion or all of subannular space 552. In one embodiment this second guide catheter 554 is steerable (as described below with respect to FIGS. 13A and 13B, for example), to help conform second guide catheter 554 to subannular space 552.

Figure 12C:
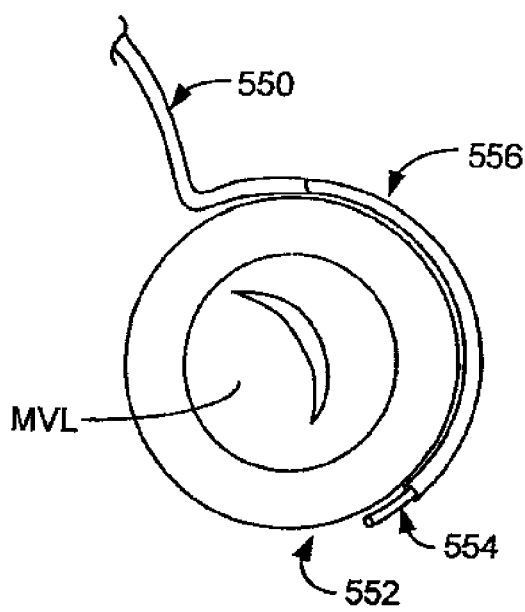
Figure 12D:
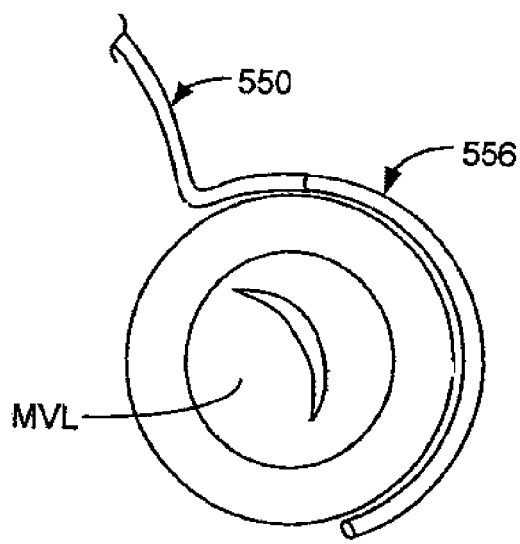
Figure 12E:
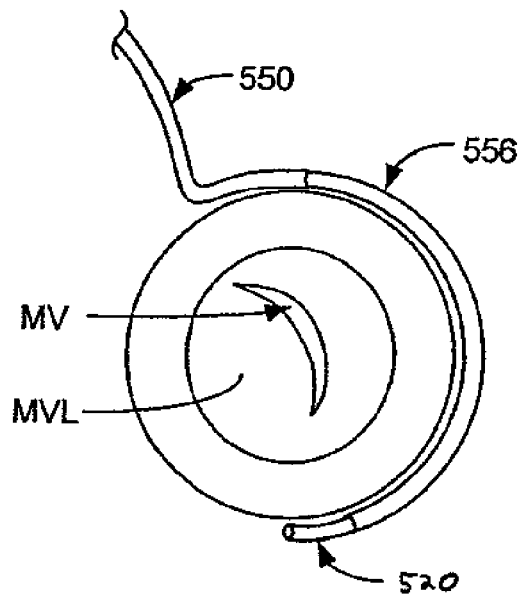
Figure 12F:
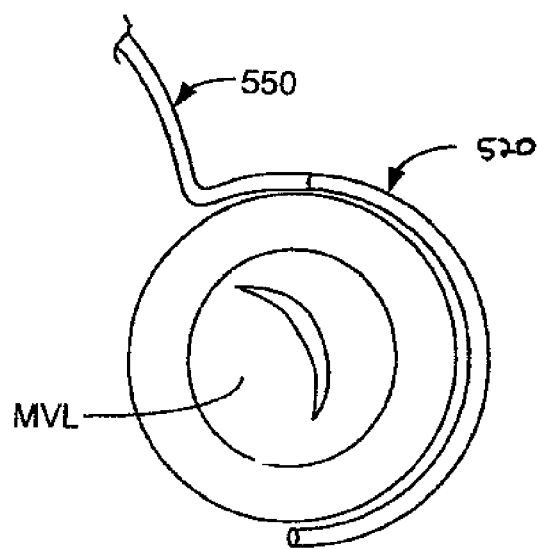

Next, as shown in FIG. 12C, a guide sheath 556 may be passed over second guide catheter 554 to extend along subannular space 552. Sheath 556 is generally a flexible, tubular member that can be passed over second guide catheter 554 and within first guide catheter 550. To enhance passage and exchange, any of these and other described catheter members, sheath members, or the like may be manufactured from and/or coated with one or more friction resistant materials. Once sheath 556 is in place, second guide catheter 554 may be withdrawn, as shown in FIG. 12D. As shown in FIG. 12E, an anchor delivery device 520 (described above) may then be advanced through sheath 556 to a desired position within subannular space 552. Sheath 556 may then be withdrawn, as in FIG. 12F, leaving anchor delivery device 520.

These are only exemplary methods for advancing an anchor delivery device to a position for treating a valve annulus, and any other suitable method or combination of devices may be used to position an anchor delivery device. In various alternative embodiments, one or more steps may be added, deleted or modified while achieving a similar result. In some embodiments, a similar method may be used to treat the mitral valve from a superior/right atrial position or to treat another heart valve. Additionally, other devices or modifications of the systems just described may be used in other embodiments.

Figure 10A:
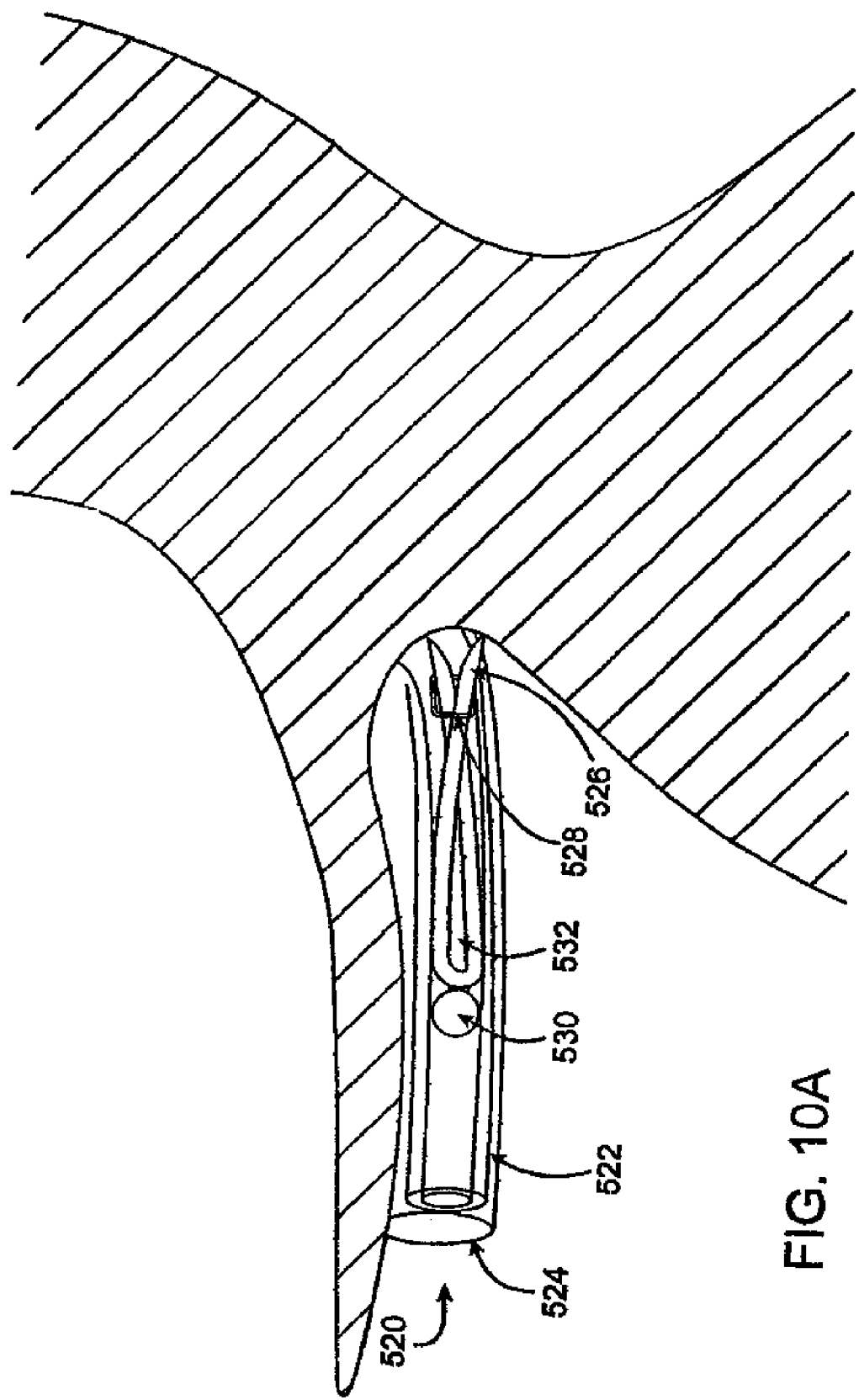

Referring now to FIG. 10A, anchor delivery device 520 is contacted with the valve annulus VA such that openings 528 are oriented to deploy anchors 526 into the annulus. Such orientation may be achieved by any suitable technique. In some embodiments, for example, a housing 522 having an elliptical cross-sectional shape may be used to orient openings 528. As described above, in some implementations contact between housing 522 and the valve annulus VA may be enhanced by expanding an expandable member 524 to wedge housing 522 within the corner formed by the left ventricular wall and the valve leaflets.

Figure 10D:
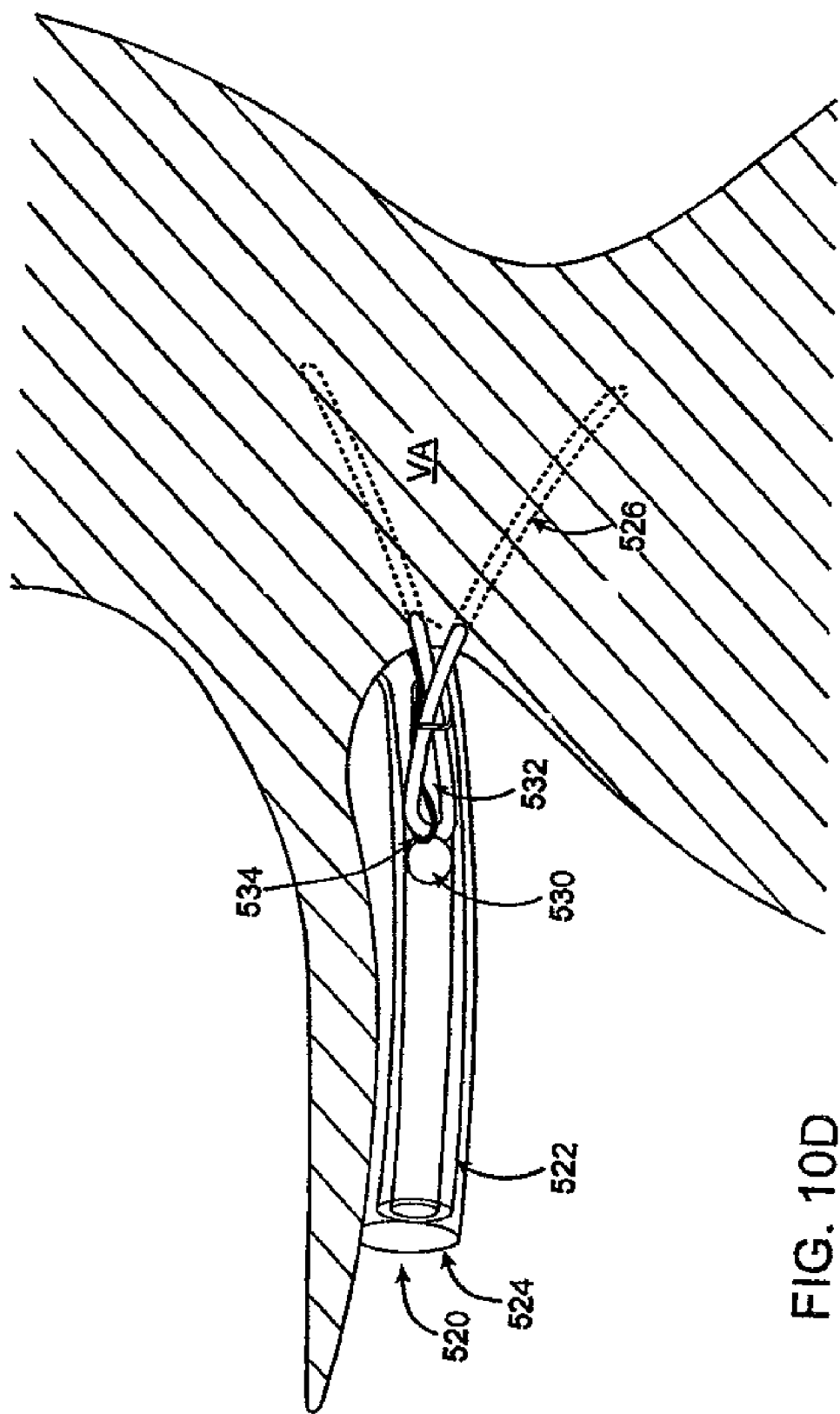

As shown in FIG. 10B, when delivery device 520 is positioned in a desired location for deploying anchors 526, anchor contacting member 530 is retracted to contact and apply force to a most-distal anchor 526 to begin deploying anchor 526 through aperture 528 and into tissue of the valve annulus VA. FIG. 10C shows anchor 526 further deployed out of aperture 528 and into valve annulus VA. FIG. 10D shows the valve annulus VA transparently so that further deployment of anchors 526 can be seen. As shown, in some embodiments anchors 526 include two sharpened tips (although they need not be) that move in opposite directions upon release from housing 522 and upon contacting the valve annulus VA. Between the two sharpened tips, an anchor 526 may be looped or have any other suitable eyelet or other device for allowing slidable coupling with a tether 534.

Referring now to FIG. 10E, anchors 526 are seen in their fully deployed or nearly fully deployed shape, with each tip (or "arm") of each anchor 526 having curved to form a circle or semi-circle. Of course, in various embodiments anchors 526 may have any other suitable deployed and undeployed shapes, as described more fully above. FIG. 10F shows anchors 526 deployed into and secured to the valve annulus VA and coupled with tether 534, with the distal-most anchor 526 fixedly coupled to tether 534 at attachment point 536 and other anchors 526 slidably coupled to tether 534.

Although the implementation just described employed anchor delivery device 520, any other suitable anchor delivery devices known, described herein, or later developed may also be used to secure a plurality of tethered anchors to a mitral valve annulus or other tissue. In some implementations, after the anchors have been secured to the tissue the anchor delivery device may be withdrawn. In other implementations, as described below, the anchor delivery device may be further employed in subsequent steps of a tissue tightening method. In some embodiments, the anchor delivery device is withdrawn through first guide catheter 550, and first guide catheter 550 is then withdrawn. In alternative embodiments, first guide catheter 550 may be withdrawn before the anchor delivery device is withdrawn.

In various embodiments, alternative methods may be used to urge an anchor delivery device into contact with the valve annulus. For example, in some embodiments a magnet may be coupled with the anchor delivery device, and another anchor may be disposed within the coronary sinus, in proximity to the first magnet. The two magnets may attract one another, thus pulling the anchor delivery device into greater contact with the annulus. Various embodiments may also include visualizing the annulus using a visualization member coupled with or separate from the anchor delivery device. In some embodiments, the tether is a strip of detachable, biocompatible material, such as DACRON® polyester, that is coupled with the anchor delivery device. The anchors are driven through the strip, which detaches to affix to the valve annulus via the anchors. In other embodiments, the tether is a detachable, biocompatible, distal portion of the guide sheath through which the anchors are driven, and that portion of the guide sheath remains attached to the annulus via the anchors.

Referring again to FIG. 10F, after the plurality of tethered anchors 526 has been secured to the valve annulus, tension may be applied to tether 534 to cinch tether 534 and thereby tighten the annulus, thus reducing valve regurgitation. In some embodiments, valve function may be monitored by any suitable method, such as echocardiogram and/or fluoroscopy, and tether 534 may be cinched, loosened, and adjusted to achieve a desired amount of tightening as evident via the employed visualization technique(s) or monitored function(s). When a desired amount of tightening is achieved, tether 534 is then fixedly coupled to a most-proximal anchor 526 (or to two or more most-proximal anchors 526), using any suitable technique. By "fixedly coupled," here it is meant that tether 534 is coupled to most-proximal anchor or anchors 526 in a manner that prevents tether 534 from sliding through or past most proximal anchor or anchors 526 in the direction of more distal anchors 526. Suitable techniques for fixedly coupling tether 534 to most proximal anchor or anchors 536 include but are not limited to use of adhesives, tying, knotting, crimping the anchor, deforming the anchor, clamping the tether to the anchor, and providing a locking feature on the tether that, for example, cannot pass through an eyelet, loop, or other similar feature in the most proximal anchor or anchors. Some of these techniques are discussed in additional detail below.

Still referring to FIG. 10F, after tether 534 has been fixedly coupled to most proximal anchor or anchors 526, tether 534 is cut proximal to the most-proximal anchor 526, thus leaving the cinched, tethered anchors 526 in place along the valve annulus VA. Tether 534 may be cut via any technique such as, for example, with a cutting member coupled with housing 522. Techniques and devices for cutting tether 534 are discussed in additional detail below.

In some embodiments it may be advantageous to deploy a first set of anchors 526 along a first portion of a valve annulus VA, cinch the first set of anchors to tighten that portion of the annulus, move the delivery device 520 to another portion of the annulus (typically the opposite side), and deploy and cinch a second set of anchors 526 along a second portion of the annulus. Such a method may be more convenient in some cases than extending delivery device 520 around all or most of the circumference of the annulus, and may allow a shorter, more maneuverable housing 522 to be used.

In some embodiments the steps of securing the anchors to the tissue, applying tension to the tether, fixedly coupling the tether to the most proximal anchor or anchors and cutting the tether are performed by the same device. Any or all of these steps may be performed intravascularly. In other embodiments different devices may be used to perform each step or combinations of these steps. For example, in some embodiments, a first device deploys and secures the anchors to tissue and one or more other devices performs the termination steps of applying tension to the tether, fixedly coupling the tether to one or more of the most proximal anchors, and cutting the tether. Devices that perform one or more of these termination steps are described herein as termination devices.

If an initial step is performed by a first device and a subsequent step is to be performed by a second device such as a termination device, it may be necessary to load the tether into the second device. Both devices can be intravascular devices. Generally such loading will occur after the tethered anchors have been secured to tissue. The tether may be loaded into the second device prior to introducing the second device into the body, e.g., into the vasculature. Alternatively, the tether may be loaded into the second device in situ (e.g., intravascularly).

Figure 14A:
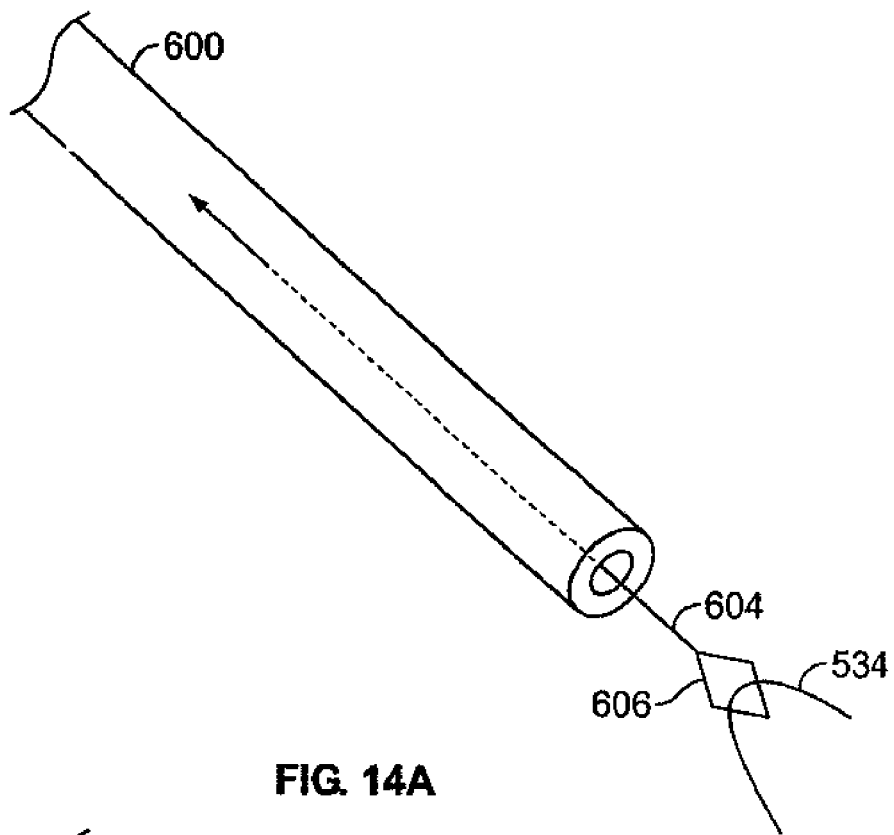
FIGS. 14A and 14B are illustrative variations of devices and methods for loading tethers into catheters.
Figure 14B:
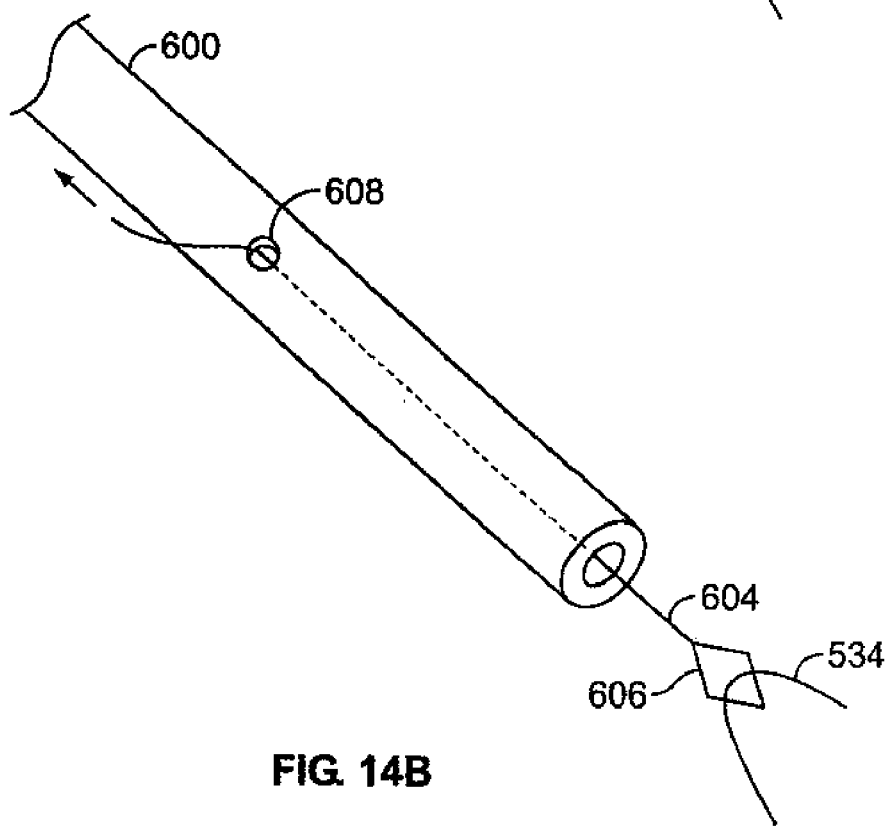

Referring now to FIGS. 14A and 14B, in some embodiments, tether 534 is loaded into termination device 600 using a lasso 604 (e.g., a threading device) which comprises a loop 606 at one end. One end of tether 534 (not shown) is coupled to a plurality of anchors that have been secured to tissue by, for example, the methods and/or devices described herein. The other end of tether 534 is threaded through loop 606 of lasso 604. Lasso 604 may then be pulled along the axis of termination device 600 (FIG. 14A) or, in alternative implementations, through a side hole 608 in termination device 600 (FIG. 14B) to load tether 534 into termination device 600. Termination device 600 may then perform one or more termination steps. Lasso 604 may be made from, for example, conventional materials such as wire, suture, cable, string, or a monofilament. The lasso may comprise a loop (as show in FIGS. 14A and 14B), a hook, a coil, a tube, an elongate element with hole, or any other structure or material that can "grab" the tether.

Figure 15A:
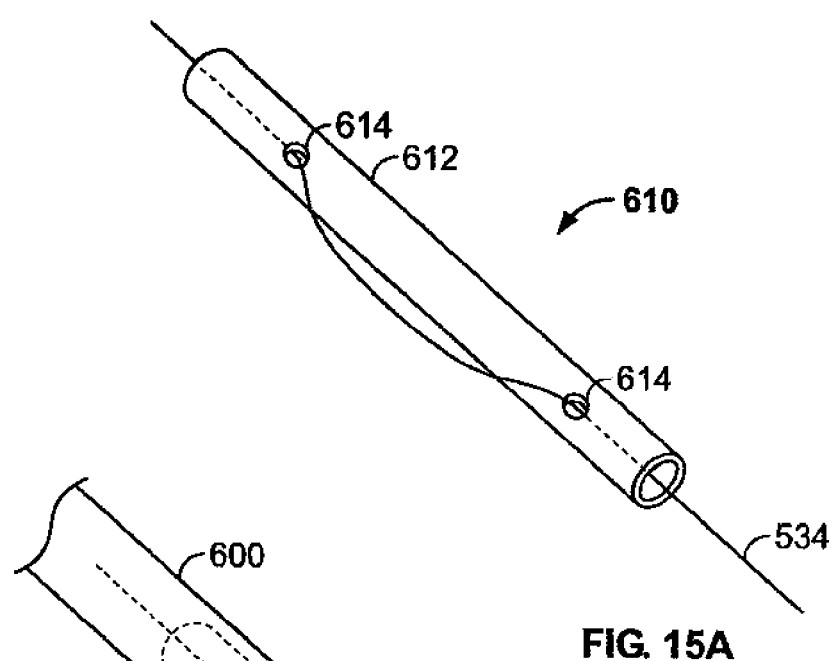
FIGS. 15A-H are additional variations of devices and methods for loading tethers into catheters.
Figure 15B:
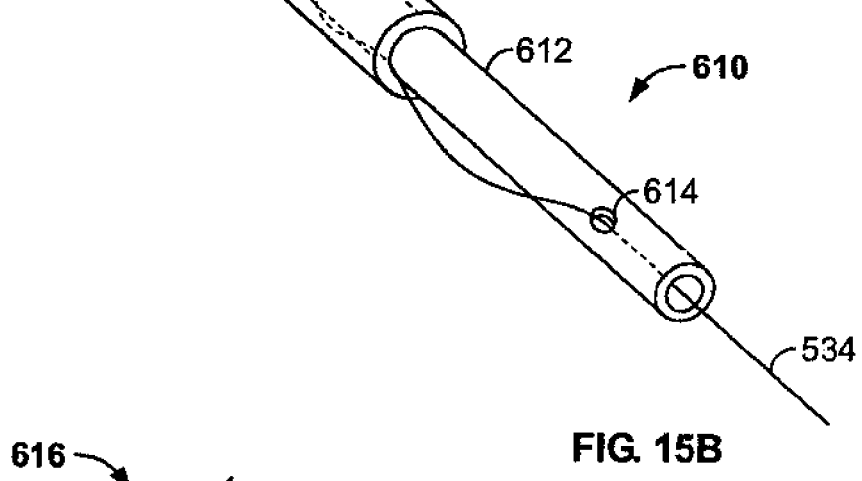
Figure 15C:
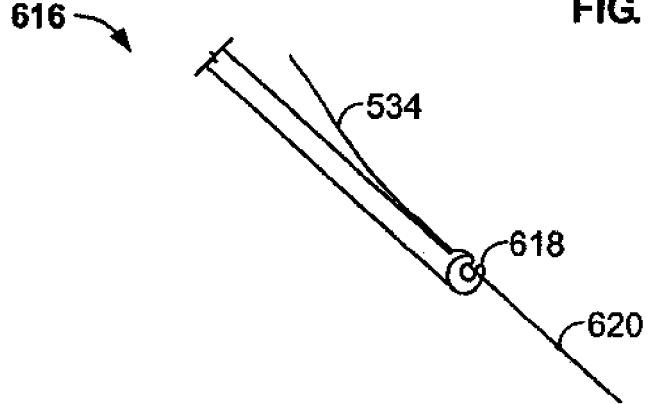

In other embodiments (e.g., FIGS. 15A-15H) the tether is loaded into a termination device by threading the tether through one or more features in a rod and then inserting the rod into the termination device. These rods may be of a length that facilitates easy handling, if applicable, and sized to interface with the termination device. Preferably, the rods are 60-150 cm. The rods may be composed of any material which will perform the function of handling the tether, including metal and plastic (e.g., nylon, PEBAX, PEEK, Fluoro polymer like PTFE, PET, or polyethylene, polypropylene, or metal braided polymer). The features in the rod may be, for example, holes, openings, indents, grooves, and slits. The rod may remain in the termination device or be subsequently removed. In some implementations a knot may be tied at the proximal end of the tether to prevent the tether from slipping out of the rod. In some implementations the rod has a passage from one end of the rod to a first opening in a side of the rod and another passage from the other end of the rod to a second opening in a side of the rod. The tether may be threaded through these passages. In FIG. 15A, for example, rod 610 comprises a tube 612 with side holes 614. Tether 534 is threaded through one end of the tube, through the two side holes, and through the other end of the tube. Rod 610 is then inserted into termination device 600 (FIG. 15B).

In other implementations, (FIG. 15C), rod 616 comprises a C-shaped feature 618 through which tether 534 may be threaded. Rod 616 is then inserted into a termination device similarly to the example shown in FIG. 15B. Feature 618 may be, for example, a C-shaped fastener that snaps around tether 534. In these implementations, tether 534 may comprise a knot or other suitable feature 620 that cannot pass through C-shaped feature 618, thus improving the ability of rod 616 to pull tether 534 into a termination device.

Figure 15D:
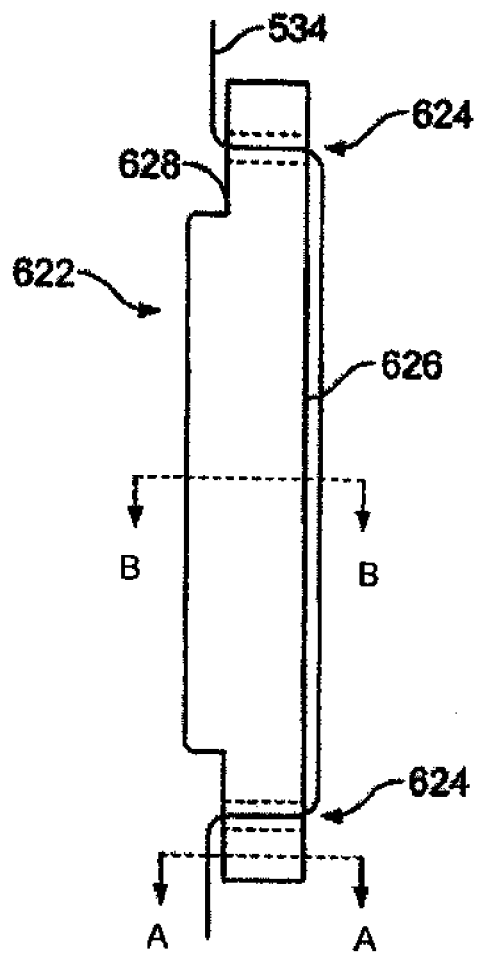
Figure 15E:
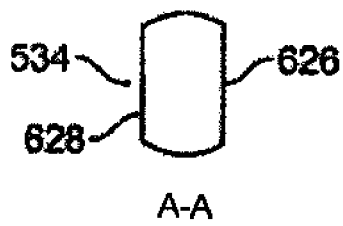
Figure 15F:
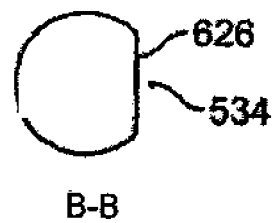
Figure 15G:
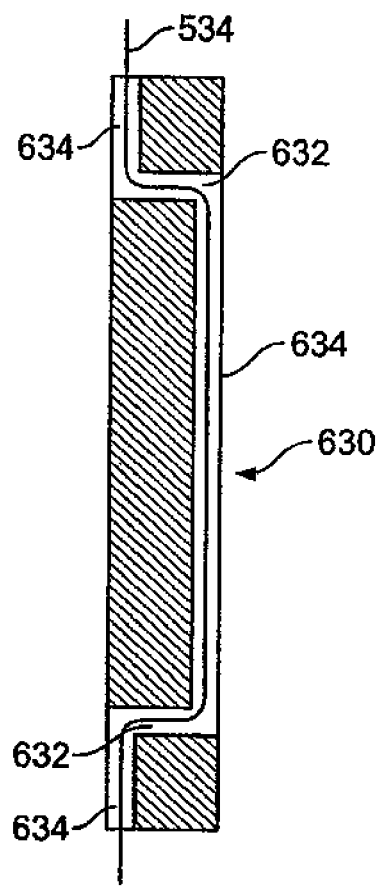
Figure 15H:
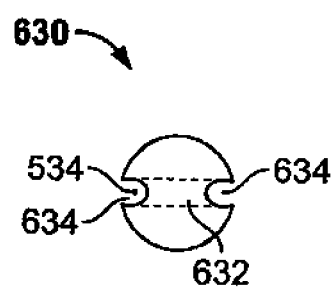

In the implementations shown in FIGS. 15D-15F, rod 622 comprises through—holes 624 oriented approximately perpendicular to a long axis of the rod and flat portions 626 and 628 oriented approximately parallel to the long axis of the rod. Tether 534 runs along flats 626 and 628 when it is threaded through holes 624. This configuration allows rod 622 and tether 534 to remain within a round profile. In the implementation shown in FIGS. 15G and 15H, rod 630 comprises holes 632 oriented approximately perpendicular to a long axis of the rod and grooves 634 oriented approximately parallel to the long axis. Tether 534 runs along grooves 634 when threaded through holes 632. In these implementations also, the rod and tether may remain within a round profile. Other orientations of holes, flats, and grooves may also be suitable in these implementations.

After a plurality of tethered anchors have been secured to tissue, in some embodiments the device used to deploy and secure the anchors may be used to apply tension to the tether to tighten the tissue. In other embodiments, a termination device into which the tether has been loaded may be used to apply the tension. In some embodiments, the deployment or termination device is advanced along the tether to a location at or near the proximal end of the tethered anchors. The device may then be used to apply an opposing force to the most proximal anchor while tension is applied to the tether to cinch it. The opposing force has a component counter to the tensioning force applied to the tether, and thus stabilizes the most proximal anchor as the tether is cinched. The opposing force may be applied, for example, by contacting the most proximal anchor with the deployment or termination device. The deployment or termination device may be an intravascular device.

During a tissue tightening procedure, e.g., an annuloplasty procedure, a locking or fixing feature should be applied to the cinching tether to fix its length so that tension is maintained. If anchors are being secured to the tissue, and the cinching tether is threaded through the anchors to tighten the tissue via the anchors, the end of the cinching tether should not slide through an eye of the most proximal anchor.

Various fixing or locking features and methods can be used to fix the end of the cinching tether so that it does not slip through the most proximal anchor. These features and methods can be used intravascularly. Several types of locking features can be used. These locking features generally fall into three categories: features that cannot slide; features that can slide until they hit a stop; and features that are designed to slide somewhat before locking, relieving some tension in the tether. For the latter type of features, an extra length of tether is provided to accommodate the slippage. The locking features can be applied to the most proximal anchor itself, or they can be applied to the tether. In addition, the tether can be fixedly coupled to the most proximal anchor by deforming the second anchor, e.g., by use of a device that can bend or twist the second anchor.

Figure 16A:
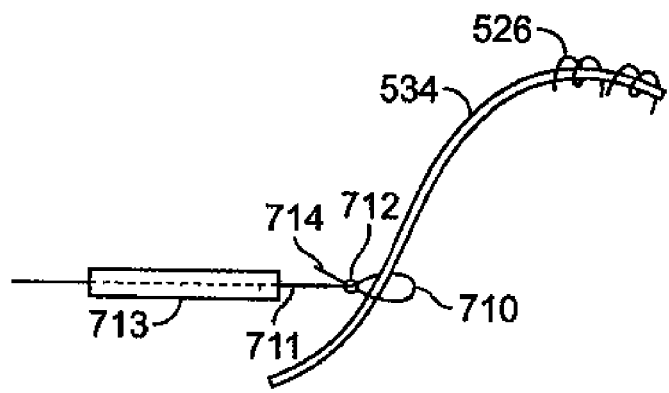
FIGS. 16A-E are illustrative examples of termination devices and methods utilizing knots to fix a tether in place.

Knots can be used as locking features for tethers. One type of knot that can be used is a slip knot positioned near the most proximal anchor, as illustrated in FIG. 16A. Tether 534 is cinched until the tissue shape (e.g., valve tissue) is as desired. The proximal end of the tether is threaded through a loop 710 of a tie 711 having slip knot 712. The loop 710 is slid over tether 534 in a distal direction until it reaches or is close to the most proximal anchor. Tie 711 is pulled to slide through 713 to tighten the knot around tether 534 such that the tether is locked in place and will not slip past the most proximal anchor, e.g., through an eye of the most proximal anchor. Many different types of slip knots may be used, including Roeder's knots. In some variations, a secondary slip knot can be applied to the end, slipping portion and/or non-slipping portion of tie 711 to further lock knot 712 in place. Tie 711 can be passed inside a catheter 713. In another variation, tether 534 and tie 711 are joined with knots, including half knots, to further lock knot 712 in place.

Figure 16B:
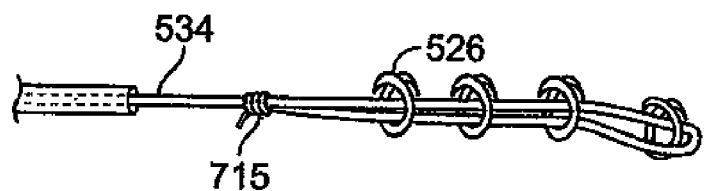

In other variations, as shown in FIG. 16B, tether 534 can be looped through anchors 526, with a slip knot 715 positioned near most proximal anchor closing the loop. Tether 534 can be looped through the eye of most distal anchor and then threaded through other anchors in any suitable fashion that allows tension on the tether 534 to be adjusted as necessary. For example, as illustrated in FIG. 16B, tether 534 can be looped through most distal anchor, then both strands can be threaded through the remaining anchors, except for the most proximal anchor. On the most proximal anchor, just one of the strands may be threaded through, while the other strands goes around the last anchor. Thus, the anchor forces the two strands of the knot to exit at angles relative to one another so that when tension is exerted on those strands, a knot such as the Roeder's knot self tightens. Slip knot 715 can be pushed to cinch tether 534 as desired and lock tether 534 into place. A knot pusher can be used to simultaneously cinch and push the knot. As the knot is pushed, tether 534 adjusts, sliding through the most distal anchor such that two sides of the loop of tether 534 are approximately equal in length. The force of tissue expanding outward can cause knot 715 to tighten further. For the most distal anchor, tether 534 can be threaded through a guided feed (not shown), such as a slotted device coupled to most distal anchor, to lessen friction as the tether 534 is cinched. A secondary tie having a secondary slip knot, for example, similar to tie 711 as shown in FIG. 16A, can be applied to tether 534 to help tighten knot 715. In addition, two knots (not shown) can be used for the variation shown in FIG. 16B. The tether can include a loop having a first slip knot positioned proximal the most proximal anchor and a second slip knot positioned distal the most distal anchor. The two slip knots positioned at opposite ends of the plurality of tethered anchors can be used to adjust the length and tension in the loop of the tether.

Figure 16C:
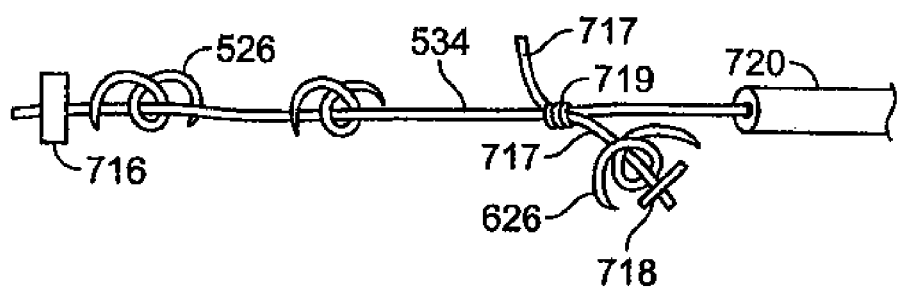

In other variations illustrated in FIG. 16C, tether 534 can be threaded through all anchors 526 except the most proximal anchor 626. At the distal end of tether 534 is a block 716, e.g., a knot or a washer or the like, to prevent the most distal anchor from passing over the most distal end of tether 534. A second cinching cable 717 is threaded through only the most proximal anchor 626 and has block 718, e.g., a knot or a washer or the like, to prevent the most proximal anchor 626 from passing over the most proximal end of cable 717. Cable 717 is used to tie a slip knot 719 around tether 534 just proximal the second most proximal anchor, such that knot 719 can slide along tether 534. Knot 719 is pushed along tether 534 in a distal direction to cinch tether 534, e.g., by pusher 720. Expanding force of tissue can further tighten knot 719.

Figure 16D:
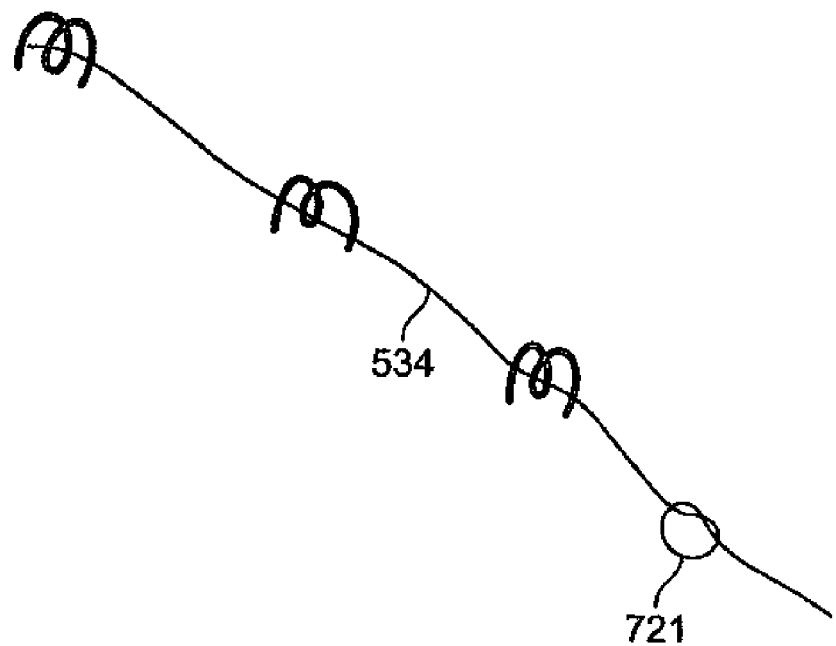
Figure 16E:
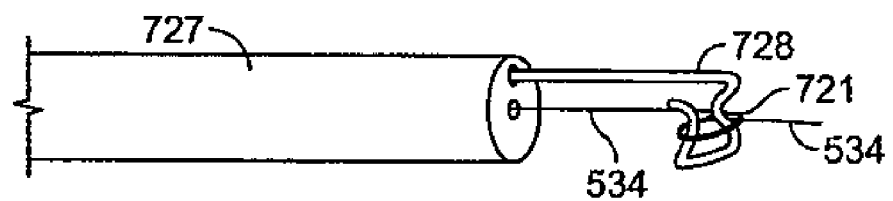

In other variations as shown in FIG. 16D, a sliding half knot 721 proximal of the most proximal anchor is passed distally down the length of tether 534 to the most proximal anchor. Half knot 721 is held open as it is slid distally down the length of tether 534. When half knot 721 is in the desired position, the device holding the knot open is released, and a pusher may push on the knot in a distal direction to tighten the knot. The knot can be held open by any suitable method. For example, as illustrated in FIG. 16E, pusher 727 can include a retractable member 728, e.g., a wire form made from any suitable material such as a nickel titanium alloy, that holds half knot 721 open. When half knot 721 is positioned as desired to lock tether 534 in place, retractable member 728 is retracted to release half knot 721. Alternatively, knot 721 can be held open by sliding the knot around a round or elliptical roller (not shown) having a large enough cross-sectional diameter to prevent the knot from becoming tight and therefore not sliding. Knot 721 can also be held open by placing pins (not shown) in the two loops of the half knot such that the loops, and therefore the knot, cannot tighten. In some variations knot 721 itself is large enough that it cannot pass through the eye of most proximal anchor. In other variations, there is a washer or other blocking object 722 slidably coupled to tether 534 that cannot pass through the eyelet of most proximal anchor. For any of the variations including sliding a half knot, a mechanical feature that holds the tether slack before, during, or after sliding the half knot can be included. By holding the tether with sufficient slack, the knot generally will not tighten.

As shown in FIG. 16D, an additional cinching cable 723 having a knot or other impediment 724 on its distal end can be threaded through the most proximal anchor so that the cinching cable 723 cannot pass through the most proximal anchor when pulled in a proximal direction. Half knot 721 can then be tied with both cinching cable 723 and tether 534, creating a bulkier knot. In some variations, both cinching cable 723 and tether 534 are passed through washer or blocking object 722. In other variations, two tethers can be threaded through all anchors. The two tethers can then used to make a half knot. Tube 727 can be pushed against half knot 721 to push the knot in a distal direction to create a fully locked knot, holding the tethers in place. Tube 727 can have a saddle (not shown) to aid in pushing. In some variations, the cinching tether or tethers can exit the side of pushing tube 727.

Figure 17:
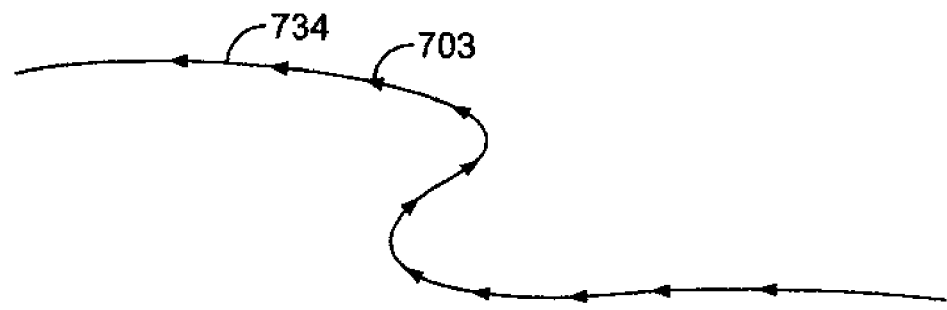
FIG. 17 illustrates an example of a termination method and device that utilizes a tether comprising spaced apart protrusions to maintain tension on the tether.
Figure 18A:
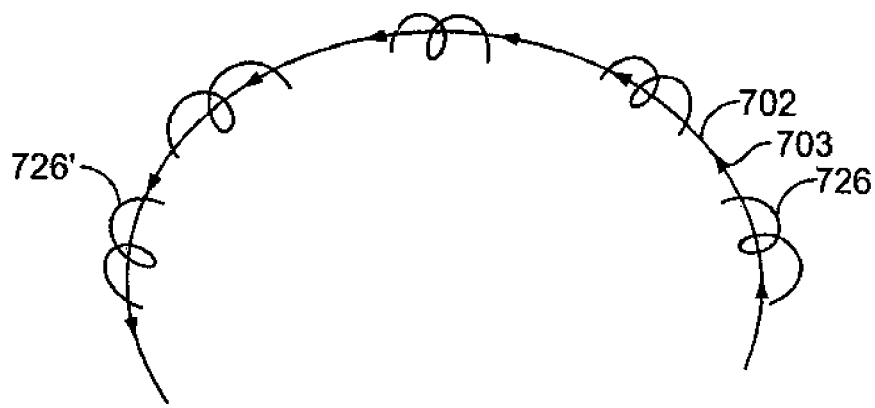
FIGS. 18A-B illustrates additional examples of termination methods and devices that utilize a tether comprising spaced apart protrusions to maintain tension on the tether.
Figure 18B:
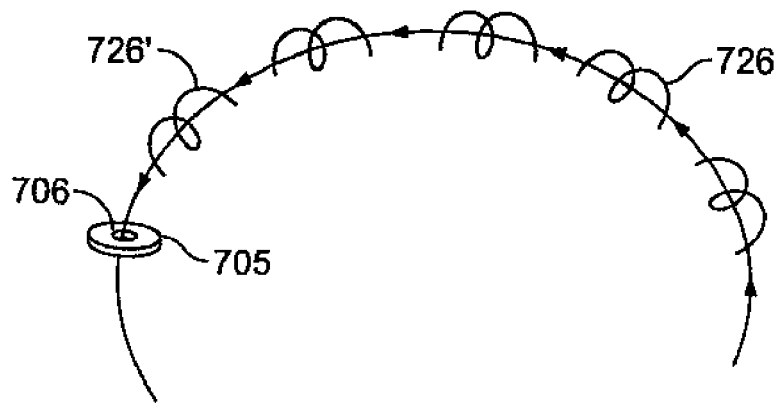

As shown in FIG. 17A, tether 734 can have protrusions 703 that allow tether 734 to slide through anchors 726, e.g., through anchor eyelets, in one direction, but not in the opposite direction. Protrusions 703 can be arrow-shaped, V-shaped, cone-shaped, triangular, or have any other suitable shape or geometry that allows them to pass in one direction through an opening but not in the reverse direction. Alternatively, protrusions 703 can comprise other shapes or objects, such as knots. In some variations, as shown in FIG. 18A, the most proximal anchor 726' has an eyelet with a reduced cross-sectional dimension such that protrusions 703 can pass as tether 734 is pulled in a proximal direction through the eyelet of anchor 726', but not when tether 734 is pulled in a distal direction. Tether 734 can be ratcheted into a desired tension as sequential protrusions 703 are passed through the most proximal anchor 726'. In other variations, as shown in FIG. 18B, a collar 705 is positioned along tether 734 proximal to most proximal anchor 726'. Tether 734 is threaded through an opening 706 in collar 705. Opening 706 can expand slightly such that protrusions 703 can pass through opening 706 when they are pulled through in a proximal direction, but not when pulled in a distal direction. For example, opening 706 can be a generally fixed opening and protrusions 703 can be of such a shape as to pass in the proximal direction through opening 706 but not in the distal direction. Thus, as sequential protrusions 703 are passed through opening 706, tether 734 is cinched tighter and locked into place.

Protrusions 703 can be of any type and provided by any suitable method. For example, tether 734 including protrusions 703 can be formed of sheet metal, and then processed, e.g., by electropolishing or any other suitable technique, to remove sharp corners and edges. Tether 734 and protrusions 703 can also be formed of plastic, e.g., a plastic comprising a TEFLON® fluoropolymer, or polyester. Alternatively, protrusions 703 can be added to tether 734 in a separate step, e.g., by threading cones onto a suture and fixing the cones in place along the suture at defined intervals. The cones can be bonded or otherwise attached to or coupled with the suture.

Other methods for fixing the end of a tether such that tension is maintained include threading the tether through a path having numerous twists, turns, and or bends such that slippage of the tether is prevented.

Figure 19A:
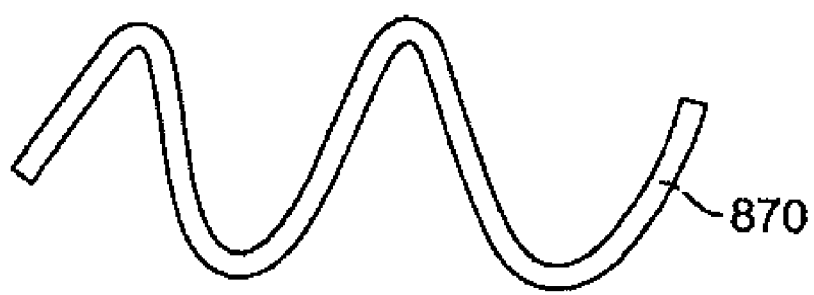
FIGS. 19A-C show variations of termination devices and methods that include threading a tether through a tube that can be straight (to allow the tether to slide) or kinked (to lock the tether into place).
Figure 19B:
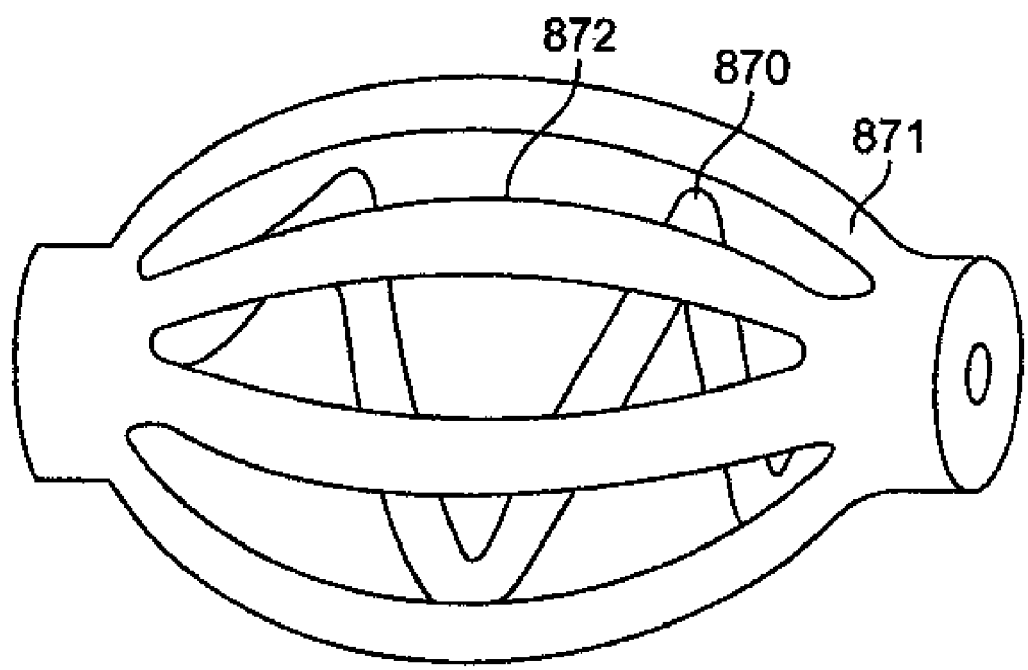
Figure 19C:
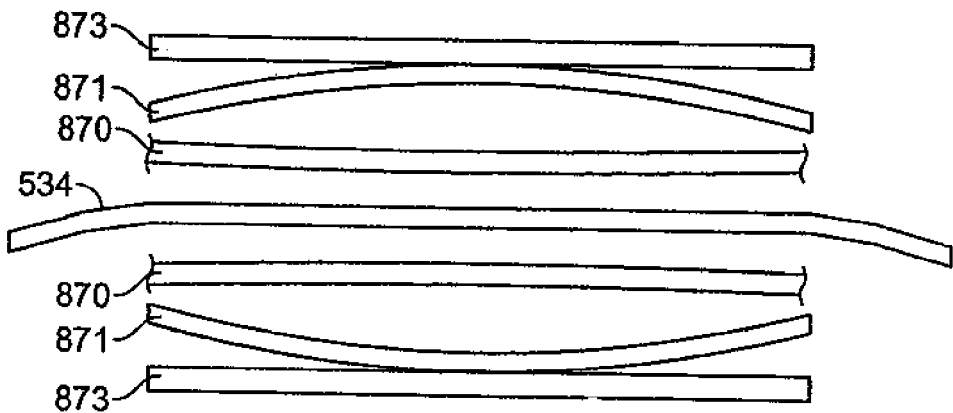

A self-kinking tube can be used to clamp or lock a tensioned tether into place during termination. As shown in FIG. 19A, tube 870 that has been pre-kinked along its length can be provided. A force can be applied to tube 870 to compress it axially to maintain its kinked state, e.g., by providing a spring extending between the ends of the tube. As illustrated in FIG. 19B, a spring 871 having spring elements 872 can be provided. Spring 871 can be placed in a collinear arrangement with tube 870 such that ends of spring 871 are coupled to the ends of tube 870. Thus, spring 871 can assist in applying axial force to tube 870 to maintain its kinked state. For example, spring 871 can be placed over tube 870, or alongside and generally parallel with tube 870. A second straight tube 873 (e.g., a catheter) can be provided which fits over spring 871 by compressing spring elements 872 inwardly (FIG. 19C). This causes spring 871 to elongate, and therefore to elongate kinked tube 870 into a generally straightened state (FIG. 19C). Tether 534 can be threaded through straightened tube 870 such that tether 534 can move back and forth through tube 870 freely. When it is desired to fix tether 534 during termination, the force causing tube 870 to be at least partially unkinked can be released, allowing tube 870 to be restored to its kinked state to lock tether 534. For the examples illustrated in FIGS. 19A-C, second tube 873 can be removed from spring 871, thus allowing spring elements 872 to recover to their curved state, reducing the length of spring 871, and causing tube 870 to recover to its kinked state. Once tube 870 is kinked, tether 734 can no longer freely move and is fixed into place. Tube 870 can be made of any material suitable for use inside the human body and that can be transferred between a straightened and kinked state, such as nylon, PEBAX®, polyurethane, polyethylene terephthalate, polyethylene, polypropylene or polyetheretherketone. Spring 871 can comprise any spring material suitable for use within the human body, such as stainless steel, titanium, or nickel titanium alloys or polyetheretherketone. Although spring 871 has been depicted as having a basket shape for purposes of illustration, spring 871 can have any suitable shape.

Figure 20A:
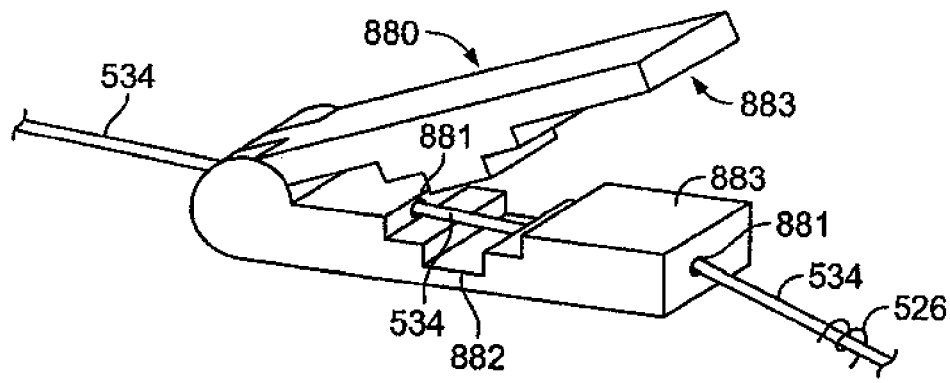
FIGS. 20A-B show variations of termination devices and methods that include threading a tether through a clamp that forces the tether into a tortuous path to fix the tether in place.
Figure 20B:
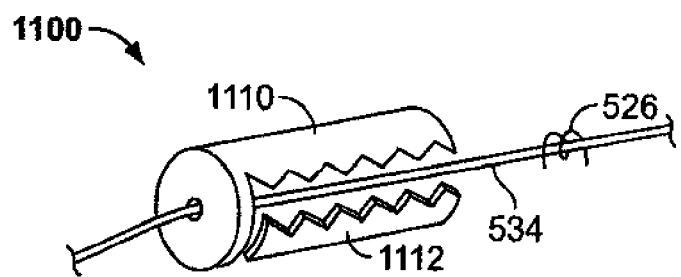

The tether can be threaded through a clamp to lock it into place during termination. Clamping can involve applying a force to cause two surfaces (e.g., clamp jaws) of a locking feature together to clamp the tether. Clamping can also involve applying a force to separate two surfaces of a locking feature, passing the tether between the surfaces, and releasing the force to clamp the tether between the surfaces. In some variations, the surfaces of the clamp jaws will be at least partially roughened, toothed, or made to have adhesive properties to hold the tether. For example, as illustrated in FIG. 20A, two sides of a clamp 880 can form an interlocking profile 882, e.g., a stepped profile or other profile having corners. Tether 534 is threaded through holes 881 such that tether 534 traverses profile 882 when clamp 880 is open. As clamp 880 is closed, tether 534 is forced to follow the tortuous path imposed on it by the interlocking profile 882. Clamp 880 can be closed by any suitable mechanism, such as with a closure, or with a spring hinge. If clamp 880 is closed by a spring hinge, it can be propped open using a propping element (not shown) while tether 534 is threaded through holes 881, and before it is desired to fix tether 534 into place. When it is desired to lock down tether 534 during termination, the propping element can be removed. Alternatively, a spring hinge can have an open position, allowing tether 534 to slide freely through clamp 880. When it is desired to fix the tether, the spring hinge can be snapped into a closed position. Clamp 880 can have any suitable interior surfaces 883 such that when the clamp is closed, surfaces 883 prevent tether 534 from slipping. In other embodiments, the clamp can have numerous structural features along its length. For example, as illustrated in FIG. 20B, clamp 1100 has a saw-toothed surface on inner surfaces of both jaws 1110 and 1112 along its longitudinal axis, and tether 534 is threaded through clamp 1100 along its longitudinal axis. Clamp jaws 1110 and 1112 can be locked together when it is desired to fix tether 534 upon termination by any suitable mechanism, such as by using a hinge or clamping mechanism. Besides the stepped surface illustrated in FIG. 20A and the saw-toothed surface illustrated in FIG. 20B, other suitable clamping surfaces can be used, including roughened, notched, etched, scored, and the like.

Figure 21A:
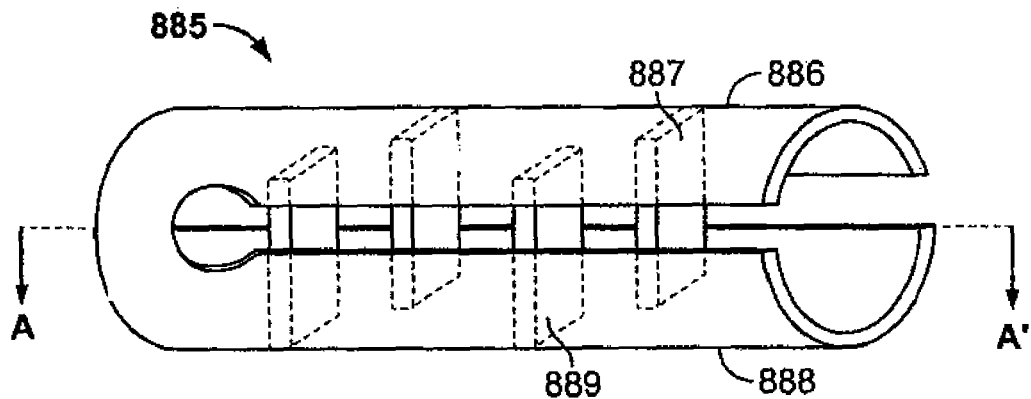
FIGS. 21A-C show additional variations of termination devices and methods that include threading a tether through a clamp that forces the tether into a tortuous path to fix the tether in place.
Figure 21B:
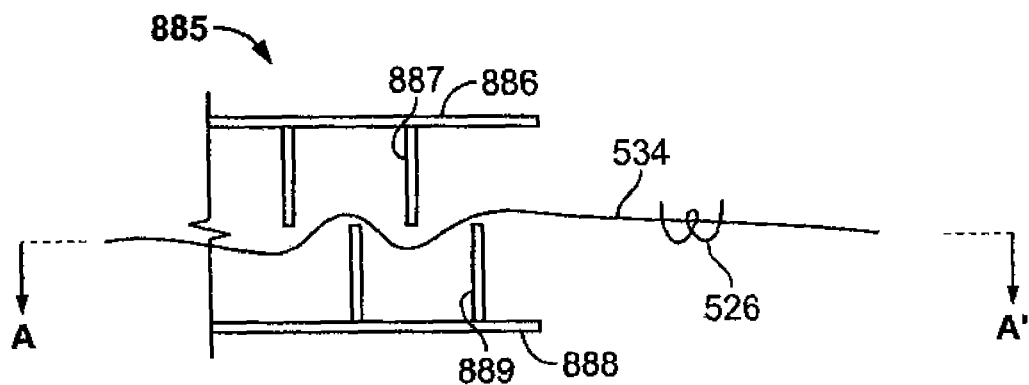
Figure 21C:
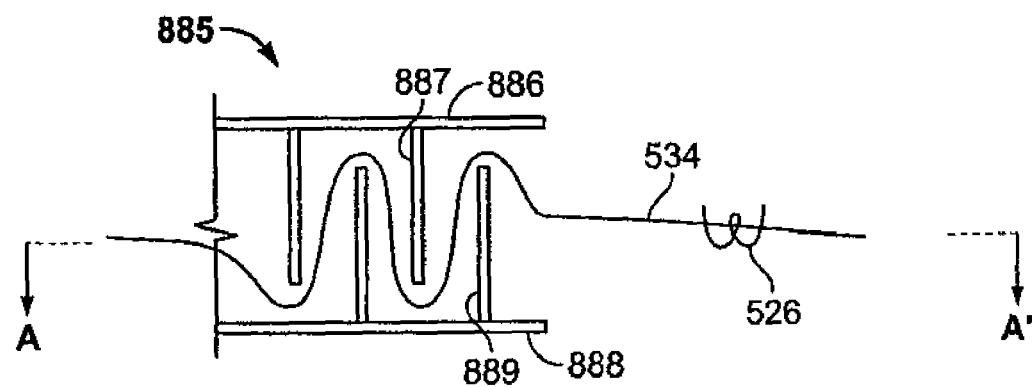

FIG. 21A illustrates additional examples of toothed clamping devices that can be used to lock the tether during termination. In FIG. 21A, clamp 885 having first side 886 with protruding features 887 attached thereto and second opposing side 888 with protruding features 889 attached thereto is provided. Protruding features 887 and 889 are placed in an alternating manner along the long axis A-A' of clamp 885 and extend into the interior volume of clamp 885 such that the only path down the long axis is tortuous when clamp 885 is closed. When clamp 885 is opened (FIG. 21B), a generally unobstructed path down the long axis A-A' of the interior of clamp 885 exists. Thus tether 534 can be threaded through axis A-A' of clamp 885 in its opened state. When clamp 885 is closed (FIG. 21C), tether 534 will be forced in a tortuous path by protrusions 887 and 889, and will thus be fixed into place. In some variations, the rest state of clamp 885 is closed, and held open, e.g., by a propping mechanism, to thread tether 534 through clamp 885 and to adjust tension on tether 534. When it is desired to lock tether 534, clamp 885 is allowed to close, e.g., by retracting the propping mechanism. In other variations, the clamp is open during its rest state so that tether 534 can easily slide through its interior. When it is desired to fix tether 534, an external element clamps or deforms clamp 885 such that it is in a closed state and protrusions 887 and 889 lock tether 534.

The tether can be threaded through a coil or spring 890 in a direction generally orthogonal to the expandable direction of the spring.

Other clamping schemes can be used to lock a tether into place during termination. Several factors can influence how well a clamp holds a tether. These include surface finish, surface area, elasticity of material, configuration of the tether in the clamp, and clamping force. For example, surfaces that are roughened, toothed, scored, etched, textured, or sticky (i.e., have adhesive properties) all increase the holding force of the clamp. In addition, a larger clamping surface area generally increases the holding force. In some cases, more elastic materials used for clamp jaws can provide increased hold on cinching tethers. Designing a clamp so that it holds the cinching tether in a bent, folded, curved, or other generally nonlinear configuration can increase the holding force. A higher clamping force applied to the tether via clamp jaws increases the holding force of the clamp. All of these variables can be adjusted according to clamp design to provide desired features, e.g., size, cost, ease of use, installation method, and biocompatibility for area or type of use. Certain clamp features may be desired for use with certain tether types or materials or diameters, for use with certain tension ranges, or for certain tissue types. Clamping devices can be used to clamp onto the tether such that the tether cannot move past the most proximal anchor. Alternatively, clamping devices can be used to clamp the tether to the most proximal anchor.

Figure 22:
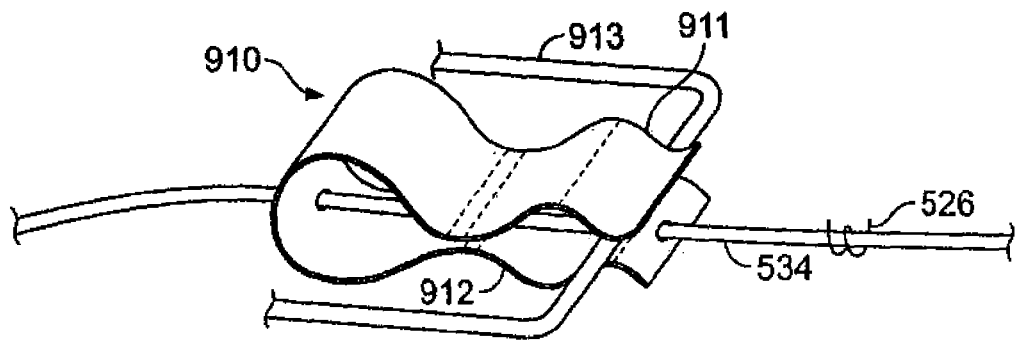
FIG. 22 shows a variation of a termination device utilizing clips or spring clips to lock a tether.

A clamping device, such as a clip, formed of a single piece of metal can be provided to lock the tether during termination. An example of such a clamping device is illustrated in FIG. 22. For the embodiments shown in FIG. 22, clamp 910 is closed in its rest state. Before locking, tether 534 is threaded through clamp 910, between propped-open jaws 911 and 912. The jaws can be propped open by propping mechanism 913, e.g., a wire, a tube, or any suitable mechanism. After the tether is in its desired position, the propping mechanism is withdrawn such that jaws 911 and 912 clamp down on tether 534. The clamping device illustrated in FIG. 22 can be used either to clamp directly onto tether 534 or to clamp tether 534 to most proximal anchor.

Figure 23A:
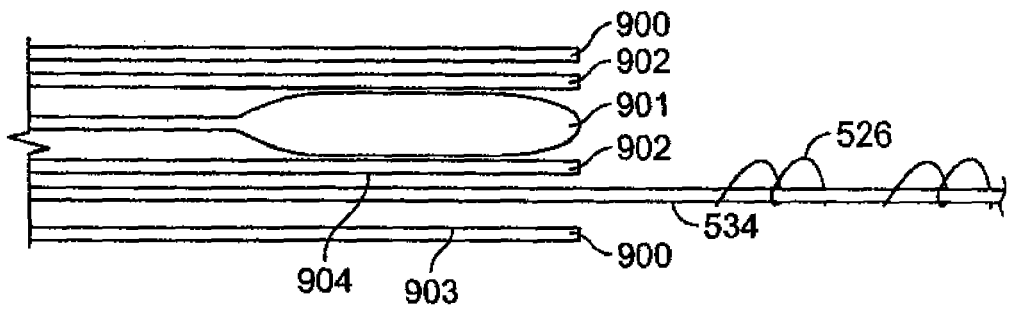
FIGS. 23A-C illustrate variations of termination devices and methods that utilize an expandable mesh element to fix a tether.
Figure 23B:
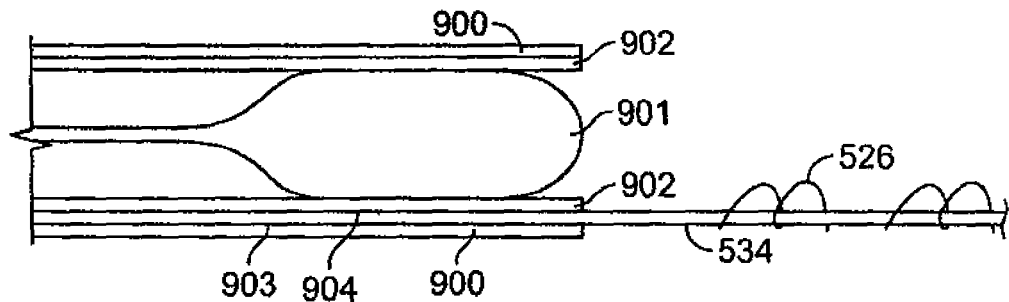
Figure 23C:
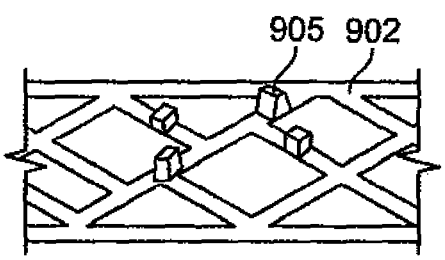

Clamping devices with expandable, deformable mesh may be used to clamp tethers during termination. Examples of such clamping devices are illustrated in FIG. 23A-C. As shown in FIG. 23A, expandable member 901, e.g., a balloon, encased or partially encased in an expandable mesh element 902 is provided within tube 900, e.g., a catheter. Tether 534 is threaded between inner wall 903 of tube 900 and outer wall 904 of expandable mesh element 902. As shown in FIG. 23B, as expandable member 901 is expanded, tether 534 is compressed between mesh outer wall 904 and tube inner wall 903. In some variations, it may be desired to provide a mesh element having a textured surface, roughened surface, or adhesive properties to increase friction with tether 534. For example, as illustrated in FIG. 23C, mesh element 902 having flanges or other protruding features 905 can be provided that is capable of catching and/or compressing tether 534. Mesh element 902 can be made of any suitable material, e.g., metal, polymer, or any suitable type of fiber, and can have a tubular, or any other suitable, configuration. Tube 900 can be made of any suitable material, and can be rigid or flexible. For example, tube 900 can include an elastomer. Inner wall 903 of tube 900 can be coated with an elastomer or adhesive. The walls of tube 900 can be interrupted, e.g., by providing holes with which the metal mesh can interact, e.g., by at least a partially interlocking interaction. In some variations, the mesh is self-expanding. In these variations, expandable member 901 may be omitted. A sleeve (not shown) may be installed around self-expanding mesh to constrain the outer diameter of the mesh. When the sleeve is removed, e.g., by retraction, the mesh is able to expand outwardly to lock tether 534 between the mesh and tube 900. Self-expanding mesh may be made of materials such as shape-memory metals or superelastic metals.

Figure 24A:
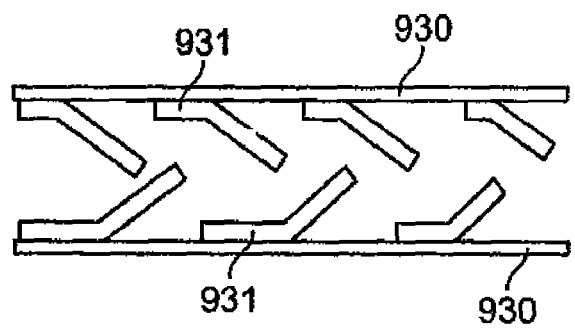
FIGS. 24A-B show examples of termination devices and methods that incorporate threading a tether through protrusions that allow the tether to slide in one direction, but not in the opposite direction.
Figure 24B:
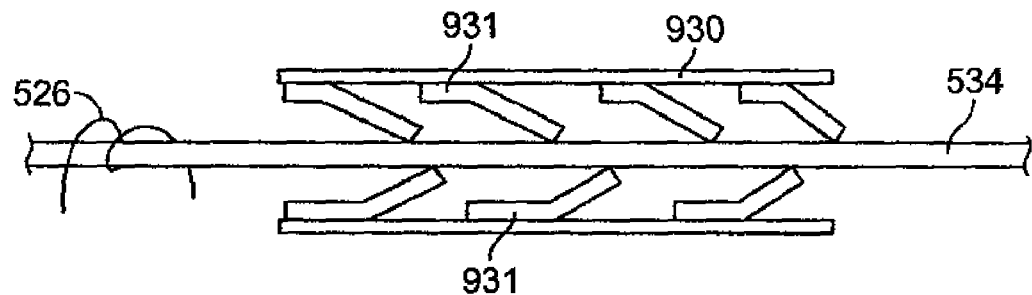
Figure 25:
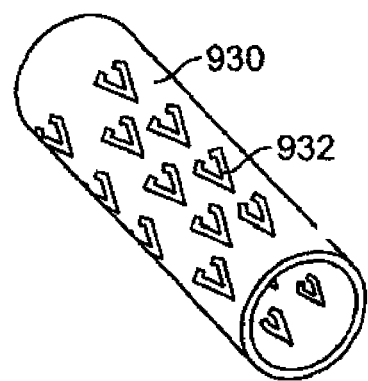
FIG. 25 shows another example of a termination device as described herein.

A hollow locking element having features that protrude towards its interior can be used to fix tether 534 during termination. An example of such a locking element 930 is provided in FIG. 24A. Tether 534 is threaded through hollow locking element 930. Features 931, such as barbs, flaps, or prongs, protrude inwardly. An inner cross-sectional dimension of element 930 is small enough such that at least some of features 931 contact tether 534 as it is threaded through element 930. Features 931 are angled in a proximal direction, such that locking element 930 can be slid in a distal direction until it reaches or is close to most proximal anchor 526. Because features 931 are angled in a proximal direction, and at least some of features 931 contact tether 534, motion in the opposite direction (i.e., sliding element 930 in a proximal direction) will be opposed by features 931 exerting force against tether 534. In some cases, features 931 may be flexible to ease the pulling of tether 534 through element 930 in a distal direction during the cinching of tether 534. In some variations, features 931 can be sharp enough or small enough in dimension so as to become interlocked with inter-thread spaces in tether 534. Locking element 930 can be prepared by any suitable method. For example, as illustrated in FIG. 25, V-shaped grooves 932 can be cut into a metal tube (e.g., by using a laser). The resulting V-shaped metal pieces can be bent inward, forming a cross-section of element 930 similar to that illustrated in FIG. 24A. A plug that fits into a collar can be used to lock the tether during termination.

Figure 26A:
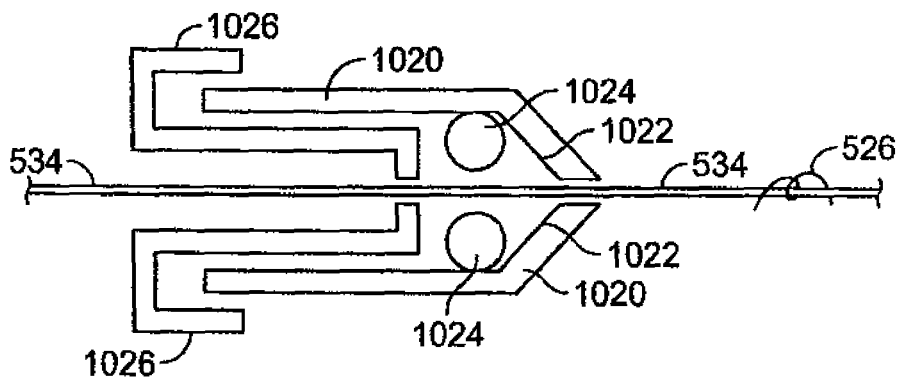
FIGS. 26A-B show examples of termination devices and methods that include threading a tether through a compressible ring, and then compressing the ring such that the inner dimension of the ring is reduced sufficiently to prevent the tether from sliding through the ring.
Figure 26B:
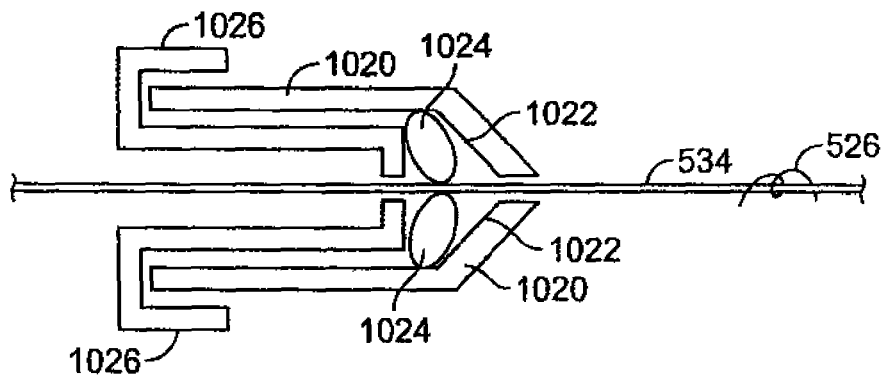
Figure 27:
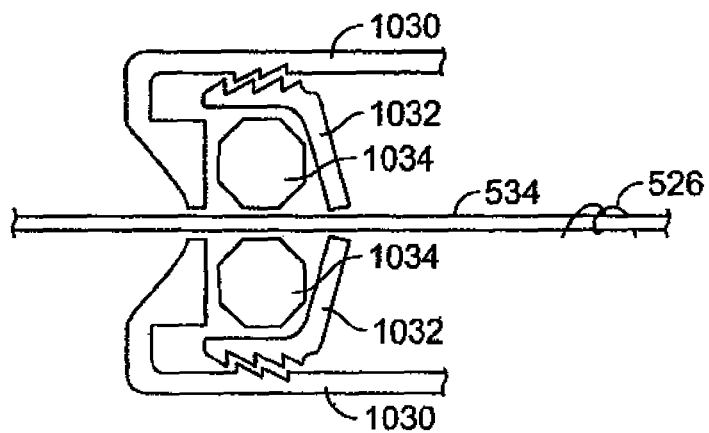
FIG. 27 shows another example of a termination device and method that includes threading a tether through a compressible ring, and then compressing the ring such that the inner dimension of the ring is reduced sufficiently to prevent the tether from sliding through the ring.

Collars comprising deformable materials can also be used to lock the tether during termination. Examples of these variations are illustrated in FIGS. 26A-B and FIG. 27. As shown in FIG. 26A, tether 534 can be threaded through a cylindrical collar 1020 and deformable ring 1024 positioned in the interior of collar 1020 and seated on a base 1022 of collar 1020. Ring 1024 can be any suitable deformable ring, such as an O-ring. Before locking the tether during termination, tether 534 can slide freely through cylindrical collar 1020. When fixing the tether into place, pushing element 1026 is pushed into the interior of collar 1020 such that ring 1024 is compressed, thus reducing its inner diameter (FIG. 26B). Ring 1024 is chosen such that its inner diameter when compressed is small enough to restrict movement of tether 534. Alternatively, 1024 could be a shape other than a ring, such as two or more portions which are compressed so that they grip tether 534 between them. Pushing element 1026 can be pushed into collar 1020 by any suitable technique. For example, the interior of collar 1020 and element 1026 can be threaded, such that element 1026 can be screwed down to compress ring 1024. Alternatively, pushing element 1026 can have a friction fit with collar 1020 to compress ring 1024. In other variations, the pushing element is spring loaded such that it fits into collar 1020 and can compress ring 1024. In still other variations, an additional cap or spring (not shown) can be applied to push element 1026 down to compress ring 1024. As illustrated in FIG. 27, the interior of collar 1030 and the exterior of pushing element 1032 can be configured such that element 1032 is ratcheted along the interior of collar 1030 when force is applied, thus compressing ring 1034 and constricting tether 534 such that it cannot slide. For the embodiments shown in FIGS. 26A-B and FIG. 27, rings 1024, 1034 can have any suitable cross-sectional shape and be made of any suitable material. For example, in some cases, it may be desired that rings 1024, 1034 have round or polyhedral, e.g., octahedral, cross-sectional shapes. Material for rings 1024, 1034 can be chosen for any desired property, such as deformability, biocompatibility, or coefficient of friction with the material used for tether 534. In other variations, the tether can be clamped by altering a path of the tether through a locking feature to increase the frictional forces on the tether. For example, the tether can be threaded through a network of rollers or pins to lock the tether in place during termination.

Figure 28A:
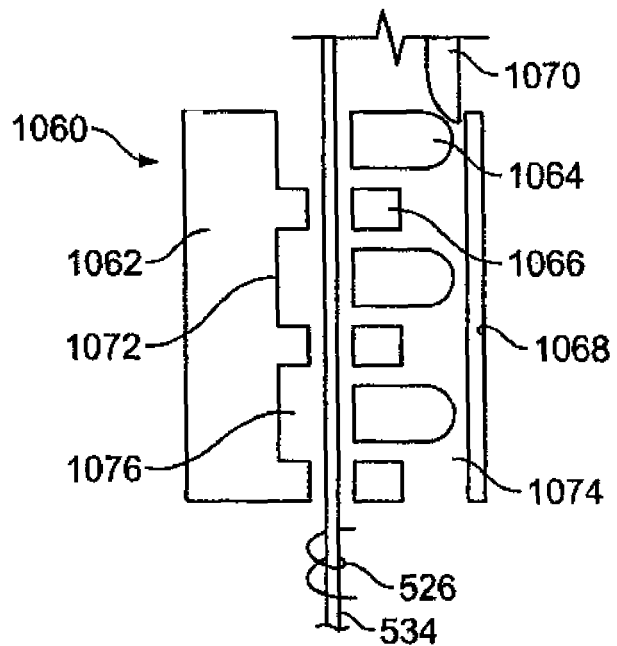
FIGS. 28A-C show examples of termination devices and methods that include threading a tether through a channel of a clamping device, and inserting an actuator that forces actuator elements into the channel to impede slippage of the tether to lock the tether in place.
Figure 28B:
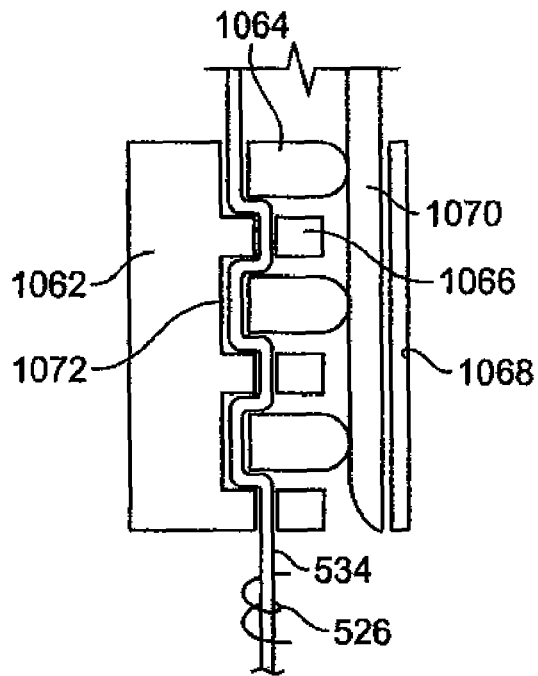
Figure 28C:
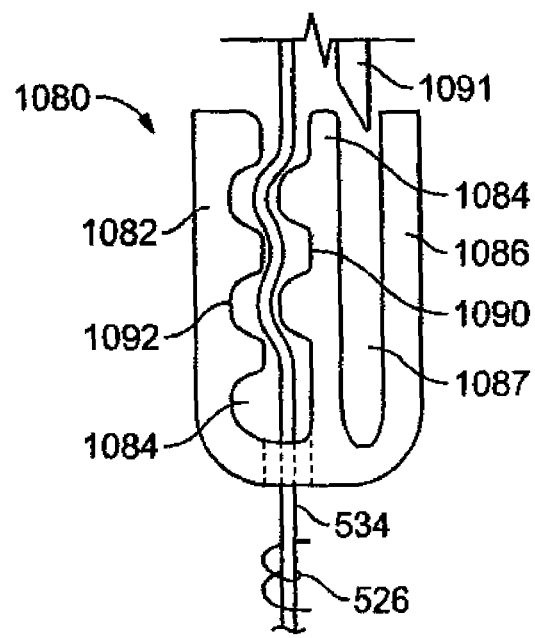

As shown in FIGS. 28A-B, clamps containing actuated clamping elements can be used to lock the tether in place during termination. For example, clamp 1060 containing clamping elements 1064 and 1066 can be used. Clamp 1060 has first side wall 1062 with a profiled inner surface 1072 and opposite side wall 1068. Actuator channel 1074 is provided between side wall 1068 and elements 1064 and 1066. Elements 1064 are arranged generally collinearly with and alternated with elements 1066 along a length of clamp 1060, such that elements 1064 protrude further into actuator channel 1074. Tether 534 is threaded through channel 1076 between elements 1064, 1066 and profiled inner surface 1072 of first side wall 1062. As actuator 1070 is forced into actuator channel 1074, actuating elements 1064 are preferentially pushed into channel 1076, creating a tortuous path for tether 534 that is threaded through channel 1076 (FIG. 28B). In some cases, actuating elements 1064 have rounded edges where actuator 1070 will slide against them to force them into channel 1076. Profiled inner surface 1072 can have any suitable profile to lock tether 534 during termination. In some variations, a locking device made from a single piece can be used to accomplish the same locking principle as exemplified in FIGS. 28A-B. For example, as shown in FIG. 28C, locking device 1080 can be used. Locking device 1080 comprises a first side wall 1082 having first profiled inner surface 1092. Middle wall 1084 having second profiled inner surface 1090 is provided opposite first inner surface 1092. Second side wall 1086 is provided, separated from middle wall 1084 by actuator channel 1087. Tether 534 is threaded through channel 1084 between surfaces 1090 and 1092. Before locking device 1080, tether 534 can move freely through channel 1084. When it is desired to lock tether 534 using device 1080, an actuator 1091 can be inserted into actuator channel 1087, forcing profiled surfaces 1090 and 1092 together, thus creating a tortuous path for tether 534, and preventing it from slipping through device 1080.

Adhesive may be used to facilitate the locking of the tether. For example, drops of adhesive material may be applied, e.g., released from an applicator, to bond the tether to any locking mechanism. For example, adhesive may be applied to knots (see FIGS. 16A-E, for example), clamping devices (see FIGS. 19-23, for example), or to protrusions on the tether (see FIGS. 17 and 18A, for example). Pressure activated or pressure sensitive adhesives may be used. For example, with reference to FIG. 23A-C, the exterior of mesh 902 and or the interior of tube 900 can be at least partially lined with a pressure activated or pressure sensitive adhesive.

After the tether is locked to prevent it from slipping through the most proximal anchor, the excess tether must be cut so it can be removed during termination. Generally, the tether is cut proximal the locking mechanism. In many cases, it is desired to cut the tether as closely as possible to the locking mechanism, while leaving enough excess length to allow for any slippage that may occur. The following examples provide various methods and devices for cutting the excess tether.

Figure 29A:
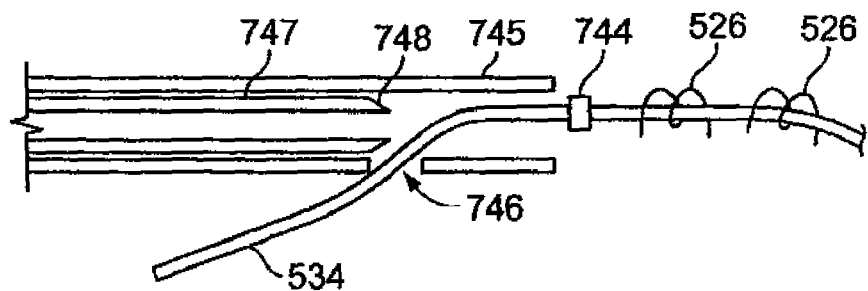
Figure 29B:
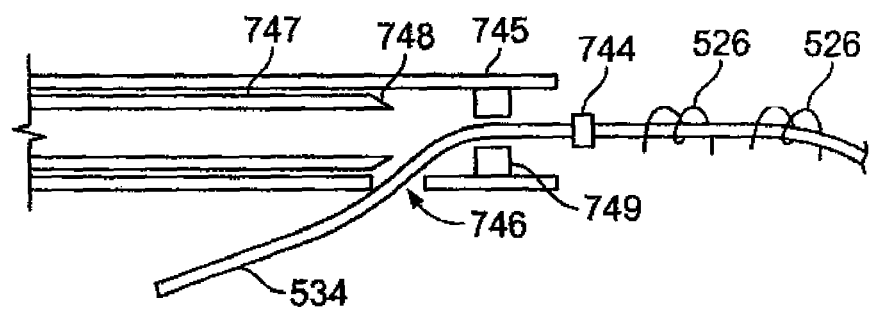
Figure 29F:
Figure 29F:
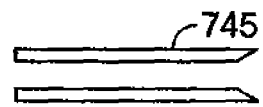
Figure 29F:
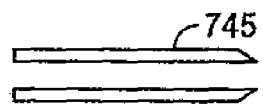
Figure 29F:
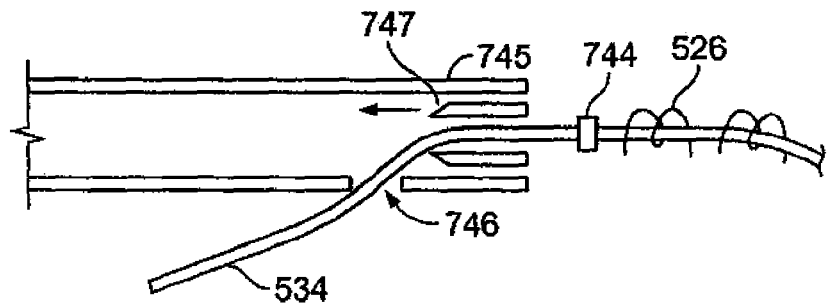

In some variations, concentric tubes can be used to cut excess tether. One concentric tube can be advanced relative to another concentric tube to shear off excess tether at a desired position. Alternatively, one concentric tube can be rotated with respect to another concentric tube to cut the tether. For example, as shown in FIG. 29A, in some embodiments, tether 534 has been cinched and is fixed relative to most proximal anchor by locking feature 744. Although locking feature 744 is shown herein as separate from the most proximal anchor for illustrative purposes, locking feature 744 can also be part of, or integral with, the most proximal anchor. In addition, locking feature 744 can be located external or internal to a catheter or other intravascular device. Tether 534 enters a catheter 745 and exits through a side opening 746. Tether 534 can be loaded into catheter 745 by any suitable method, for example those described herein in FIGS. 14-15. A cutting tube 747 having an edge 748 sharp enough to cut tether 734, e.g., a metal tube having a sharpened edge, is attached to a flexible tube or to a rod and is advanced inside the catheter over side opening 746 from which tether 534 extends. As it is advanced over tether 534, cutting tube 747 can shear off the excess portion of the tether. In some variations, as shown in FIG. 29B, cutting tube 747 is advanced against a base 749 that can assist tube 747 in cutting through tether 534. Base 749 can for example be a block positioned on the interior of catheter 745. Alternatively, base 749 can be part of catheter 745 or be formed integrally with catheter 745. Base 749 can be formed of any suitable material, e.g., any elastomeric or rigid material. In some variations, cutting tube 747 can be spun or rotated to improve cutting. The profile of cutting tube 747 can be any suitable shape, for example V-shaped or triangular, as shown in FIGS. 29C-E. In addition, cutting tube 747 may have a serrated or saw-tooth pattern of sharp protrusions around its perimeter to aid in cutting. Such variations may be used for example when tube 747 is spun or rotated during the cutting process. In some variations, as shown in FIG. 29F, cutting tube 747 can be positioned in front of hole 746 such that cutting tube 747 can be pulled in a proximal direction toward hole 746 to cut tether 534 (indicated by solid arrow).

Figure 30A:
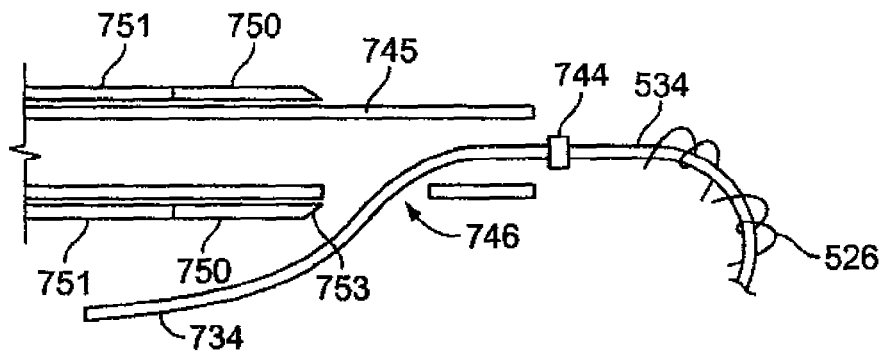
FIGS. 30A-B show additional examples of termination devices and methods that utilize sharpened tubes to sever excess tether.
Figure 30B:
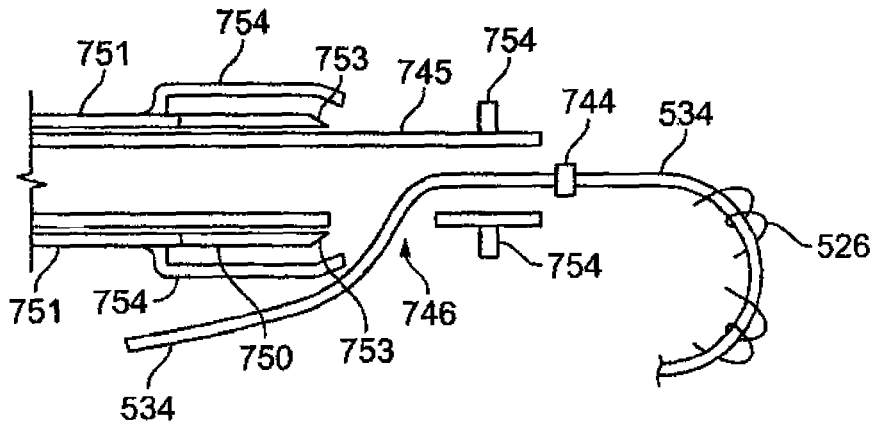

Alternatively, a cutting tube can be provided that is external to a catheter housing tether 534. For example, as shown in FIG. 30A, tether 534 extends through catheter 745 and exits through hole 746. Again, tether 534 can be loaded into catheter 745 by any suitable method, including methods described herein. Cutting tube 750, which can be a sharpened metal tube, can slide along the exterior of catheter 745. In some variations, cutting tube 750 is attached to a second tube 751 which slides along the exterior of catheter 745. Second tube 751 can be flexible. As cutting tube 750 is advanced in a distal direction toward hole 746 (indicated by solid arrow), end 753 of tube 750 can sever tether 534. As shown in FIG. 30B, a base 754 can be positioned along catheter 745 such that tether 534 is pushed against base 752 as cutting tube 750 is advanced toward hole 746, thereby improving the cutting process. As also shown in FIG. 30B, a cover or shroud 754 can be provided around cutting tube 750 in some variations to prevent sharpened end 753 from catching on tissue or the like. In some variations, cover 754 is attached to second tube 751.

Figure 31A:
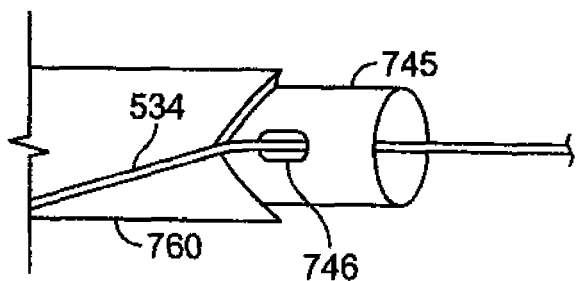
FIGS. 31A-D illustrate variations of tubular termination devices and methods that can be used to cut excess tether after the tether is locked into place.
Figure 31B:
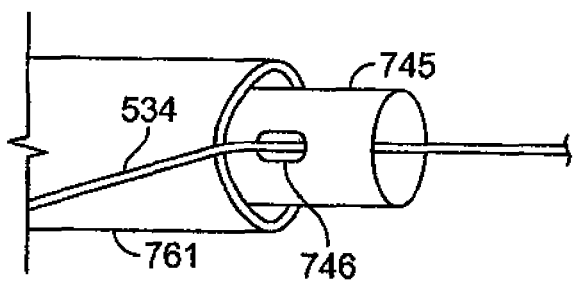
Figure 31C:
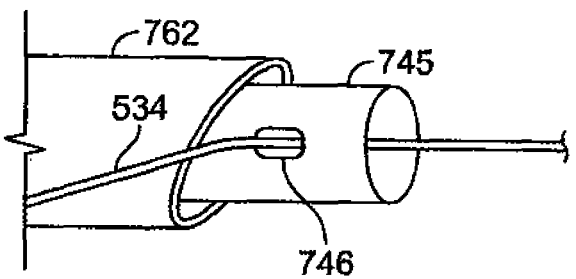
Figure 31D:
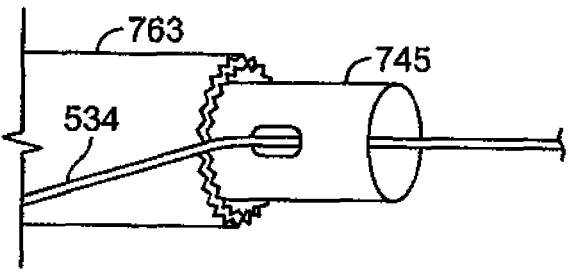

Cutting tubes can have any suitable shape. For example, as shown in FIG. 31A, cutting tube 760 can have a V-shape along its perimeter or other notched feature designed to channel tether 534. Alternatively, cutting tube 760 can have a curved profile (FIG. 31B), an angled profile (FIG. 31C), a serrated profile (FIG. 31D), or a saw tooth profile (not shown). The latter two variations may be useful when cutting tube 760 is rotated or spun during the cutting process. In some variations, the perimeter of hole 746 is sharpened to cut tether 734. The cutting tubes can be configured such that they operate either externally or internally to catheter 745.

Figure 32A:
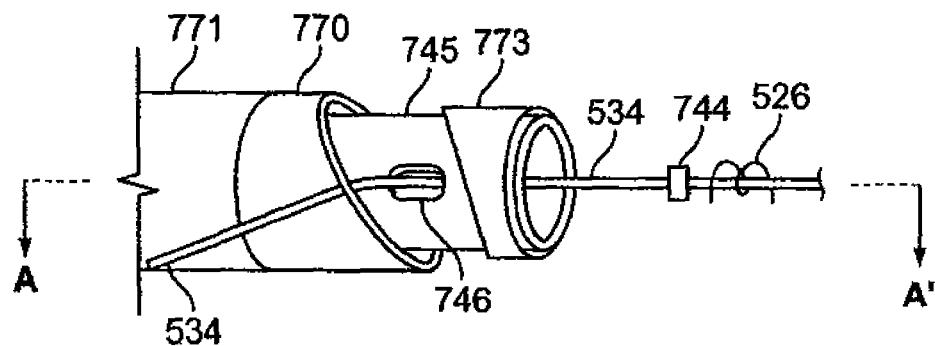
FIGS. 32A-B show other variations of tubular termination devices and methods for cutting tether.
Figure 32B:
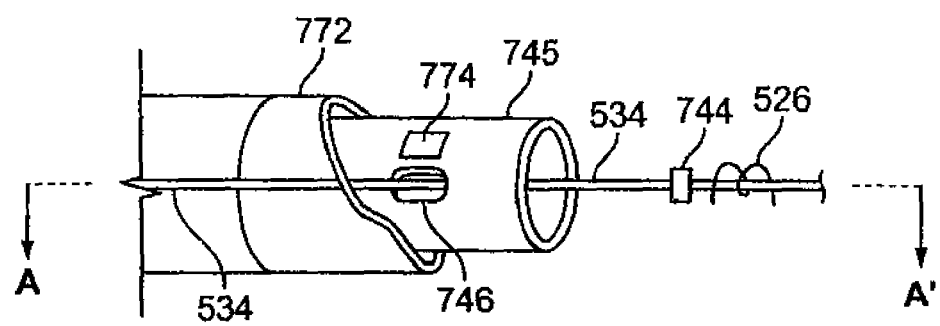

In some variations, cutting tubes can sever the tether by cutting in a direction roughly perpendicular to the long axis of the catheter, e.g., by rotating one concentric tube relative to a second concentric tube. As illustrated in FIG. 32A, tether 534 enters catheter 745 and exits through hole 746. Cutting tube 770 can be configured such that when it is rotated about the long axis A-A' of catheter 745, it can slice tether 534. For example, cutting tube 770 can have an angled shape such that when it rotates about axis A-A' it cuts tether 534. In some variations, cutting tube 770 is attached to a flexible tube 771. In other variations, a blocking structure 773 is disposed on catheter 745. Blocking structure 773 can have any suitable shape, and can serve as a base against which tether 534 can be pushed during the cutting process. Block 773 can be attached to, part of, or integral with catheter 745. Alternatively, as shown in FIG. 32B, the cutting tube 772 can have a profiled shape to enable it to cut tether 534 in a direction generally orthogonal to long axis A-A' of catheter 745 as it is rotated around axis A-A'. Optionally a blocking structure 774 can be provided on catheter 745 such that tether 534 is pushed against block 774 during the cutting process. Block 774 can be any suitable shape or have and suitable configuration and can be attached to, part of, or integral with catheter 745. Cutting tubes such as those illustrated in FIGS. 32A-B can be configured such that they are internal to the catheter.

Figure 33:
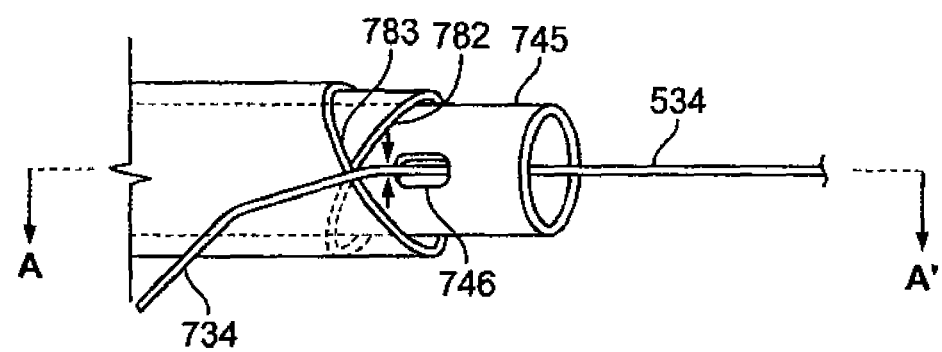
FIG. 33 illustrates variations of termination devices and methods that utilize concentric tubes for cutting tether.

In some variations, a pair of concentric cutting tubes can be used to cut the tether. The concentric tubes can be either internal or external to the catheter. As illustrated in FIG. 33, the two concentric cutting tubes 780 and 781 can be rotated about the long axis A-A' of catheter 745 in opposite directions (indicated by solid arrows). Thus, the cutting edges 782 and 783 can cut tether 534 in a scissor-like fashion. Cutting edges 782 and 783 can be sharpened in such a way to enable edges 782 and 783 to pass each other as closely as possible.

Figure 34A:
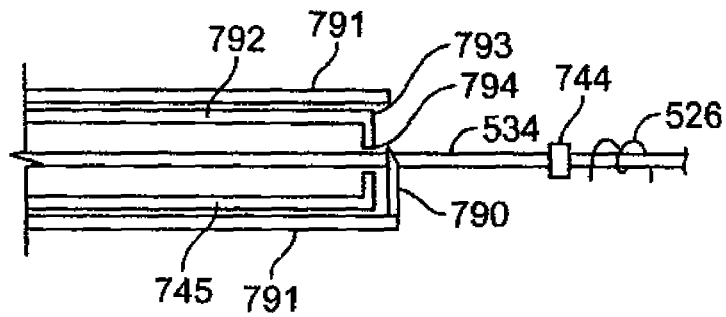
FIGS. 34A-D show variations of termination devices and methods that include a rotatable blade attached to the end of a tube.
Figure 34B:
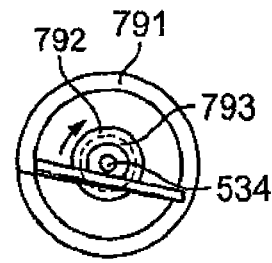

In some variations, the tether does not exit the catheter through a side hole. In these variations, a cutter can be mounted on a tube concentric to the catheter, either externally or internally, and rotated to cut the cable. For example, as shown in FIG. 34A, excess tether 534 proximal locking feature 744 enters catheter 792 through its end opening 794. Optionally catheter 792 can have lips 793 that restrict the diameter of the end opening 794. A concentric tube 791 has attached thereto a blade 790, which can be rotated to sever excess tether 534. FIG. 34B illustrates the operation of blade 790 on tether 534 as it is rotated.

Figure 34C:
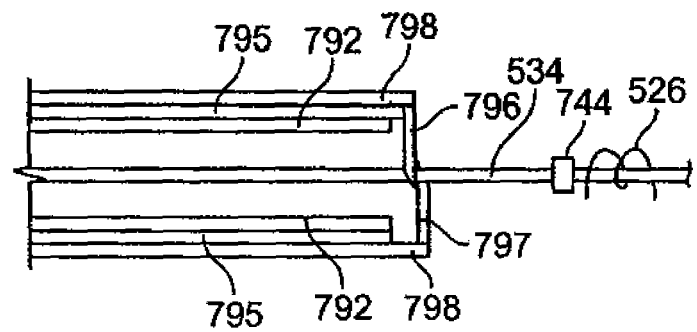
Figure 34D:
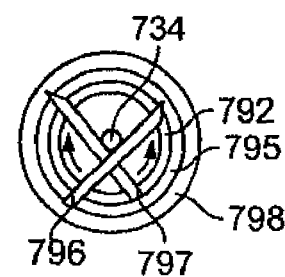

Alternatively, as shown in FIG. 34C, two concentric tubes 795 and 798 can be provided. Tube 795 has blade 796 attached to its end; tube 798 has blade 797 attached to its end. Blades 796 and 797 are oriented generally perpendicular to the long axes of tubes 795 and 798. The tubes 795 and 798 are rotated in opposite directions about their respective long axes to cut tether 534. FIG. 34D illustrates the operations of blades 796 and 797 on tether 534 as they are rotated. Blades 796, 797 can be configured such that sharpened edges pass each other closely enough and at such angles to facilitate cutting. The cutting blades 790, 796, and 797 can have any suitable shape, e.g., angled, V-shaped, or curved. The concentric tubes 795, 798 can be mounted either external or internal to catheter 792. For example, one tube can be external while the other is internal.

Figure 35A:
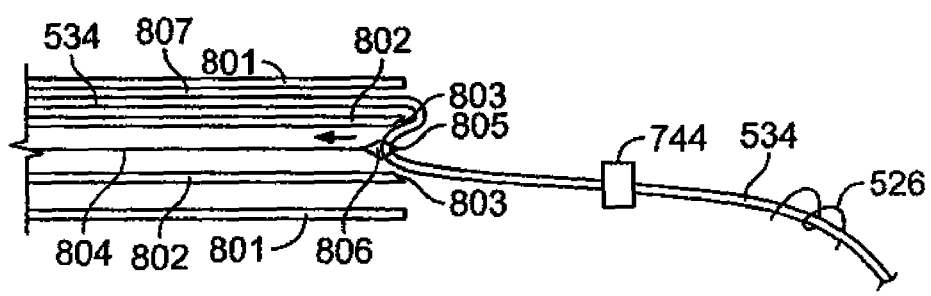
FIGS. 35A-C provides examples of termination devices and methods that include a hook that pulls excess tether over a cutting surface to sever the tether.

In some variations, as illustrated in FIG. 35A, a hook, loop or the like can be used to engage the tether between the most proximal anchor and the distal end of the catheter. Tether 534 is cinched, locked into place by locking feature 744, and threaded lengthwise through catheter 801 in channel 807 between an inner wall of catheter 801 and cutting tube 802. Cutting tube 802 has a sharpened edge 803 on its distal end. Assembly 804 having hook 805 on its distal end is configured such that it extends through cutting tube 802. Hook 805 engages a portion 806 of the excess tether that extends proximally from locking feature 744. The length of tether 534 threaded through channel 807 is pulled in a proximal direction. Hook 805 can pull portion 806 of tether 534 in a proximal direction (indicated by solid arrow), forcing the tether against sharpened edge 803, which severs the excess tether. Alternatively, hook 805 can include a sharpened edge or blade such that it can cut tether 534.

As described above, the tether cutter may comprise any appropriate structure or material. For example, in addition to the cutting tubes described above, the tether cutter may cut by heat, electricity, chemical reaction, or the like. For example, the tether cutter may comprise an electrode or filament through which electrical energy may be applied to cut the tether.

Figure 35B:
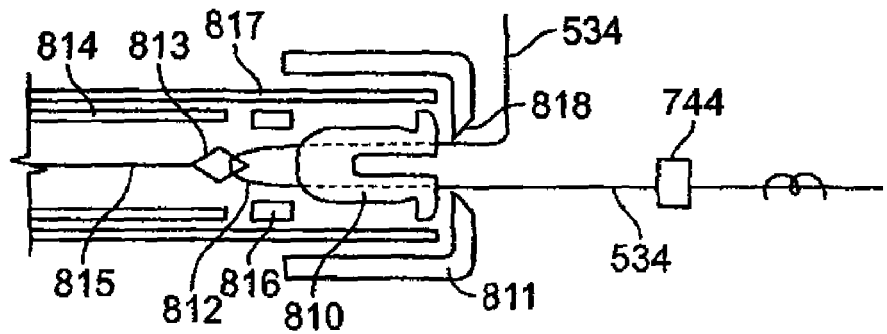

In other variations, as illustrated in FIG. 35B, tether 534 can be threaded through a collet 810 comprising a housing 811. Housing 811 can be coupled to catheter 817. Tether 534 is threaded through collet 810 such that a loop 812 of tether 534 extends in a proximal direction from collet 810. Collet 810 can have any suitable shape, e.g., U-shaped or C-shaped. A hook or loop 813 coupled to apparatus 815 can be used to engage loop 812. A pusher 814 can be used to apply force in a distal direction to collet 810 while hook 813 is pulled in a proximal direction by apparatus 815. As hook 813 is pulled in a proximal direction, tether 534 is forced against cutting blade 818. Cutting blade 818 can have any suitable orientation or configuration such that tether 534 can be forced against a cutting surface of cutting blade 818. Cutting blade 818 can be attached to, part of, or integral with housing 811. Optionally, a collar 816 can be placed between collet 810 and pusher 814 to aid in applying force to collet 810. In some variations, collet 810 can be placed internal to catheter 817, and housing 811 can be omitted. In those variations, catheter 817 can comprise a cutting blade (not shown) attached to, part of, or integral with the catheter and configured such that as loop 812 of tether 534 is pulled in a proximal direction, tether 534 is forced against the cutting blade. In some variations, hook 813 can be capable of cutting tether 534 as tension is applied. In those variations, cutting blade 818 may be omitted. In FIG. 35B is that hook or loop 813 draws the end of the tether is drawn into collet 810. Then, tube 814 pushes down 816 around 810 to lock in the tether 534. The assembly of tether, collet and collar 534, 810, 816 is released all together, becoming an element which locks the tether and prevents slipping through the most proximal eyelet.

Figure 35C:
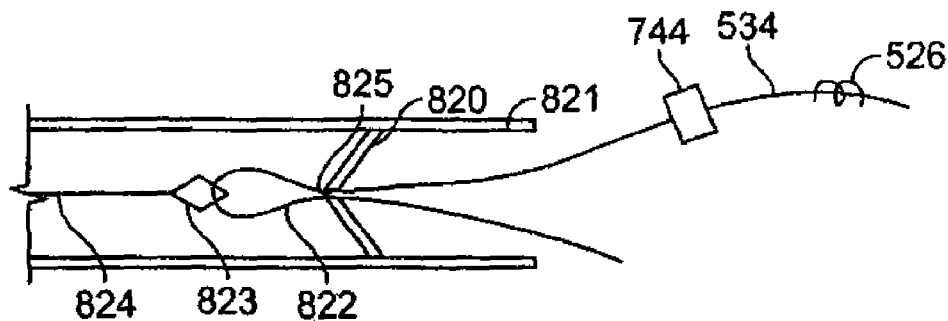

In other variations as shown in FIG. 35C, tether 534 can be threaded through a one-way locking mechanism 820 provided internal to catheter 821. Locking mechanism 820 can be separate from, e.g., part of a separate tube, or attached to catheter 821. Locking mechanism 820 comprises opposing angled flaps 824. The flaps are angled in a proximal direction and closely spaced such that the tether can be pulled through mechanism 820 in a proximal direction forming a loop 822 extending in a proximal direction from mechanism 820. A hook 823 coupled to apparatus 824 engages tether loop 822. Once the tether is cinched to the desired tension by pulling loop 822 proximally and locked into place by locking device 744, tether 534 can be pulled in a distal direction and cut by cutting edges 825 provided as part of flaps 824. Optionally, cutting edges 825 can be serrated or comprise teeth to aid in cutting. FIG. 35C illustrates a locking device that is an alternative to the device shown in FIG. 35B. Here, instead, the loop 822 is pulled through and locked. Then, the whole thing (locking flaps and loop) is released to be the "lock" that prevents slipping the tether from slipping through the eyelet.

Figure 36A:
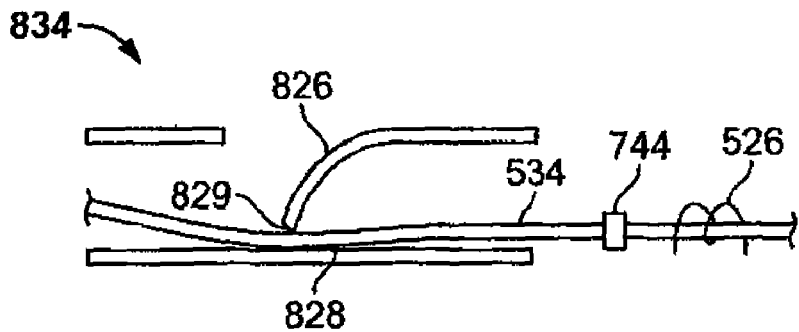
FIGS. 36A-B show examples of termination devices and methods that include the use of angled barbs to cut excess tether.

As shown in FIG. 36A, cutting apparatus 834 comprising single angled flap 826 can be used to cut excess tether. Cutting apparatus 834 can be internal to a catheter (not shown) or part of a catheter. Cutting apparatus 834 comprises wall 828, opposite flap 826. In some variations, wall 828 is a wall of a tube. In other variations, both surface 828 and flap 826 are formed from the same tube. Flap 826 is angled in a proximal direction and abuts or is in close proximity to wall 828. Tether 534 can be threaded between flap 826 and wall 828 by pulling in a proximal direction. However, when force is applied to pull tether 534 in a distal direction, cutting edge 829 of flap 826 digs into and severs tether 534.

Figure 36B:
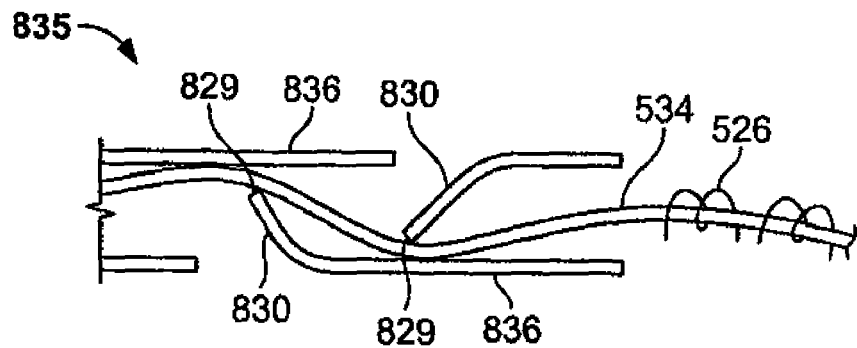

As shown in FIG. 36B, in some variations a cutting apparatus 835 comprising multiple angled flaps can be provided. Several spaced apart or staggered flaps 830 having cutting edges 833 are provided opposite walls 836. Flaps 830 are angled in a proximal direction and abut or are in close proximity to opposing walls 836. Tether 534 can be threaded in a proximal direction between walls 836 and flaps 830. When tether 534 is pulled in a distal direction, cutting edges 833 dig in and operate to sever tether 534. For the variations shown in FIGS. 35D-E, cutting edges 829, 833 can be configured in any suitable manner, e.g., they may be sharpened blades, comprise a serrated cutting edge, or comprise teeth.

Figure 37:
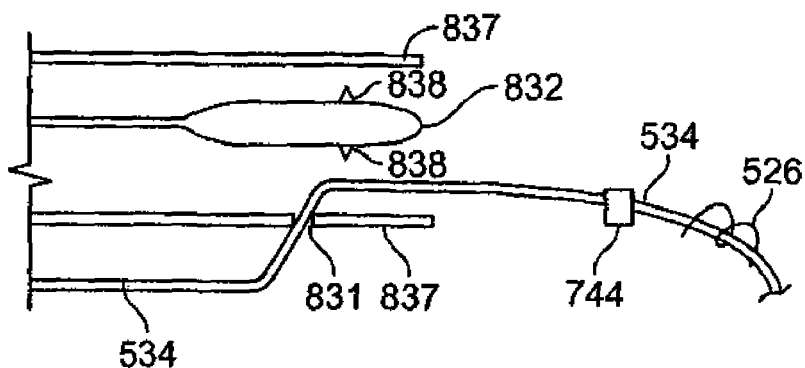
FIG. 37 illustrates variations of termination devices and methods in which a cutter attached to an expandable member is used to cut a tether.

As shown in FIG. 37, a cutter can be mounted on a balloon within a catheter. An excess portion of tether 534 proximal to locking device 755 enters catheter 837 at its distal end and exits through side hole 831. Expandable member 832 is provided within catheter 837 and is adjacent to the section of tether 534 within catheter 837. Expandable member 832 can be, for example, a balloon, or more than one balloon. Attached to the perimeter of the expandable member are cutters (e.g., blades) 838 capable of cutting tether 534. Expandable member 832 can be expanded such that tether 534 is pressed between an interior wall of catheter 837 and cutter 838. When in its expanded state, expandable member 832 can be rotated along an axis generally parallel to the long axis of catheter 837 to cut tether 534. For example, if expandable member 832 comprises a balloon, the balloon can be inflated to an amount such that cutter 838 is pressed against tether 534 but the balloon can still be rotated within catheter 837. Cutter 838 can have any suitable shape or configuration. In some variations, a single blade 838 can be attached to expandable member 832 that is capable of cutting tether 534. In other variations, cutter 838 can sever tether 534 by virtue of the blade being pressed into the tether by the expandable member, and thus need not be rotated to a substantial degree to sever tether 534. In some variations, a deformable mesh tube (not shown) can be provided to at least partially encase expandable member 832. Thus, as expandable member 832 is expanded, it can cause the mesh tube to expand against tether 534, sandwiching it between the mesh and tube 837 to hold tether 534 in place.

Figure 38A:
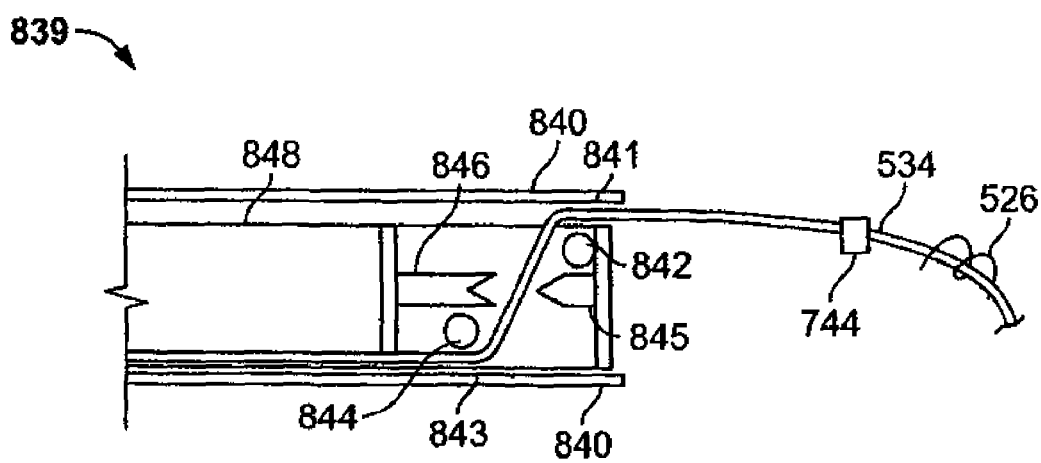
FIGS. 38A-D show examples of various termination devices and methods that involve threading a tether between pins and severing the section of tether extended between the pins.
Figure 38B:
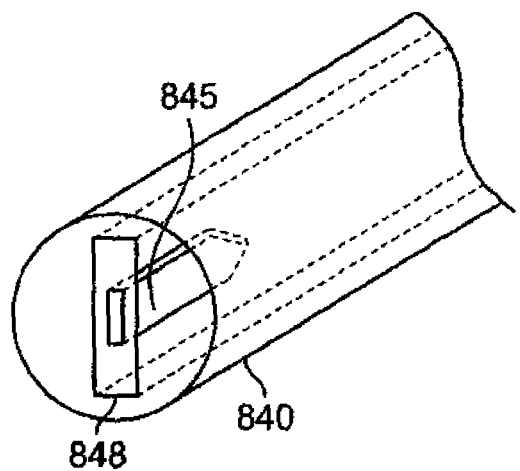
Figure 38C:
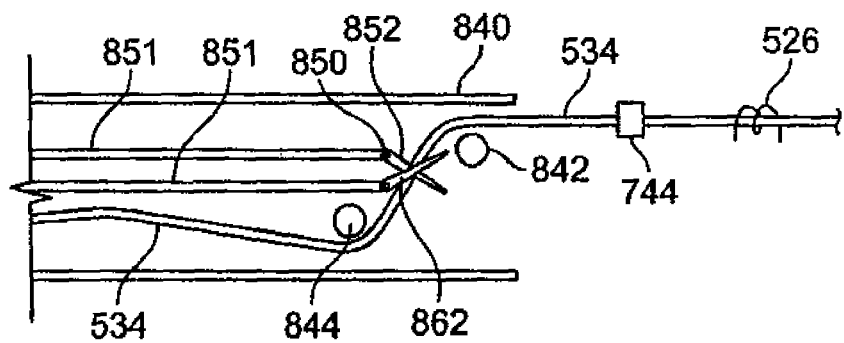
Figure 38D:
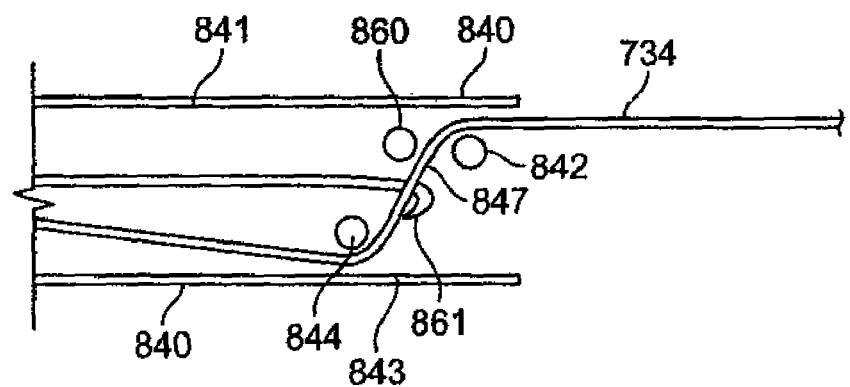

As shown in FIGS. 38A-D, tether 534 can be threaded through cutting apparatus 839 comprising a guillotine-like blade and an opposing cutting block. The excess portion of tether 534 proximal locking device or mechanism 744 is threaded into catheter 840 between side wall 841 and pin 842. Tether 534 then traverses part of the inner diameter of catheter 840 and is threaded between opposite side wall 843 and pin 844. Blade 845 is provided on one side of portion 847 of tether 534 extended between pins 842 and 844. Blade 845 is mounted in any suitable manner, e.g., on a bridge 848 at least partially within catheter 840. Optionally, a cutting block 846 is provided across tether portion 847 and opposite blade 845. As tension is applied to tether 534 in a proximal direction (indicated by solid arrow), blade 845 can be forced against tether portion 847, thus severing the tether. Blade 845 can cut against cutting block 846, when present. As shown in FIG. 38C, a tool comprising a pair of blades connected with a pivot (e.g., a scissor-like tool) 850 can be provided to cut the tether. Tool 850 can operate within or external to catheter 840. Rods 851 connected to opposing blades 852 of tool 850 can be pulled or pushed to sever tether 534. As shown in FIG. 38D, tether 534 can be threaded between catheter side wall 841 and pin 842, between pin 842 and pin 860, and between pin 844 and opposite side wall 843. A sharpened blade or hook 861 can be pulled across tether portion 847 which extends between pins 842 and 844 to cut tether 534.

In some embodiments, cinching tether 534, fixedly coupling tether 534 to most-proximal anchor 526, and cutting excess tether 534 are achieved using a single or integrated termination device (not shown). The termination device may comprise, for example, a catheter that can be advanced over tether 534 that includes a cutting member and a knot, other attachment member, or a locking device for attaching or fixedly coupling tether 534 to most-proximal anchor 526. The termination catheter may be a steerable catheter. The termination catheter may be advanced over tether 534 to a location at or near the proximal end of the tethered anchors 526. The catheter may then be used to apply opposing force to the most-proximal anchor 526 while tether 534 is cinched. The attachment member may be used to attach tether 534 to most-proximal anchor 526 and the cutting member may be used to cut tether 534 just proximal to most-proximal anchor 526. Such a termination device is only one possible way of accomplishing the cinching, attachment and cutting steps, and any other suitable device(s) or technique(s) may be used.

A termination device can incorporate the termination functions of cinching the anchors with a tether, locking the cinching tether, and cutting away the excess length of the cinching tether in many ways. In some embodiments, a deployment device can deploy the anchors into the tissue to be tightened, and also cinch and lock the tether. A separate device can them be employed to cut the tether. Alternatively, the anchor deployment device can deploy the anchors into the tissue, cinch, lock and cut the tether. In other variations, three separate devices can be used in termination: an anchor deployment device; a second device to cinch the tether and lock the tether; and a third device to cut the tether. Termination functionalities can be integrated in any suitable manner in one or more termination devices. In addition, any number or combination of devices can be used in the termination procedure. Provided below are several possible architectures for termination devices that combine or integrate termination functions. These devices are only exemplary devices.

For example, with reference to FIGS. 23A-C, a balloon or other expandable member 901 can be inflated to expand a metal mesh 902 to clamp tether 534 between mesh 902 and an outer tube 900. Subsequently, a sharpened tube can be advanced to cut the tether. For example, if the tether is threaded through a side hole, the sharpened tubes that are provided in FIGS. 30A-B, 31A-D, and 32A-B can be used to cut the tether as indicated in the figures. If the tether is not threaded through a side hole, cutters such as are illustrated in FIGS. 34A-D can be used. Any suitable cutting technique can be also be used to sever the excess tether.

In another example, with reference to FIG. 37 and FIGS. 23A-C, the expandable member or balloon 832 of FIG. 37 can be inflated to expand a metal mesh (not shown in FIG. 37 but similar to mesh 902 as illustrated in FIGS. 23A-C) to compress the tether 534 between the mesh and outer tube 837. Cutting mechanism 838 is mounted to expandable member 832. Expandable member 832 can be configured such that the portion of the expandable member to which cutter 838 is mounted inflates after the metal mesh is expanded. For example, expandable member 838 can comprise two separate balloons, one of which has cutting mechanism 838 attached thereto. When the portion of member 832 comprising cutter 838 is expanded, cutter 838 cuts tether 534. Alternatively, a cutter or cutters 838 can be rotated to sever tether 534. Once the tether has been cut, the mesh locking mechanism applied to the tether can be released, e.g., by advancing a pusher (not shown).

In another example of an architecture of a termination device, with reference to FIG. 37 and FIGS. 16A-E, a multi-stranded half-knot in tether 534 can be pushed down to lock tether 534 in place. Then expandable member can be inflated and rotated at least partially within catheter 837 such that cutters (e.g., blades) 838 cut tether 534. Alternatively, with reference to FIGS. 30A-B, 31A-D, 32A-B, 33, and 34A-D as examples, any type of tube-mounted cutter can be used to sever tether 534. For cutting devices such as those illustrated in FIGS. 30A-B, 31A-D, 32A-B, and 33, in which tether 534 is threaded through a side hole (e.g., side hole 746 in FIGS. 30A-B) to enable cutting, additional tethers or cables used to form multi-stranded knot 721 can also be threaded through the side hole and cut. Any other type of cutting mechanism described herein can be used in combination with a tether locking mechanism employing a multi-stranded half-knot to fix tether 534.

Figure 13A:
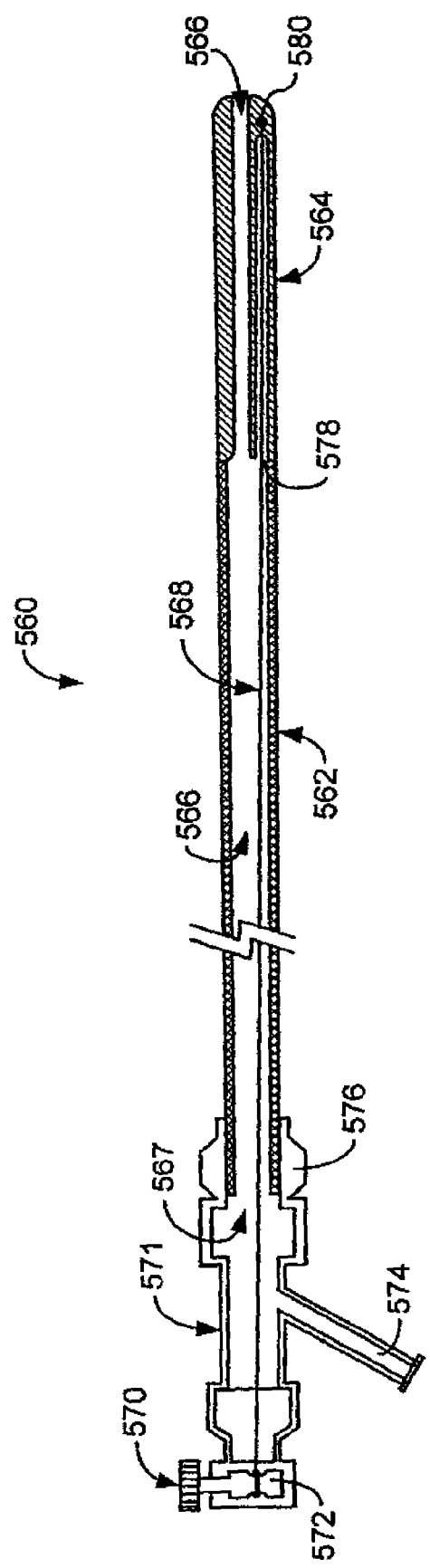
FIGS. 13A and 13B are side cross-sectional views of a guide catheter device for facilitating positioning of an anchor delivery device according to some embodiments.
Figure 13B:
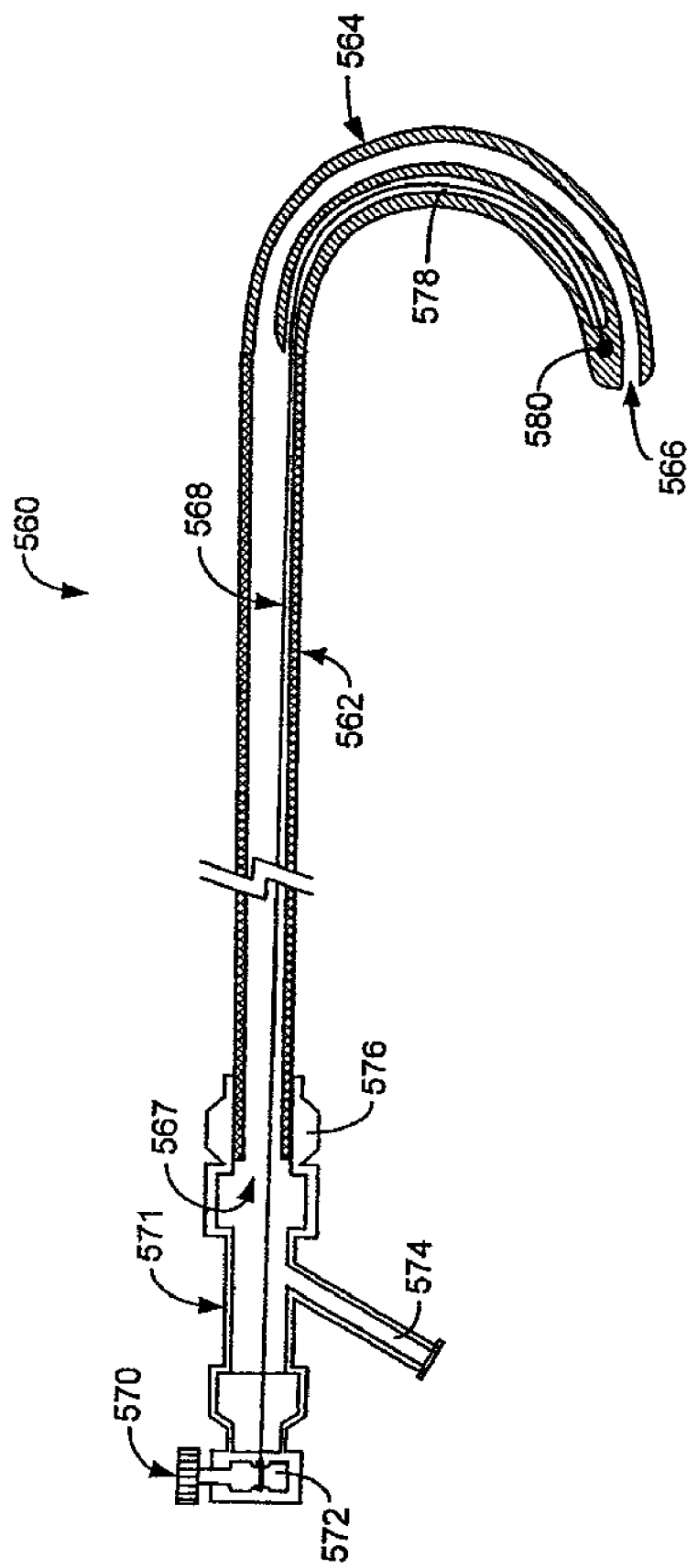

With reference now to FIGS. 13A and 13B, one embodiment of a steerable catheter device 560 is shown. Steerable catheter device 560 may be used in a method such as that just described in reference to FIGS. 12A-12F, for example in performing a function similar to that performed by second guide catheter 554. In other embodiments, catheter device 560 may perform any other suitable function, e.g., any of the termination functions described herein. As shown, catheter device 560 suitably includes an elongate catheter body having a proximal portion 562 and a distal portion 564. At least one tensioning member 568, such as but not limited to a tensioning cord, extends from proximal portion 562 to distal portion 564 and is coupled with the distal portion 564 and at least one tensioning actuator 570/572 on the proximal portion. Tensioning actuator 570/572 may include, for example, a knob 570 and a barrel 572 for wrapping and unwrapping tensioning member 568 to apply and remove tension. Tensioning member 568 is coupled with distal portion 564 at one or more connection points 580. In some embodiments, catheter device 560 includes a proximal housing 571, handle or the like, coupled to the proximal end of proximal portion 562 via a hub 576 or other mechanism. Housing 571 may be coupled with tensioning actuator 570/572 and may include one or more arms 574 for infusing fluid or for other functions. In the embodiment shown, arm 574 and housing 571 include a lumen 567 that is in fluid communication with a fluid lumen 566 of the catheter body. Fluid may be introduced through arm 574 to pass through fluid lumen 566 to provide, for example, for contrast material at the distal tip of catheter device 560 to enhance visualization of device 560 during a procedure. Any other suitable fluid(s) may be passed through lumens 567/566 for any other purpose. Another lumen 578 may be included in distal portion 564, through which tensioning member 568 passes before attaching at a distal location along distal portion 564.

FIG. 13B shows catheter device 560 in a deformed/bent configuration, after tension has been applied to distal portion 564 by applying tension to tensioning member 568, via knob 570 and barrel 572. The bend in distal portion 564 will allow it to conform more readily to a valve annulus, while catheter device 560 in its straight configuration will be more amenable to passage through vasculature of the patient. Tensioning member 568 may be manufactured from any suitable material or combination of materials, such as but not limited to nickel titanium alloys, polyester, nylon, polypropylene and/or other polymers. Some embodiments may include two or more tensioning members 568 and/or two or more tensioning actuators 570/572 to provide for changes in shape of distal portion 564 in multiple directions. In alternative embodiments, knob 570 and barrel 572 may be substituted with any suitable devices, such as a pull cord, button, lever or other actuator. Various alternatives may also be substituted for tensioning member 568 in various embodiments. For example, shaped expandable members, shape memory members and/or the like may be used to change the shape of distal portion 564.

Generally, proximal portion 562 of the catheter body is less flexible than distal portion 564. Proximal portion 562 may be made of any suitable material, such as PEBAX® elastomers, fluoroethylene propylene, nylon, polyethylene and/or the like, and may include a braided material, such as stainless steel, to provide stiffness and strength. Distal portion 564 may be made of similar or other materials, but the braided material is typically not included, to provide for greater flexibility. Both proximal and distal portions 562/564 may have any suitable lengths, diameters, overall configurations and the like. In one embodiment the catheter body is approximately 140 cm in length and 6 French in diameter, but any other suitable sizes may be used in other embodiments. Proximal portion 562, distal portion 564 or preferably both, may be made from or coated with one or more friction resistant or lubricating material to enhance passage of device 560 through an introducer catheter and/or to enhance passage of a sheath or other device over catheter device 560.

As described above, the termination devices described herein may be integrated termination devices, including tether cutters, locking features, tensioning devices, positioning devices, and the like. Provided below are exemplary termination devices including many of these features.

EXAMPLES

Figure 39:
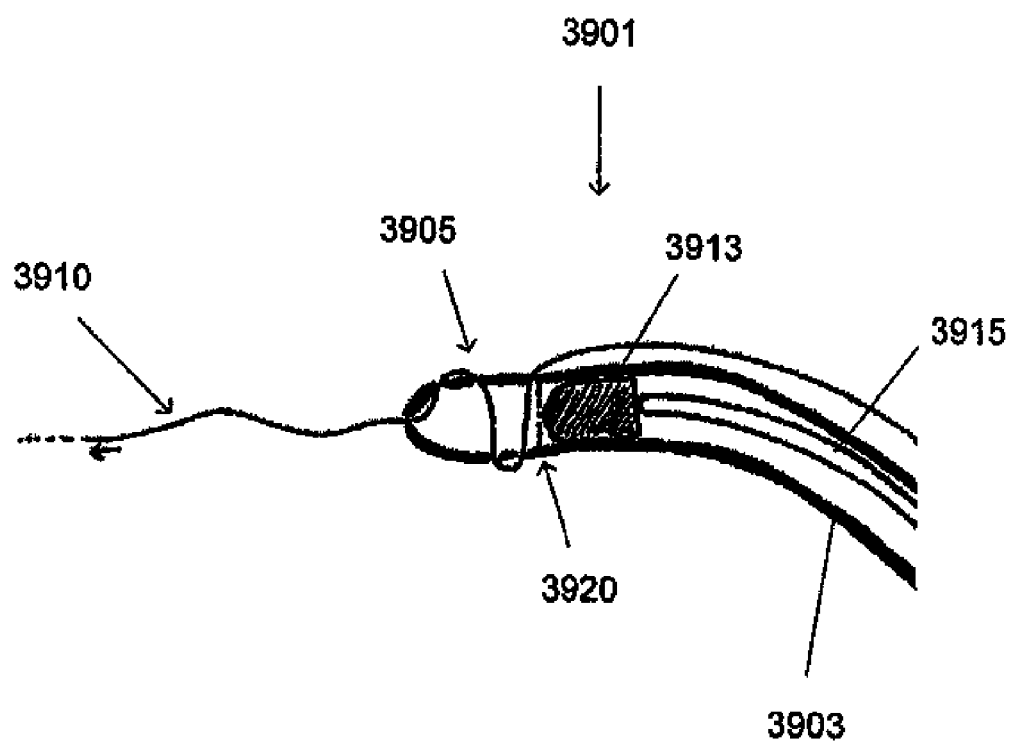
FIG. 39 shows one variation of a termination device as described herein.

In general, termination devices are designed to cinch, lock, and/or cut a tether (e.g., a suture or cable) as described herein. These devices can be used for any surgery where these functions (or combinations of them) are desired. FIG. 39 shows a termination device 3901 having a detachable locking feature 3905 that is releasably attached at the distal end of the termination device. This variation of a termination device has an elongated tubular body 3903 which may be flexible over all (or a portion) of its length. Thus, the termination device may be used in non-invasive procedures (e.g., percutaneously) or in invasive (e.g., open-heart) surgeries. The termination device shown in FIG. 39 is configured as a termination device catheter.

The termination device 3901 shown in cross-section in FIG. 39 is coupled to a tether 3910. The tether is threaded through the distal region of the termination device, particularly through the locking feature 3905 region at the distal end of the termination device. Although any locking feature may be included as part of the termination device, as described above, the locking feature shown in FIG. 39 is a clamping type locking feature in which a plug 3913 fits into a hollow region of the locking feature and secures the tether between the plug and a wall of the locking feature. The tether passes through one or more openings (e.g. passages or holes) on the side of the device. Until the locking feature is secured, the termination device may be moved along the tether (e.g., by sliding), or the tether may be pulled through the termination device. Thus, the tether may be cinched by sliding the termination device down (distally) the tether.

The openings through the termination device may be positioned such that the device can still easily slide along the tether (cinching cable). The tether may be threaded into the locking feature in such a way that it winds in and out of the tube, as suggested by the drawings. This may help the cable slide more easily, because under tension, the cable is free to wind less tightly around the features on the tube (e.g. closer to straight path). The cable may be threaded or coupled to the termination device during manufacturing or by the user. As shown in FIGS. 14A and 14B, a wire loop (or lasso) may be threaded through the openings. Then, after inserting the tether through the loop, the opposite end of the loop can be pulled to thread the tether through the openings. In some variations, the termination device may be slid along the tether until the tether is cinched to the desired size through the anchors, and then secured into position using the locking feature. For example, in FIG. 39, the locking feature is secured by moving the plug 3913 into position within the hollow portion of the locking feature 3905, where it secures (holds) at least a portion of the tether 3910. In the variation shown in FIG. 39, the plug 3913 secures the tether 3910 by compressing at least a portion of the tether between the plug and the inner walls of the locking feature and forcing the tether to wind through the tube through sharp turns. The locking feature (including the plug) may comprise features that prevent the release of the plug from the locking feature. For example, the locking feature may include adhesive or cement, or it may be at least partly deformable so that once the plug is inserted into the distal tip (e.g., locking feature) region of the termination device, it is retained at the distal tip.

The termination device shown in FIG. 39 also includes a plunger or push rod 3915 for pushing the plug 3913 into position to secure the tether within the locking feature of the termination device. The plunger shown may be slidable within the lumen of the termination device. In some variations, the rod may include guides (e.g., guiding the direction) or stops (e.g., limiting the distance that the rod may travel, or the force that may be applied by the rod). Thus, there may be motion-limiting features on the termination device and/or rod to prevent the rod from being pushed too far forward, or applying too much force, which could disturb either the locking mechanism or the tissue (e.g., after separation of the locking mechanism from the rest of the termination device).

The locking feature may be detachably connected to the rest of the termination device. For example, the locking feature may be frangible connected to the termination device, so that it can be detached from the termination device by breaking the connection between the locking feature and more proximal portion of the body of the termination device. Thus, the locking feature e.g., tube, clamp, knot, etc.) can be attached to the rest of the termination device so that it can be separated. The locking feature may be detachably connected to the rest of the termination device by any appropriate method. Thus, the locking feature (or a portion of the locking feature) may include a releasably attachment region. The releasable attachment region may include any region that can be separated or broken to release the locking feature from the elongate body of the termination device. For example, the releasable attachment region may comprise a region where the locking feature is fused to another region of the termination device (e.g., the distal region of the elongate body).

In some variations the locking feature is fused by melting the materials comprising at least a portion of the locking feature and a portion of the rest of the termination device. The two materials may be fused together to different degrees (e.g., by varying the number of fuse spots or area of fusing) to adjust the force necessary to separate the two regions of the termination device. The different regions of the termination device may comprise different materials, or may comprise the same material. In some variations, the fused region comprises a third material used to secure the two regions together until they are separated. Being able to use different materials for different regions of the termination device may be advantageous if there are different material requirements for the different regions of the termination device, for example if the more distal portion of the termination device needs to be more flexible, and the more proximal region needs to be stiffer, or vice-versa.

In some variations, the detachable locking feature of the termination device is attached to the rest of the termination device by a releasable attachment region that has been structurally weakened between the locking feature and the rest of the termination device. For example, the termination device may comprise a scored, etched, perforated, fractured, creased, slotted or dimpled region between the locking feature and the rest of the termination device. An example of a perforated region 3120 is shown in FIG. 39. Thus, the locking feature may be composed of the same material as the rest of the termination device (or it may be made of different materials that have been fused together). Scoring, perforating or otherwise weakening the region between the locking feature and the more proximal portion of the termination device may allow the locking feature to be separated from the rest of the termination device when enough force is applied (e.g., to the termination feature by the push rod, as described above). The detachable locking feature could also be attached via an adhesive or a friction fit so that applying a certain amount of force causes the two regions of the termination device to separate, releasing the detachable locking feature. The two materials can also be welded, brazed, soldered, or snap-locked.

As described above, the locking feature can be controllably released from the rest of the termination device by applying force. Force may be applied in any appropriate manner (e.g., pushing on a push rod, hydraulic force (e.g., saline etc.), magnetic force, pressure, etc.). For example, the same push rod 3915 used to push the plug 3913 and secure the locking feature may be used to separate the locking feature from the rest of the termination device by simply pushing with additional force. In some variations, a separate force applicator may be used to secure the locking feature (e.g., a push rod) and to separate the locking feature from the rest of the termination device (e.g., a second push rod). Furthermore, the amount of force required to release the detachable locking feature may be predetermined. In variations where the locking feature is locked or triggered by the same force applicator (e.g., push rod), the force required to detach the locking feature may be greater than the force required to secure the locking feature (locking the tether). For example, the termination device may be configured to release the detachable locking feature after the application of greater than about 2 lbs of force, greater than about 3 lbs of force, greater than about 4 lbs of force, greater than about 5 lbs of force, greater than about 10 lbs of force, greater than about 20 lbs of force, or between about 2 lbs and about 5 lbs of force. The termination device may be configured to detach the locking feature by selecting an appropriate junction between the locking feature and the rest of the termination device (e.g., the thickness, material(s), scoring/perforations, etc.). In some variations, the force applicator used to release the locking feature (e.g., the push rod, fluid line, magnet, etc.) may be configured to apply a controllable force necessary to detach the locking feature. Thus, the force required to separate the locking feature from the rest of the termination device can be adjusted by fusing the materials of the locking feature and the body of the termination device together more or less, by adjusting the amount of perforation, or by changing the adhesive application or friction fit. Further, the amount of force and the way that force is applied to detach the locking feature may be controlled to prevent damage to the locking feature, the tether, the anchors, and/or the surrounding tissue. The locking feature may also be released by cutting the joint between it and the rest of the termination catheter (e.g., by a shearing blade that slides to shear the fuse joint). A cutter may also cut the cable and the joint in a combined manner, thus completely releasing the locking mechanism with the cable severed.

Although we have described only a few of the ways that a locking feature may be detachably connected to a termination device, it should be understood that any appropriate attachment may be used, including snap fits and attachment mechanisms (e.g., threads, etc.). The attachments described herein may be readily scaled in size for use with even applications requiring very small locking features (e.g., during percutaneous applications).

In operation (e.g., during an annuloplasty procedure), a locking feature is typically secured to the tether to fix its length (in some cases cinching the tether), such that the end of the tether does not slide through the eye of the most proximal anchor, as described above. After the tether is locked, the excess length of tether may be cut and removed.

Typically, cinching occurs by applying tension to the tether while bracing the termination device (e.g., including a locking feature) against the most proximal anchor. The tether may slide through the termination device when the locking feature is not in a secured state. After the desired amount of cinching is achieved, the locking feature is engaged, locking the suture in place. For example, the termination device shown in FIG. 39 can be used to secure a tether (e.g., cinching an annulus) by applying force from a push rod to push the plug 3913 into the locking feature and secure the tether. The end of the locking feature shown in FIG. 39 comprises an outer tube that is partially or completely closed (narrowed) so as the plug is pushed in, it is held securely against the tether. As described above, the plug may comprise a material which is compressible or elastic to aid in locking the plug into the end of the locking feature. In some variations, a portion of the locking feature may be configured to secure the locking feature in the locked position, and/or to secure the tether. For example, the plug 3913 shown as part of the locking feature in FIGS. 39 and 40 may have polygonal (e.g., hexagonal) sides that interact with the inner surface of the locking mechanism. The plug maybe solid or hollow. The plug may have bumps, dimples, ribs, grooves or holes on the surface to increase traction on the cable. The locking feature may also include structures (e.g., rims, brackets, etc.) to help hold the plug in the locked configuration. Thus, this locking feature (like most of the locking features described above) has an unsecured state, in which the tether may move with respect to the locking feature, and a secured state, in which the tether is secured or held by the locking feature. Once the tether is locked into position, the push-rod can be further advanced to separate the locking feature from the rest of the termination device. The outer tube may also be polygonal in cross-section.

Figure 42A:
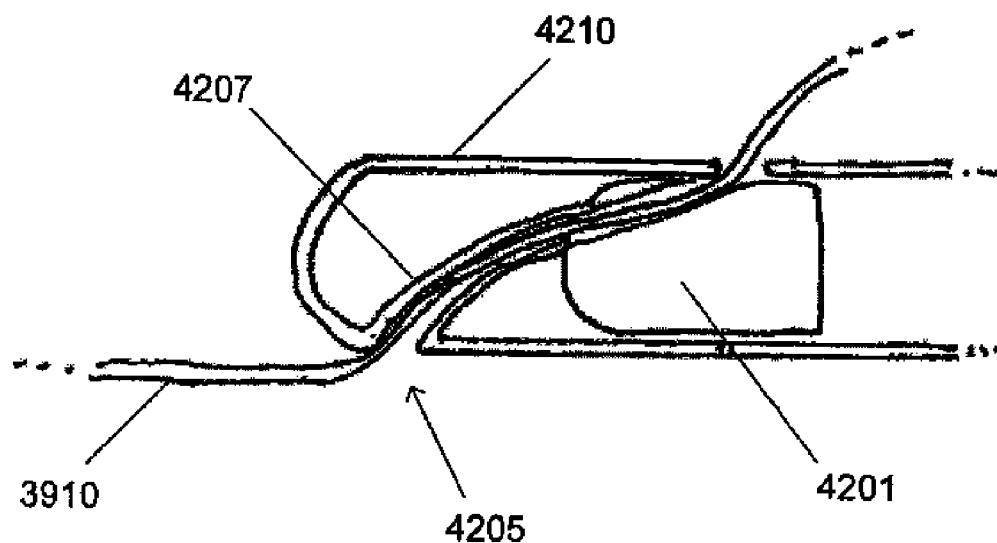
FIGS. 42A and 42B show one variation of a termination device.
Figure 42B:
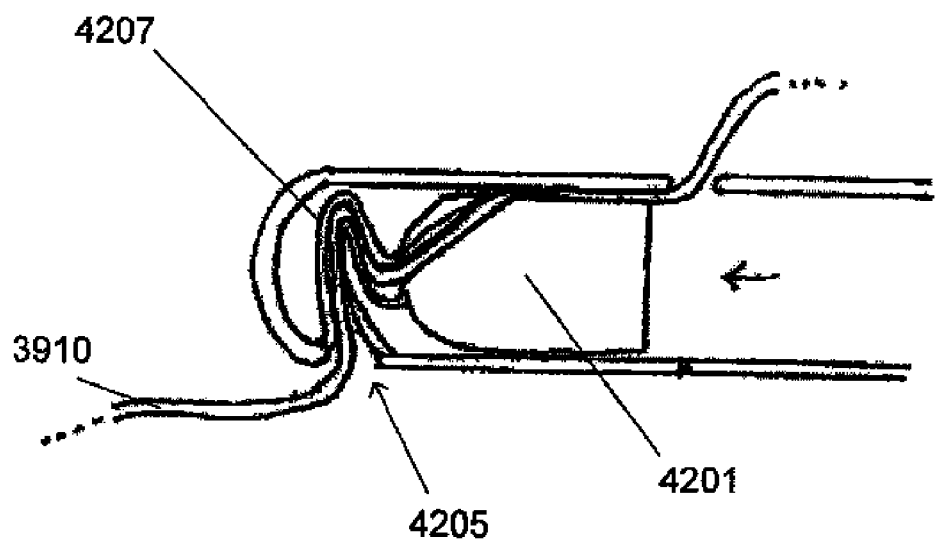

As described above, any appropriate locking feature may be used. For example, the locking feature may comprise a kinking tube that is kinked to secure a tether by a plug. In one variation, the tether passes inside of an outer tube of the locking feature through a pre-kinked smaller tube. When passing and cinching the tether, the tether is tensioned, causing the pre-kinked inner tube to straighten and thus lower the sliding force required to move the tether in the termination device. When it is desired to secure the locking feature, a plug can be pushed into the outer tube to buckle and kink the pre-kinked inner tube to secure the tether in very tight windings, locking the tether in position. FIGS. 42A and 42B show one variation of a termination device having a locking feature that fixes a tether in a tight winding path within the locking feature to secure the tether. In FIG. 42A, the locking feature is shown in the unlocked state, when the inner tube 4207 is un-kinked, allowing the tether 3910 to pass freely though the locking feature (e.g., the outer tube 4210). FIG. 42B shows the locking feature in the secured state, in which the inner (kinking) tube has been kinked so that the tether 3910 is constrained, and cannot slide freely within the inner tube 4207. In FIG. 42B, a plug 4201 is pushed forward into the distal end of the locking feature, compressing the kinking inner tube 4207 and securing the tether 3910 into the locked position.

Figure 40A:
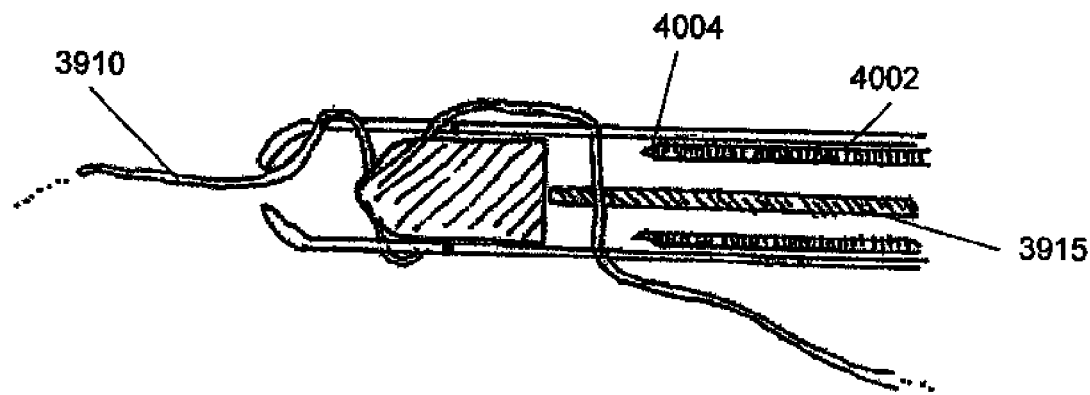
FIGS. 40A and 40B show different variations of termination devices.
Figure 40B:
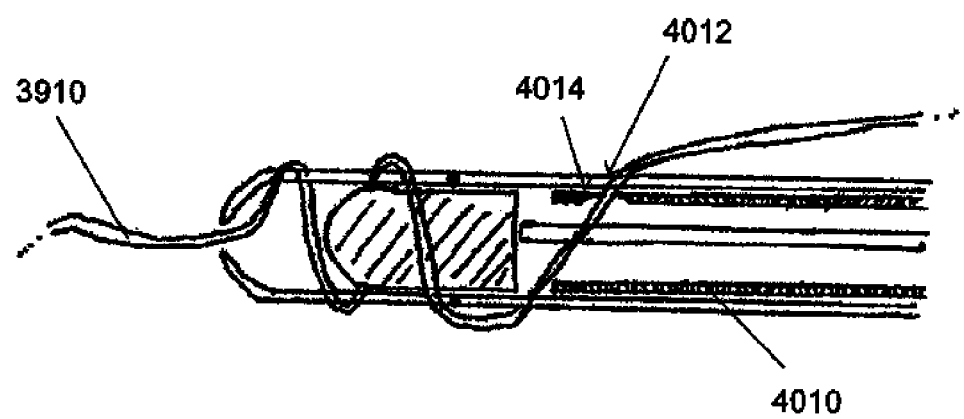

The tether may be cut to remove excess material (e.g., proximal to the locking feature) either before or after detaching the locking feature from the rest of the termination device. As previously described, the termination device (including the detachable locking feature) may be combined with any of the tether cutters described herein. FIGS. 40A and 40B illustrate different tether cutters that may be incorporated into a termination device, including the detachable locking feature. FIG. 40A shows a termination device with a detachable locking feature similar to the one shown in FIG. 39. The termination device also includes a tether cutter that is configured as a cutting tube 4002 that has a sharpened outer edge 4004. The push rod 3915 passes through the cutting tube. The termination device also includes guides which guide the tether 3910 through the termination device so that it can be positioned for cutting by the cutting tube 4002. In FIG. 40A, the tether is positioned through the termination device so that it can be readily cut by the cutting tube when the tube is brought forward (e.g., moving the cutting tube distally). In FIG. 40A, the cutting tube has at least one edge (e.g., over half of the cutting tube circumference) so that at least one end of the tether (e.g., the end contacting the more proximal end of the tether) is cut by the cutting tube. As described above, other types of tether cutters may be used as well. For example, FIG. 40B shows a similar tether cutter that is configured to cut the tether when the cutting tube 4010 is drawn proximally. In FIG. 40B, the cutting tube has a passage 4012 through which the tether 3910 passes, and at least a portion of the cutting tube is sharp 4014. The tether 3910 also passes through the wall of the termination device (configured as a catheter in FIGS. 40A and 40B). The end of the tether can be cut by drawing the tether taught after securing the locking feature of the termination device and then moving the cutting tube against the tether so that it is cut.

The exemplary termination devices shown in FIGS. 39 and 40 include passages or holes through which the tether may couple with the tether 3910. As described above, the tether may be threaded into the passages of the termination device either during use, or before inserting the termination device. The locking device portion of a termination device may include a first passage for engaging the tether on the side (e.g., a more distal side, as shown in FIGS. 42A and 42B) of the locking device, rather than at the distal end, as shown in FIGS. 39-41. In variations of the locking feature where the side is longer than width, and the tether enters the locking feature from the side, the locking feature may be held against the tissue on the longer side of the locking feature. Thus, the location where the tether first engages the locking feature may determine how the locking feature is positioned after being secured to a cinched tether.

Figure 41A:
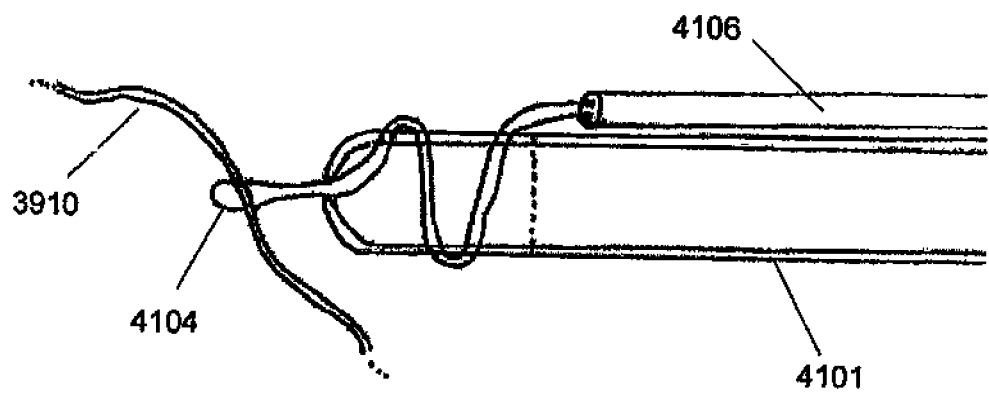
FIG. 41A shows a termination device and a loading device for loading a tether into a termination device.

In some variations, a threading device (e.g., a lasso) may be included to draw the thread through the termination device, as described above for FIGS. 14A and 14B. FIG. 41A shows another variation of a threading device 4104, preloaded into the termination device 4101. The threading device shown comprises a wire that forms a loop (e.g., a lasso), and the flattened loop passes through the holes (or passages) in the termination device. The tether may be passed through the loop, and drawn into the termination device, as previously described.

Figure 41B:
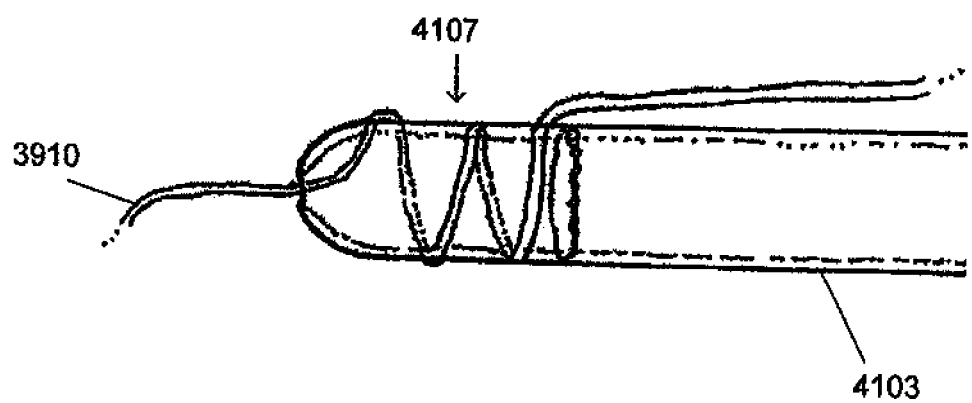
FIG. 41B shows a termination device with a detachable locking feature.
Figure 41C:
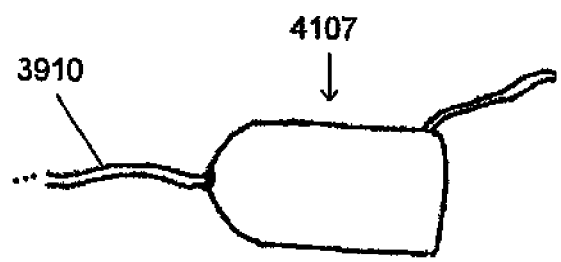
FIG. 41C shows the locking feature of FIG. 41B after detaching from the rest of the termination device.

In some variations, the termination device may include channels, guides or passages which direct the tether. For example, FIG. 41B shows a portion of a termination device having a detachable locking feature 4107. The termination device includes passages and guides which position the tether within the termination device when the tether is coupled to the termination device. Thus, the tether may be held so that it can be secured, and then cut, using the termination device. FIG. 41C shows an example of a detachable locking feature of a termination device as described from FIGS. 39-40 in which the locking feature has be secured to the tether and released from the rest of the termination device.

Although FIGS. 39-41 illustrate termination devices having detachable locking features configured as clamps, any appropriate locking feature (e.g., knot, collars, adhesives, clamps, etc.) may be used, as described above.

Furthermore, although the foregoing has been described in some detail by way of illustration and example for purposes of clarity of understanding, it is apparent to those skilled in the art that certain minor changes and modifications will be practiced. Therefore, the description and examples should be construed as limiting the scope of the invention as described in the claims.

What is claimed is:

1. A method for securing a tether during a mitral valve repair procedure comprising:

securing one or more anchors coupled to the tether to internal ventricular wall tissue of a left ventricle at or adjacent to an intersection of a mitral valve leaflet and the ventricular wall tissue, such that the one or more anchors do not penetrate into a left atrium;

advancing a tether-locking device in the left ventricle, the tether-locking device comprising an outer tubular body with a lumen therethrough, an aperture at the distal-most end of the tubular body for passage of the tether therethrough, and an inner locking member slidably retained within the lumen of the tubular body, wherein the locking device comprises an unlocked state wherein the tether is movable with respect to the locking device, and a locked state wherein the inner locking member secures at least a portion of the tether such that the tether exits the aperture at the distal-most end of the tubular body, the inner locking member is located proximally to the aperture and the tether bends against an external portion of the outer tubular body; and securing the tether with the locking device such that the locking device is located entirely in the left ventricle.

2. The method of claim 1, wherein the locking device comprises a first movable surface, and a second surface opposite the first surface, wherein the second surface is immovable.

3. The method of claim 1, wherein the locking device comprises a surface that is textured, toothed, sticky, scored, etched, or some combination thereof.

4. The method of claim 1, wherein the locking device comprises at least one protruding feature thereon.

5. The method of claim 1, wherein the locking device is made of a shape memory material.

6. The method of claim 1, further comprising cutting the tether after it has been secured.

7. The method of claim 1, further comprising unsecuring the tether after the tether has been secured.

8. The method of claim 1, wherein the slidable inner locking member comprises a cylindrical body.

9. The method of claim 1, wherein securing the tether comprises securing the tether in a tortuous path within the locking device.

10. The method of claim 1, wherein the locking device is advanced over the tether.

* * * * *